(12) United States Patent
Kufe

(10) Patent No.: US 7,871,784 B2
(45) Date of Patent: Jan. 18, 2011

(54) METHODS AND COMPOSITIONS RELATING TO THE REGULATION OF APOPTOSIS BY MUC1 AND BH3-CONTAINING PROAPOPTOTIC PROTEINS

(75) Inventor: Donald W. Kufe, Wellesley, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 206 days.

(21) Appl. No.: 12/024,715

(22) Filed: Feb. 1, 2008

(65) Prior Publication Data

US 2009/0087437 A1    Apr. 2, 2009

Related U.S. Application Data

(60) Provisional application No. 60/888,000, filed on Feb. 2, 2007.

(51) Int. Cl.
*G01N 33/53* (2006.01)
*C07K 14/46* (2006.01)

(52) U.S. Cl. .................. 435/7.1; 530/18.9; 530/21.3

(58) Field of Classification Search .................. None
See application file for complete search history.

(56) References Cited

U.S. PATENT DOCUMENTS

| | | | |
|---|---|---|---|
| 4,497,796 A | 2/1985 | Salser et al. | 514/44 |
| 4,522,811 A | 6/1985 | Eppstein et al. | 514/2 |
| 4,675,382 A | 6/1987 | Murphy | 260/112 |
| 4,740,461 A | 4/1988 | Kaufman | 435/69.1 |
| 4,894,227 A | 1/1990 | Stevens et al. | 424/85.2 |
| 4,963,484 A | 10/1990 | Kufe | 435/69.3 |
| 5,053,489 A | 10/1991 | Kufe | 530/350 |
| 5,080,898 A | 1/1992 | Murphy | 424/94.1 |
| 5,380,712 A | 1/1995 | Ballance et al. | 514/12 |
| 5,506,343 A | 4/1996 | Kufe | 530/387.7 |
| 5,530,101 A | 6/1996 | Queen et al. | 530/387.3 |
| 5,565,334 A | 10/1996 | Kufe et al. | 435/69.1 |
| 5,597,457 A | 1/1997 | Craig et al. | 204/165 |
| 5,612,895 A | 3/1997 | Balaji et al. | 702/19 |
| 5,766,883 A | 6/1998 | Ballance et al. | 435/69.7 |
| 5,776,427 A | 7/1998 | Thorpe et al. | 424/1.49 |
| 5,790,421 A | 8/1998 | Osslund | 703/2 |
| 5,801,154 A | 9/1998 | Baracchini et al. | 514/44 |
| 5,827,516 A | 10/1998 | Urban et al. | 424/93.21 |
| 5,861,381 A | 1/1999 | Chambon et al. | 514/44 |
| 5,874,415 A | 2/1999 | Kufe et al. | 514/44 |
| 5,965,386 A | 10/1999 | Kerry-Williams et al. | 435/69.1 |
| 5,998,148 A | 12/1999 | Bennett et al. | 435/6 |
| 6,004,746 A | 12/1999 | Brent et al. | 435/6 |
| 6,020,363 A | 2/2000 | Hirano et al. | 514/456 |
| 6,054,438 A | 4/2000 | Taylor-Papadimitriou et al. | 514/44 |
| 6,074,841 A | 6/2000 | Gearing et al. | 435/69.1 |
| 6,093,573 A | 7/2000 | Beamer et al. | 436/86 |
| 6,222,020 B1 | 4/2001 | Taylor-Papadimitriou et al. | 530/395 |
| 6,303,302 B1 | 10/2001 | Rupp et al. | 435/6 |
| 6,344,203 B1 | 2/2002 | Sandrin | 424/277.1 |
| 6,589,921 B2 | 7/2003 | Herrmann et al. | 514/456 |
| 6,716,627 B2 | 4/2004 | Dobie | 435/375 |
| 6,716,966 B1 | 4/2004 | Madiyalakan et al. | 530/387.1 |
| 7,147,850 B2 | 12/2006 | Madiyalakan | 514/12 |
| 2002/0110841 A1 | 8/2002 | Kufe | 435/7.23 |
| 2003/0235857 A1 | 12/2003 | Rupp et al. | 435/6 |
| 2004/0018181 A1 | 1/2004 | Kufe et al. | 424/93.21 |
| 2004/0166543 A1 | 8/2004 | Kufe | 435/7.23 |
| 2004/0209832 A1 | 10/2004 | McSwiggen | 514/44 |
| 2005/0042209 A1 | 2/2005 | Kufe et al. | 424/93.21 |
| 2005/0053606 A1 | 3/2005 | Kufe et al. | 424/155.1 |
| 2006/0019256 A1 | 1/2006 | Clarke et al. | 435/6 |
| 2008/0090770 A1 | 4/2008 | Belmares et al. | 514/18 |

FOREIGN PATENT DOCUMENTS

| | | |
|---|---|---|
| EP | 1103623 | 7/1998 |
| WO | WO 93/20841 | 10/1993 |
| WO | WO 96/03502 | 2/1996 |
| WO | WO 99/23114 | 5/1999 |
| WO | WO 91/09867 | 7/1999 |
| WO | WO 00/09744 | 2/2000 |
| WO | WO 00/11206 | 3/2000 |
| WO | WO 00/25827 | 5/2000 |
| WO | WO 00/34468 | 6/2000 |
| WO | WO 00/47763 | 8/2000 |
| WO | WO 00/77031 | 12/2000 |
| WO | WO 01/12217 | 2/2001 |
| WO | WO 01/18035 | 3/2001 |

(Continued)

OTHER PUBLICATIONS

U.S. Appl. No. 10/486,278, filed Jun. 23, 2004, Reinherz et al.

(Continued)

*Primary Examiner*—David S Romeo
(74) *Attorney, Agent, or Firm*—Fulbright & Jaworski

(57) ABSTRACT

This invention relates to regulation of cell signaling, cell growth, and more particularly to the regulation of cancer or immune cell growth. The invention provides methods of inhibiting interactions between MUC1 and BH3-containing proapoptotic proteins, methods of inhibiting MUC1 expression, and methods of promoting apoptosis. Also provided are screening methods for compounds that inhibit interactions between MUC1 and BH3-containing proapoptotic proteins and pharmaceutical compositions of the same.

5 Claims, 5 Drawing Sheets

FOREIGN PATENT DOCUMENTS

| | | |
|---|---|---|
| WO | WO 01/57068 | 8/2001 |
| WO | WO 02/22685 | 3/2002 |
| WO | WO 02/31512 | 4/2002 |
| WO | WO 02/058450 | 8/2002 |
| WO | WO 03/014303 | 2/2003 |
| WO | WO 03/088995 | 10/2003 |
| WO | WO 2004/044160 | 5/2004 |
| WO | WO 2004/092339 | 10/2004 |

OTHER PUBLICATIONS

U.S. Appl. No. 60/308,307, filed Jul. 27, 2001, Kufe.
U.S. Appl. No. 60/502,111, filed Sep. 11, 2003, Jecminek et al.
"MUC-1/X mucin short variant," GenBank Accession No. AAD10856, dated Jun. 5, 2001.
"MUC-1/Z mucin short variant," GenBank Accession No. AAD10858, dated Jun. 5, 2001.
"Mucin 1 precursor, non-repetitive splice from Y [validated]—human," GenBank Accession No. S48146, dated Apr. 20, 2000.
Abe et al., "Characterization of cis-acting elements regulating transcription of the human DF3 breat carcinoma-associated antigen (MUC1) gene," Proc. Natl. Acad. Sci. USA., 90:282-286, 1993.
Abe et al., "Identification of a family of high molecular weight tumor-associated glycoproteins," J. Immun., 139:257-261, 1987.
Abe et al., "Sequence Anaylsis of the 5' region of the human DF3 breast carcinoma-associated antigen gene," Bio. Biophys. Research Comm., 165:644-649, 1989.
Abe et al., "Sodium butyrate induction of milk-related antigens in human MCF-7 breast carcinoma cells," Cancer Res., 44:4574-4577, 1984.
Abe et al., "Structural analysis of the DF3 human breat carcinoma-associated protein," Cancer Res., 49:2834-2839, 1989.
Abe et al., "Transcriptional regulation of DF3 gene expression in human MCF-7 breast carcinoma cells," J. Cell. Physio., 143:226-231, 1990.
Adams and Cory, "The Bcl-2 Protein Family: Arbiters of Cell Survival," Science, 281:1322-1326, 1998.
Agrawal and Kandimalla, "Antisense therapeutics: is it as simple as complementary base recognition?" Molecular Medicine Today, 6:72-81, 2000.
Akagi et al., "CA19-9 epitope a possible marker for MUC-1/Y protein," Int. J. Oncol., 18:1085-1091, 2001.
Alfieri et al., "Activation of heat-shock transcription factor 1 by hypertonic shock in 3T3 cells," Biochem. J., 319:601-606, 1996.
Apostolopoulos et al., "Production of anti-breast cancer monoclonal antibodies using a glutathione-S-transferase-MUC1 bacterial fusion protein," British J. Cancer., 67:713-720, 1993.
Arklie et al., "Differentiation antigens expressed by epithelial cells in the lactating breast are also detectable in breast cancers," Int. J. Cancer, 28:23-29, 1981.
Ashkenazi and Dixit, "Apoptosis control by death and decoy receptors," Curr. Opin. Cell Biol., 11:255-260, 1999.
Ashkenazi and Dixit, "Death Receptors: Signaling and Modulation," Science, 281:1305-1308, 1998.
Ashkenazi et al., "Safety and antitumor activity of recombinant soluble Apo2 ligand," J. Clin. Invest., 104:155-162, 1999.
Backstom et al., "Recombinant MUC1 mucin with a breast cancer-like O-glycosylation produced in large amounts in Chinese-hamster ovary cells," Biochemical Journal, 376:677-686, 2003.
Banerjee, "Omega amino acids in peptide design: incorporation into helices ," Biopolymers, 39:769-77, 1996.
Barrett et al., "PLU-1 nuclear protein, which is upregulated in breast cancer, shows restricted expression in normal human adult tissues: a new cancer/testis antigen?," Int. J. Cancer, 101:581-588, 2002.
Barry and Sharkey, "Observer reproducibility during computer-assisted planimetric measurements of nuclear features," Hum. Pathol., 16:225-7, 1985.
Barry et al., "Activation of programmed cell death (apoptosis) by cisplatin, other anticancer drugs, toxins and hyperthermia," Biochemical Pharmacology, 40:2353-2362, 1990.

Baruch et al., "Preferential expression of novel MUC1 tumor antigen isoforms in human epithelial tumors and their tumor-potentiating function," Int. J. Cancer, 71:741-749, 1997.
Baruch et al., "The breast cancer-associated MUC1 gene generates both a receptor and its cognate binding protein," Cancer Res., 59:1552-1561, 1999.
Bass, "The short answer," Nature, 411:428-429, 2001.
Batra et al., "Transfection of the human MUC1 mucin gene into a poorly differentiated human pancreatic tumor cell line, Panc1: integration, expression and ultrastructural changes," J. Cell Science, 100:841-849, 1991.
Becker et al., "Three-dimensional structure of the Stat3beta homodimer bound to DNA," Nature, 394:145-151, 1998.
Bellgrau et al., "A role for CD95 ligand in preventing graft rejection," Nature, 377:630-632, 1995.
Berger et al., "Respiratory carcinoma cell lines: MUC genes and glycoconjugates," American Journal of Respiratory Cell and Molecular Biology, 20:500-510, 1999.
Bergeron et al., "MAUB is a new mucin antigen associated with bladder cancer," J. Biol. Chem., 271:6933-6940, 1996.
Beusen et al., "Conformational mimicry: synthesis and solution conformation of a cyclic somatostatin hexapeptide containing a tetrazole cis amide bond surrogate," Biopolymers, 36:181-200, 1995.
Bevilacqua et al., "Developmental activation of an episomic hsp70 gene promoter in two-cell mouse embryos by transcription factor Sp1," Nucleic Acids Res., 25:1333-1338, 1997.
Bird et al., "Single-chain antigen-binding proteins," Science, 242:423-6, 1988.
Bitko et al., "Inhibition of respiratory viruses by nasally administered siRNA," Nature Med., 11:50-55, 2005.
Bodmer et al., "Cysteine 230 is essential for the structure and activity of the cytotoxic ligand TRAIL," J. Biol. Chem., 275:20632-20637, 2000.
Boldin et al., "Involvement of MACH, a novel MORT1/FADD-interacting protease, in Fas/APO-1- and TNF receptor-induced cell death," Cell, 85:803-815, 1996.
Brody and Gold, "Aptamers as therapeutic and diagnostic agents," Rev. Mol. Biotech., 74:5-13, 2000.
Brossart et al., "Identification of HLA-A2-restricted T-cell epitopes derived from MUC1 tumor antigen for broadly applicable vaccine therapies," Blood, 93:4309-4317, 1999.
Broughton, "Molecular modeling," Curr. Opin. Chem. Biol., 1, 392-398, 1997.
Brunner et al., "pangolin encodes a Lef-1 homologue that acts downstream of Armadillo to transduce the Wingless signal in Drosophila," Nature, 385:829-33, 1997.
Bumcrot et al., "RNAi therapeutics: a potential new class of pharmaceutical drugs," Nature Chemical Biology, 2:711-719, 2006.
Bunz, "Cell death and cancer therapy," Curr. Opin. Pharmacol., 1:337-341, 2001.
Burchell et al., "A short sequence, within the amino acid tandem repeat of a cancer-associated mucin, contains immunodominant epitopes," Int. J. Cancer, 44:691-696, 1989.
Burchell et al., "Development and characterization of breast cancer reactive monoclonal antibodies directed to the core protein of the human milk mucin," Cancer Res., 47:5476-5482, 1987.
Burns and El-Deiry, "Identification of inhibitors of TRAIL-induced death (ITIDs) in the TRAIL-sensitive colon carcinoma cell line SW480 using a genetic approach," J. Biol. Chem., 276:37879-37886, 2001.
Burton et al., "Epithelial mucin (MUC1) expression and MA5 anti-MUC1 monoclonal antibody targeting in multiple myeloma," Clin. Can. Res., 5:3065s-3072s, 1999.
Busfield et al., "Characterization of a neuregulin-related gene, Don-1, that is highly expressed in restricted regions of the cerebellum and hippocampus," Mol. Cell. Biol., 17:4007-4014, 1997.
Cane et al., "Harnessing the biosynthetic code: combinations, permutations, and mutations," Science, 282:63-68, 1998.
Cawley et al., "Epidermal growth factor-toxin A chain conjugates: EGF-Ricin A is a potent toxin while EGF-Diphtheria fragment A is nontoxic," Cell, 22:563-570, 1980.

Certo et al., "Mitochondria primed by death signals determine cellular addiction to antiapoptotic BCL-2 family members," *Cancer Cell*, 9:351-365, 2006.

Chang et al., "Artificial hybrid protein containing a toxic protein fragment and a cell membrane receptor-binding moiety in a disulfide conjugate," *J. Biol. Chem.*, 252:1515-1522, 1977.

Chang et al., "Ligands for ErbB-family receptors encoded by a neuregulin-like gene," *Nature*, 387:509-512, 1997.

Chaudhary et al., "A rapid method of cloning functional variable-region antibody genes in Escherichia coli as single-chain immunotoxins," *Proc. Natl. Acad. Sci. U.S.A.*, 87:1066-70, 1990.

Chaudhary et al., "Activity of a recombinant fusion protein between transforming growth factor type alpha and Pseudomonas toxin," *Proc. Natl. Acad. Sci. USA*, 84:4538-4542, 1987.

Chen et al., "Heat shock factor 1 represses Ras-induced transcriptional activation of the c-fos gene," *J. Biol. Chem.*, 272:26803-26806, 1997.

Chou et al., "Solution structure of BID, an intracellular amplifier of apoptotic signaling," *Cell*, 96(5):615-625, 1999.

Ciborowski et al., "Screening of anti-MUC1 antibodies for reactivity with native (ascites) and recombinant (baculovirus) MUC1 and for blocking MUC1 specific cytotoxic T-lymphocytes," *Tumor Biology*, 19:147-151, 1998.

Cohen et al., "Molecular modeling software and methods for medicinal chemistry," *J. Med. Chem.*, 33: 883-894, 1990.

Console et al., "Antennapedia and HIV transactivator of transcription (TAT) "protein transduction domains" promote endocytosis of high molecular weight cargo upon binding to cell surface glycosaminoglycans," *J. Biol. Chem.*, 278 :35109-14, 2003.

Creagan et al., "Phase III clinical trial of the combination of cisplatin, dacarbazine, and carmustine with or without tamoxifen in patients with advanced malignant melanoma," *J. Clin. Oncol.*, 17:1884-1890, 1999.

Cristiano et al., "Molecular conjugates: a targeted gene delivery vector for molecular medicine," *J. Mol. Med.*, 73:479, 1995.

Croghan et al., "Tissue distribution of an epithelial and tumor-associated antigen recognized by monoclonal antibody F36/22," *Cancer Res.*, 43:4980-4988, 1983.

Cunningham et al., "Calreticulin binding and other biological activities of survival peptide Y—P30 including effects of systemic treatment of rats," *Exp. Neurol.*, 163:457-468, 2000.

Cunningham et al., "Identification of a survival-promoting peptide in medium conditioned by oxidatively stressed cell lines of nervous system origin," *J. Neurosci.*, 18:7047-7060, 1998.

Cunningham et al., "Identification of the human cDNA for new survival/evasion peptide (DSEP): studies in vitro and in vivo of overexpression by neural cells," *Exp. Neurol.*, 177:32-39, 2002.

Danial et al., "Cell death critical control points," *Cell*, 116:205-219, 2004.

Daniel and Reynolds, "The catenin p120(ctn) interacts with Kaiso, a novel BTB/POZ domain zinc finger transcription factor," *Mol. Cell. Biol.*, 19:3614-23, 1999.

Datta et al., "Overexpression of Bcl-XL by cytotoxic drug exposure confers resistance to ionizing radiation-induced internucleosomal DNA fragmentation," *Cell Growth Differ*, 6:363-370, 1995.

Dawson et al., "Synthesis of proteins by native chemical ligation," *Science*, 266:776-779, 1994.

Debnath et al., "Morphogenesis and oncogenesis of MCF-10A mammary epithelial acini grown in three-dimensional basement membrane cultures,". *Methods* 30:256-268. 2003.

Degterev et al., "Identification of small-molecule inhibitors of interaction between the BH3 domain and Bcl-xL," *Nat. Cell Biol.* 3(2):173-182, 2001.

Dejean et al., "Is MAC the knife that cuts cytochrome *c* from mitochondria during apoptosis?" *Cell Death and Differentiation*, 13:1387-1395, 2006.

Dejean et al., "Oligomeric Bax Is a Component of the Putative Cytochrome *c* Release Channel MAC, Mitochondrial Apoptosis-induced Channel," *Mol. Biol. Cell*, 16:2424-2432, 2005.

Dejean et al., "Regulation of the mitochondrial apoptosis-induced channel, MAC, by BCL-2 family proteins," *Biochem. Biophys. Acta. Mol. Basis Dis.*, 1762(2):191-201, 2006.

Deng et al., "TRAIL-induced apoptosis requires Bax-dependent mitochondrial release of Smac/DIABLO," *Genes Dev.*, 16:33-45, 2002.

Derossi et al., "Cell internalization of the third helix of the Antennapedia homeodomain is receptor-independent," *J Biol. Chem.*, 271:18188-93, 1996.

Derossi et al., "The third helix of the Antennapedia homeodomain translocates through biological membranes," *J Biol. Chem.*, 269:10444-50, 1994.

Deveraux and Reed, "IAP family proteins—suppressors of apoptosis," *Genes Dev.*, 13:239-52, 1999.

Dillman, "Antibodies as cytotoxic therapy," *J. Clin. Oncology*, 12:1497-1515, 1994.

Dorn et al., "Down-regulation of the human tumor antigen mucin by gemcitabine on the pancreatic cancer cell line capan-2," *Anticancer Research*, 24:821-826, 2004.

Doyle, "Crystal structures of a complexed and peptide-free membrane protein-binding domain: molecular basis of peptide recognition by PDZ," *Cell*, 85:1067-76, 1996.

Drucker et al., "Tamoxifen enhances apoptotic effect of cisplatin on primary endometrial cell cultures," *Anticancer Research*, 23:1549-1554, 2003.

Du et al., "Smac, a Mitochondrial Protein that Promotes Cytochrome c-Dependent Caspase Activation by Eliminating IAP Inhibition," *Cell*, 102:33-42, 2000.

Dykxhoorn et al., "The silent treatment: siRNAs as small molecule drugs," *Gene Therapy*, 13:541-552, 2006.

Elbashir et al., "Analysis of gene function in somatic mammalian cells using small interfering RNAs," *Methods*, 26:199-213, 2002.

Elbashir et al., "Functional anatomy of siRNAs for mediating efficient RNAi in Drosophila melanogaster embryo lysate," *EMBO Journal*, 20:6877-6888, 2001.

Elbashir et al., "RNA interference is mediated by 21-and 22-nucleotide RNAs," *Genes and Development*, 15:188-200, 2001.

Elliot and O'Hare, "Intercellular trafficking and protein delivery by a herpesvirus structural protein," *Cell*, 88:223-33, 1997.

Elmquist et al., "VE-cadherin-derived cell-penetrating peptide, pVEC, with carrier functions," *Exp. Cell Res.*, 269:237-44, 2001.

Emoto et al., "Proteolytic activation of protein kinase C delta by an ICE-like protease in apoptotic cells," *EMBO J.*, 14:6148-6156, 1995.

Enyedy et al., "Discovery of Small-Molecule Inhibitors of Bcl-2 through Structure-Based Computer Screening" *J. Med. Chem.*, 44(25):4313-4324, 2001.

Faivre et al., "Supraadditive effect of 2',2' difluorodeoxycytidine (gemcitabine) in combination with oxaliplatin in human cancer cell lines," *Cancer Chemother. Pharmacol.*, 44:117-123, 1999.

Feigl, "2,8-Dimethyl-4-(carboxymethyl)-6-(aminomethyl)phenoxathiin S-Dioxide: An Organic Substitute for the beta-Turn in Peptides," *J. Amer. Chem. Soc.*, 108:181-2, 1986.

Finn et al., "MUC-1 Epithelial Tumor Mucin-Based Immunity and Cancer Vaccines," *Immunol. Rev.*, 145:61-89, 1995.

Fontenot et al., "Biophysical characterization of one-, two-, and three-tandem repeats of human musin (muc-1) protein core," *Cancer Research*, 53:5386-5394, 1993.

Frankel and Pabo, "Cellular uptake of the tat protein from human immunodeficiency virus ," *Cell*, 55:1189-93, 1989.

French and Tschopp, "Inhibition of Death Receptor Signaling by FLICE-inhibitory Protein as a Mechanism for Immune Escape of Tumors," *J. Exp. Med.*, 190:891-893, 1999.

Futaki et al., "Arginine-rich peptides. An abundant source of membrane-permeable peptides having potential as carriers for intracellular protein delivery," *J. Biol. Chem.*, 276 :5836-40, 2001.

Gay et al., "Selective BRB2 SH2 inhibitors as anti-RAS therapy," *Int. J. Cancer*, 83:235-241, 1999.

Geisbert et al., "Postexposure Protection of Guinea Pigs against a Lethal Ebola Virus Challenge is Conferred by RNA Interference," *J. Infectious Diseases*, 193:1650-1657, 2006.

Gendler et al., "A highly immunogenic region of a human polymorphic epithelial mucin expressed by carcinomas is made up of tandem repeats," *J. Biol. Chem.*, 263:12820-12823, 1988.

Gendler et al., "Molecular cloning and expression of human tumor-associated polymorphic epithelial mucin," *J. Biol. Chem.*, 265:15286-15293, 1990.

George, D.G. et al., "Chapter 12. Current Methods in Sequence Comparison and Analysis," in: Macromolecular Sequencing and Synthesis. Selected Methods and Applications, Alan R. Liss, Inc., pp. 127-149 (1988).

Giardina and Lis, "Dynamic protein-DNA architecture of a yeast heat shock promoter," Mol. Cell. Biol., 15:2737-2744, 1995.

Gopalakrishnan et al., "Application of Micro Arrayed Compound Screening (microARCS) to identify inhibitors of caspase-3," J. Biomol. Screen, 7:317-23, 2002.

Green and Loewenstein, "Autonomous functional domains of chemically synthesized human immunodeficiency virus tat trans-activator protein ," Cell, 55:1179-88, 1989.

Green et al., "Apoptotic pathways: ten minutes to dead," Cell, 121:671-674, 2005.

Griffith et al., "CD95-Induced Apoptosis of Lymphocytes in an Immune Privileged Site Induces Immunological Tolerance," Immunity, 5:7-16, 1996.

Gronenborn et al., "Protein structure determination in solution by two-dimensional and three-dimensional nuclear magnetic resonance spectroscopy," Anal. Chem., 62(1):2-15, 1990.

Gross et al., "Caspase cleaved BID targets mitochondria and is required for cytochrome c release, while BCL-XL prevents this release but not tumor necrosis factor-R1/Fas death," J. Biol. Chem., 274:1156-1163, 1999.

Grzelinski et al., "RNA interference-mediated gene silencing of pleiotrophin through polyethylenimine-complexed small interfering RNAs in vivo exerts antitumoral effects in glioblastoma xenografts," Human Gene Therapy, 17:751-766, 2006.

Guihard et al., "The Mitochondrial Apoptosis-induced Channel (MAC) Corresponds to a Late Apoptotic Event," J. Biol. Chem., 45:46542-46550, 2004.

Gutierrez et al., "Gene therapy for cancer," The Lancet, 339:715-721, 1992.

Haim et al., "Dexamethasone, cytarabine, ifosfamide, and cisplatin as salvage therapy in Non-Hodgkin lymphoma," Am. J. Clin. Oncol., 22:47-50, 1999.

Hammond et al., "Post-transcriptional gene silencing by double-stranded RNA," Nature Genetics, 2:110-119, 2001.

Hanson et al.,"MUC1 expression in primary breast cancer: the effect of tamoxifen treatment," Breast Cancer Research and Treatment, 67:215-222, 2001.

Harborth et al., "Identification of essential genes in cultured mammalian cells using small interfering RNAs," J. Cell Science, 114:4557-4565, 2001.

Hareuveni et al., "A transcribed gene, containing a variable number of tandem repeats, codes for a human epithelial tumor antigen. cDNA cloning, expression of the transfected gene and over-expression in breast cancer tissue," Eur. J. Biochem., 189:475-486, 1990.

Harlow and Lane, "Antibodies, A Lab Manual," Cold Spring Harbor, 1988.

Harris et al., "Therapeutic antibodies—the coming of age," Tibtech, 11:12-44, 1993.

Harrison, "Peptide-surface association: the case of PDZ and PTB domains," Cell, 86:341-343, 1996.

Hartman et al.,"MUC1 isoform specific monoclonal antibody 6E6/2 detects preferential expression of the novel MUC1/Y protein in breast and ovarian cancer," Int. J. Cancer, 82:256-267, 1999.

Hayes et al., "Comparison of circulating CA15-3 and carcinembryonic antigen levels in patients with breast cancer," J. Clin. Oncol., 4:1542-1550, 1986.

Hayes et al., "Genetically determined polymorphism of the circulating human breast cancer-associated DF3 antigen," Blood, 71:436-440, 1988.

Herr and Debatin, "Cellular stress response and apoptosis in cancer therapy," Blood, 98:2603-2614, 2001.

Higashiyama et al., "A novel brain-derived member of the epidermal growth factor family that interacts with ErbB3 and ErbB4," J. Biochem., 122:675-680, 1997.

Higgins, "Comparison of the solution conformations of a human immunodeficiency virus peptidomimetic and its retro-inverso isomer using 1 H NMR spectroscopy," J. Pept. Res., 50:421-35, 1997.

Hilkens et al., "Biosynthesis of MAM-6, an epithelial sialomucin," J. Biol. Chem., 263:4215-4222, 1988.

Hilkens et al., "Cell membrane-associated mucins and their adhesion-modulating property," Trends in Biochem. Sciences, 17:359-362, 1992.

Hilkens et al., "Complexity of MAM-6, an epithelial sialomucin associated with carcinomas," Cancer Res., 49:786-793, 1989.

Hilkens et al., "Monoclonal antibodies against human milk-fat globulte membranes detecting differentiation antigens of the mammary gland and its tumors," Int. J. Cancer, 34:197-206, 1984.

Hird et al., "Adjuvant therapy of ovarian cancer with radioactive monoclonal antibody," Br. J. Cancer, 68:403-406, 1993.

Hodge et al., "The role of IL-6 and STAT3 in inflammation and cancer," Eur. J. Cancer, 41:2502-2512, 2005.

Honemann et al., "The IL-6 receptor antagonist SANT-7 overcomes bone marrow stromal cell-mediated drug resistance of multiple myeloma cells," Int. J. Cancer, 93:674-680, 2001.

Hopp, "Protein surface analysis. Methods for identifying antigenic determinants and other interaction sites," J. Immunol. Methods, 88:1-18, 1986.

Houghton et al., "Monoclonal antibodies: potential applications to the treatment of cancer," Seminars in Oncology, 13:165-179, 1986.

Hruby et al., "Design of peptides, proteins, and peptidomimetics in chi space," Biopolymers, 43:219-66, 1997.

Huang et al., "MUC1 cytoplasmic domain coactivates Wnt target gene transcription and confers transformation," Cancer Biol. Ther., 2:702-706, 2003.

Hug et al., "Liposomes for the transformation of eukaryotic cells," Biochem. Biophys. Acta., 1097:1-17, 1991.

Hull et al., "Oligosaccharide differences in the DF3 sialomucin antigen from normal human milk and the BT-20 human breast carcinomas cell line," Cancer Commun., 1:261-267, 1989.

Hunt and Evans, "Till Death Us Do Part," Science, 293:1784-1785, 2001.

Huston et al., "Protein engineering of antibody binding sites: recovery of specific activity in an anti-digoxin single-chain Fv analogue produced in Escherichia coli," Proc. Natl. Acad. Sci U.S.A., 85:5879-83, 1988.

Hymowitz et al., "Triggering cell death: the crystal structure of Apo2L/TRAIL in a complex with death receptor 5," Mol. Cell., 4:563-571, 1999.

Ikeda et al., "Induction of redox imbalance and apoptosis in multiple myeloma cells by the novel triterpenoid 2-cyano-3, 12-dioxoolean-1, 9-dien-28-oic acid," Molecular Cancer Therapeutics, 3:39-45, 2004.

Irmler et al., "Inhibition of death receptor signals by cellular FLIP," Nature, 388:190-195, 1997.

Itzkowitz et al., "Sialosyl-Tn. A novel mucin antigen associated with prognosis in colorectal cancer patients," Cancer, 66:1960-6, 1990.

J. Cavanagh et al., Protein NMR Spectroscopy, Principles and Practice, Academic Press, San Diego, 1996.

Jaattela et al., "Bcl-x and Bcl-2 inhibit TNF and Fas-induced apoptosis and activation of phospholipase A2 in breast carcinoma cells," Oncogene, 10:2297-2305, 1995.

Jackson et al., "Blockade of epidermal growth factor- or heregulin-dependent ErbB2 activation with the anti-ErbB2 monoclonal antibody 2C4 has divergent downstream signaling and growth effects," Cancer Res., 64:2601-2609, 2004.

Jackson, "Contributions of protein structure-based drug design to cancer chemotherapy," Seminars in Oncology, 24:L164-172, 1997.

Jawhari et al., "Up-regulated cytoplasmic expression, with reduced membranous distribution, of the src substrate p120(ctn) in gastric carcinoma," J. Pathol. 189:180-5, 1999.

Jen et al., "Suppression of gene expression by targeted disruption of messenger RNA: available options and current strategies," Stem Cells, 18:307-319, 2000.

Jin et al., "CIAP1 and the serine protease HTRA2 are involved in a novel p53-dependent apoptosis pathway in mammals," Genes Dev., 17:359-67, 2003.

Jones et al., "Structure-based design of lipophilic quinazoline inhibitors of thymidylate synthase," J. Med. Chem., 39:904-917, 1996.

Julian and Carson, "Formation of MUC1 metabolic complex is conserved in tumor-derived and normal epithelial cells," Biochem. Biophys. Res. Commun., 293:1183-1190, 2002.

Kahn et al., "Nonpeptide Mimetics of beta-Turns: A Facile Oxidative Intramolecular Cycloaddition of an Azodicarbonyl System," *J. Amer. Chem. Soc.*, 110:1638-9, 1988.

Kahn, "The design and synthesis of mimetics of peptide beta-turns," *J. Molec. Recognition*, 1:75-9, 1988.

Kalofonos et al., "Kinetics, quantitative analysis and radioimmunolocalisation using indium-111-HMFG1 monoclonal antibody in patients with breast cancer," *Cr. J. Cancer*, 59:939-942, 1989.

Kalofonos et al., "Radioimmunoschintigraphy in patients with ovarian cancer," *Acta Oncologica*, 38:629-634, 1999.

Kam et al.,"MUC1 synthetic peptide inhibition of intracellular adhesion molecule-1 and MUC1 binding requires six tandem repeats," *Cancer Res.*, 58:5577-5581, 1988.

Karlsson et al., "A genetic polymorphism of a human urinary mucin," *Ann. Hum. Genet.*, 47:263, 1983.

Karvinen et al., "Homogeneous time-resolved fluorescence quenching assay (LANCE) for caspase-3," *J. Biomol. Screen*, 7:223-31, 2002.

Kataoka et al., "FLIP prevents apoptosis induced by death receptors but not by perforin/granzyme B, chemotherapeutic drugs, and gamma irradiation," *J. Immunol.*, 161:3936-3942, 1998.

Kayagaki et al., "Metalloproteinase-mediated release of human Fas ligand," *J. Exp. Med.*, 182:1777-1783, 1995.

Kelekar et al., "Bcl-2-family proteins: the role of the BH3 domain in apoptosis," *Trends Cell Biol.*, 8:324-330, 1998.

Kemp and Stites, "A convenient preparation of derivatives of 3(s)-amino-109(r)-carboxy-1,6-diaza-cyclodeca-2,7-dione the dilactam of L-alph,gamma-diaminobutyric acid and d-glutamic acid: a beta-turn template," *Tet. Lett.*, 29:5057-60, 1988.

Kennerdell et al., "Heritable gene silencing in *Drosophila* using double-stranded RNA," *Nature Biotechnology*, 17:896-898, 2000.

Khaleque et al., "Induction of heat shock proteins by heregulin betal leads to protection from apoptosis and anchorage-independent growth," *Oncogene*, 24:6564-6573, 2005.

Kharbanda et al., "Nuclear signaling induced by ionizing radiation involves colocalization of the activated p56/p53lyn tyrosine kinase with p34cdc2," *Cancer Res.*, 56:3617-3621, 1996.

Kim et al., "Cholesteryl oligoarginine delivering vascular endothelial growth factor siRNA effectively inhibits tumor growth in colon adenocarcinoma," *Molecular Therapy*, 14:343-350, 2006.

Kischkel et al., "Cytotoxicity-dependent APO-1 (Fas/CD95)-associated proteins form a death-inducing signaling complex (DISC) with the receptor," *EMBO J.*, 14:5579-5588, 1995.

Kluck et al., "The Release of Cytochrome c from Mitochondria: A Primary Site for BCL-2 Regulation of Apoptosis," *Science*, 275:1132-1136, 1997.

Kondo et al., "Decreased MUC1 expression induces E-Cadherin-mediated cell adhesion of breast cancer cell lines," *Cancer Research*, 58:2014-2019, 1998.

Kotera et al., "Humoral immunity against a tandem repeat epitope of human mucin MUC-1 in Ser from breat, pancreatic, and colon cancer patients," *Cancer Research*, 54:2856-2860, 1994.

Kroemer and Reed, "Mitochondrial control of cell death," *Nat. Med.*, 6:513-519, 2000.

Kufe et al., "Differential reactivity of a novel monoclonal antibody (DF3) with human malignant versus benign breast tumors," *Hybridoma*, 3:223-232, 1984.

Kumar et al., "Abrogation of the cell death response to oxidative stress by the c-Abl tyrosine kinase inhibitor STI571," *Mol. Pharmacol.*, 63:276-282, 2003.

Kuppuswamy et al., "Multiple functional domains of Tat, the trans-activator of HIV-I, defined by mutational analysis," *Nucl. Acids Res.*, 17:3551-61, 1989.

Kuwana et al., "Bid, Bax, and Lipids Cooperate to Form Supramolecular Openings in the Outer Mitochondrial Membrane," *Cell*, 111:331-342, 2002.

Lancaster et al., "Structure and expression of the human polymorphic epithelial mucin gene: an expressed VNTR unit," *Biochm. Biophys. Res. Comm.*, 173:1019-1029, 1990.

LaVallee et al., "2-Methoxyestradiol up-regulates death receptor 5 and induces apoptosis through activation of the extrinsic pathway," *Cancer Research*, 63:468-475, 2003.

LeBlanc et al., "Tumor-cell resistance to death receptor—induced apoptosis through mutational inactivation of the proapoptotic Bcl-2 homolog Bax," *Nat. Med.*, 8:274-281, 2002.

Letai et al., "Distinct BH3 domains either sensitize or activate mitochondrial apoptosis, serving as prototype cancer therapeutics," *Cell*, 2:183-192, 2002.

Lewis et al., "Efficient delivery of siRNA for inhibition of gene expression in postnatal mice," *Nature Genetics*, 32:107-108, 2002.

Li and Kufe, "The human DF3/MUC1 carcinoma-associated antigen signals nuclear localization of the catenin p120$^{ctn}$," *Biochem. Biophys. Res. Commun.*, 281:440-443, 2001.

Li et al., "The c-Src tyrosime kinase regulates signaling of the human DF3/MUC1 carcinoma-associated anitgen with GSK3β and β-catenin," *J. Biol. Chem.*, 276:6061-6064, 2001.

Li et al., "Cleavage of BID by Caspase 8 Mediates the Mitochondrial Damage in the FAS Pathway of Apoptosis," *Cell*, 94:491-501, 1998.

Li et al., "Cytochrome c and dATP-Dependent Formation of Apaf-1/Caspase-9 Complex initiates and Apoptotic Protease Cascade," *Cell*, 91:479-489, 1997.

Li et al., "DF3/MUC1 signaling in multiple myeloma cells is regulated by interleukin-7," *Cancer Biol. Ther.*, 2:187-193, 2003.

Li et al., "Heregulin targets gamma-catenin to the nucleolus by a mechanism dependent on the DF3/MUC1 oncoprotein," *Mol. Cancer Res.*, 1:765-775, 2003.

Li et al., Human DF3/MUC1 carcinoma-associated protein functions as an oncogene *Oncogene*, 22:6107-6110, 2003.

Li et al., "Interaction of glycogen synthase kinase 3β with the DFC/MUC1 carcinoma-associated antigen and β-catenin," *Mol. Cell. Biol.*, 18:7216-7224, 1998.

Li et al., "The c-Src tyrosine kinase regulates signaling of the human DF3/MUC1 carcinoma-associated antigen with GSK3β and β-catenin," *J. Biol. Chem.*, 276:6061-6064, 2001.

Li et al., "The EGF receptor regulates interaction of the human DF3/MUC1 carcinoma antigen with c-SRC and β-catenin," *JBC Papers in Press*, manuscript C100359200, Aug. 1, 2001.

Li et al., "The epidermal growth factor receptor regulates interaction of the human DF3/MUC1 carcinoma antigen with c-Src and beta-catenin,"*J Biol. Chem.*, 276:35236-42, 2001.

Li et al., "Using siRNA in prophylactic and therapeutic regimens against SARS coronavirus in Rhesus macaque," *Nature Med.*, 11:944-951, 2005.

Ligtenberg et al., "Cell associated episialin is a complex containing two proteins derived from a common precurso," *J. Biol. Chem.*, 267:6171-6177, 1992.

Ligtenberg et al., "Suppression of Cellular Aggregation by High Levels of Episialin," *Cancer Res.*, 52:2318-2324, 1992.

Lin et al., "Inhibition of nuclear translocation of transcription factor NF-kappa B by a synthetic peptide containing a cell membrane-permeable motif and nuclear localization sequence," *J. Biol. Chem.*, 270:14255-8, 1995.

Liu et al., "Identification of a functionally important sequence in the cytoplasmic tail of integrin beta 3 by using cell-permeable peptide analogs," *Proc. Natl Acad. Sci. U.S.A.*, 93 :11819-24, 1996.

Liu et al., "Induction of Apoptotic Program in Cell-Free Extracts: Requirement of dATP and Cyochrome c," *Cell*, 86:147-157, 1996.

Liu et al., "The Structure of a Bcl-$x_L$/Bim Fragment Complex Implications for Bim Function," *Immunity*, 19(3):341-352, 2003.

Lundy et al., "Monoclonal antibody DF3 correlates with tumor differentiation and hormone receptor status in breast cancer patients," *Breast Cancer Res. Treat.*, 5:269-276, 1985.

Luo et al., "An efficient intrathecal delivery of small interfering RNA to the spinal cord and peripheral neurons," *Molecular Pain*, 1:29, 2005.

Luo et al., "Bid, A Bcl2 Interacting Protein, Mediates Cytochrome c Release from Mitochondria in Response to Activation of Cell Surface Death Receptors," *Cell*, 94:481-490, 1998.

Makimura et al., "Reducing hypothalamic AGRP by RNA interference increases metabolic rate and decreases body weight without influencing food intake," *BMC Neuroscience*, 3:18, 2002.

Manome et al., "Enhancer sequences of the DF3 gene regulate expression of the herpes simplex virus thymidine kinase gene and confer sensitivity of human breast cancer cells to ganciclovir," *Cancer Research*, 54:5408-5413, 1994.

Maraveyas et al., "Pharmacokinetics and toxicity of an Yttrium-90-CITC-DTPA-HMFG1 radioimmunoconjugate for intraperitoneal radioimmunotherapy of ovarian cancer," *Cancer*, 73:1067-1075, 1994.

Maraveyas et al., "Pharmacokinetics, biodistribution, and dosimetry of specific and control radiolabeled monoclonal antibodies in patients with primary head and neck squamous cell carcinoma," *Cancer Research*, 55:1060-1069, 1995.

Mariani et al., "Regulation of cell surface APO-1/Fas (CD95) ligand expression by metalloproteases," *Eur. J. Immunol.*, 25:2303-2307, 1995.

Marsters et al., "A novel receptor for Apo2L/TRAIL contains a truncated death domain," *Curr. Biol.*, 7:1003-1006, 1997.

Martinez et al., "Single-stranded antisense siRNAs guide target RNA cleavage in RNAi," *Cell*, 110:563-574, 2002.

Martins, "The serine protease Omi/HtrA2: a second mammalian protein with a Reaper-like function," *Cell Death Diff*, 9:699-701, 2002.

McGrath et al., "The Yeast STE6 gene encodes a homologue of the mammalian mulitdrug resistance P-Glycoprotein," *Nature*, 340:400, 1989.

McGuckin et al., "Prognostic significance of MUC1 epithelial mucin expression in breast cancer," *Human Pathology*, 26:432-439, 1995.

McPherson, "Crystallization of proteins from polyethylene glycol," *J. Biol. Chem.*, 251:6300-6306, 1976.

Melani et al., "Inhibition of proliferation by c-myb antisense oligodeoxynucleoides in colon adenocarcinoma cell lines that express c-myb," *Cancer Research*, 51:2897-2901, 1991.

Merlo et al., "Frequent alteration of the DF3 tumor-associated antigen gene in primary human breat carcinomas," *Cancer Res.*, 49:6966-6971, 1989.

Mi et al., "Characterization of a class of cationic peptides able to facilitate efficient protein transduction in vitro and in vivo," *Mol. Ther.*, 2:339-47, 2000.

Milik et al., "Lung lymphocyte elimination by apoptosis in the murine response to intratracheal particulate antigen," *J. Clin. Invest.*, 99:1082-1091, 1997.

Minakuchi et al., "Atelocollagen-mediated synthetic small interfering RNA delivery for effective gene silencing in vitro and in vivo," *Nucleic Acids Research*, 32:e109, 2004.

Molenaar et al., XTcf-3 transcription factor mediates beta-catenin-induced axis formation in Xenopus embryos, *Cell*, 86:391-9, 1996.

Morris et al., "A new peptide vector for efficient delivery of oligonucleotides into mammalian cells," *Nucleic Acid Res.*, 25:2730-6, 1997.

Muthuswamy et al., "ErbB2, but not ErbB1, reinitiates proliferation and induces luminal repopulation in epithelial acini," *Nat. Cell Biol.*, 3:785-792, 2001.

Muzio et al., "FLICE, A Novel FADD-Homologous ICE/CED-3-like Protease, Is Recruited to the CD95 (fas/APO-1) Death-Inducing Signaling Complex," *Cell*, 85:817-827, 1996.

Myers, "Will combinatorial chemistry deliver real medicines?," *Curr. Opin. Biotechnol.*, 8:701-707, 1997.

Nagai and Sato, "Synthesis of a bicylic dipeptide with the shape of beta-turn central part," *Tet. Lett.*, 26:647-50, 1985.

Nagata, "Apoptosis by Death Factor," *Cell*, 88:355-365, 1997.

Nakamura et al., "RNA interference targeting transforming growth factor-beta type II receptor suppresses ocular inflammation and fibrosis," *Molecular Vision*, 10:703-711, 2004.

Nakashima et al., "Inhibition of angiogenesis by a new isocoumarin, NM-3," *J. Antibiotics*, 52:426-428, 1999.

Navia et al., "Use of structural information in drug design," *Current Opinions in Structural Biology*, 2, pp. 202-210, 1992.

Neyfakh et al., "Efflux-mediated multidrug resistance in *Bacillus subtilis*: similarities and dissimilarities with the mammalian system," *Proc. Natl. Acad. Sci. USA*, 88:4781-4785, 1991.

Nicholson et al., "Radioimmunotherapy after chemotherapy compared to chemotherapy alone in the treatment of advanced ovarian cancer: a matched analysis," *Oncology Reports* 5:223-226, 1998.

Niethammer et al., "CRIPT, a novel postsynaptic protein that binds to the third PDZ domain of PSD-95/SAP90," *Neuron*, 20:693-707, 1989.

Nishimoto et al., "Humanized anti-interleukin-6 receptor antibody treatment of multicentric Castleman disease," *Blood*, 106:2627-2632, 2005.

Niu et al., "Inhibition of HPV 16 E6 oncogene expression by RNA interference in vitro and in vivo," *Int. J. Gynecol. Cancer*, 16:743-751, 2006.

Novak and Dedhar, "Signaling through beta-catenin and Lef/Tcf," *Cell Mol. Life Sci*, 523-37, 1999.

Obermair et al., "Expression of MUC1 splice variants in benign and malignant ovarian tumours," *Int. J. Cancer*, 100:166-171, 2002.

Oehlke et al., "Cellular uptake of an alpha-helical amphipathic model peptide with the potential to deliver polar compounds into the cell interior non-endocytically," *Biochim. Biophys. Acta.*, 1414:127-39, 1998.

Okazaki et al., "Downregulation of gastric mucin gene expression and its biosynthesis by dexamethasone in the human," *J. Clin. Gastroenterol.*, 27(suppl. 1):S91-S92, 1998.

Oosterkamp et al., "Comparison of MUC-1 mucin expression in epithelial and non-epithelial cancer cell lines and demonstration of a new short variant form (MUC-1/Z)," *Int. J. Cancer*, 72:87-94, 1997.

Opalinska et al., "Nucleic-acid therapeutics: basic principles and recent applications," *Nature Reviews Drug Discovery*, 1:503-514, 2002.

Orkin Report & Recommendations of The Panel to Assess the NIH Investment in Research on Gene Therapy, 1995.

Padrón et al., "Selective cell kill of the combination of gemcitabine and cisplatin in multilayered postconfluent tumor cell cultures," *Anti-Cancer Drugs*, 10:445-452, 1999.

Palliser et al., "An siRNA-based microbicide protects mice from lethal herpes simplex virus 2 infection," *Nature*, 439:89-94, 2006.

Pan et al., "An Antagonist Decoy Receptor and a Death Domain-Containing Receptor for TRAIL," *Science*, 277:815-818, 1997.

Pan et al., "The Receptor for the Cytotoxic Ligand TRAIL," *Science*, 276:111-113, 1997.

Pandy et al., "Association of the DF3/MUC1 breast cancer antigen with Grb2 and the Sos/Ras exchange protein," *Cancer Res.*, 55:4000-4003, 1995.

Parrish et al., "Functional anatomy of a dsRNA trigger: differential requirement for the two trigger strands in RNA interference," *Molecular Cell*, 8:1077-1087, 2000.

Parry et al., "Identification of MUC1 proteolytic cleavage sites in vivo," *Biochem. Biophys. Res. Commun.*, 283:715-720, 2001.

Paszkiewicz-Gadek et al., "Biosynthesis of MUC1 mucin in human endometrial adenocarcinoma is modulated by estradiol and tamoxifen," *Gynecol. Endocrinol.*, 17:37-44, 2003.

Pavlovic et al., "Targeting of non-small cell lung cancer using HMFG1-$^{99m}$TC monoclonal antibodies," *Med Pregl.*, 46 Suppl 1:26-28, 1993.

Perey et al., "Tumor selective reactivity of a monoclonal antibody prepared against a recombinant peptide derived from the DF3 human breast carcinoma-associated antigen," *Cancer Research*, 52:2563-2568, 1992.

Perez et al., "Antennapedia homeobox as a signal for the cellular internalization and nuclear addressing of a small exogenous peptide," *J. Cell. Sci.*, 102:717-22, 1992.

Pescarolo et al., "A retro-inverso peptide homologous to helix 1 of c-Myc is a potent and specific inhibitor of proliferation in different cellular systems," *FASEB J.*, 15:31-3, 2001.

Pitti et al., "Induction of Apoptosis by Apo-2 Ligand, a New Member of the Tumor Necrosis Factor Cytokine Family," *J. Biol. Chem.*, 271:12687-12690, 1996.

Pooga et al., "Cell penetrating PNA constructs regulate galanin receptor levels and modify pain transmission in vivo," *Nature Biotech.*, 16 :857-61, 1998.

Porowska et al., "MUC1 expression in human breast cancer cells is altered by the factors affecting cell proliferation," *Neoplasma*, 49:104-109, 2002.

Porter et al., "A neural survival factor is a candidate oncogene in breast cancer," *Proc. Natl. Acad. Sci. USA*, 100:10931-10936, 2003.

Price et al, "Immunological and structural features of the protein core of human polymorphic epithelial mucin," *Molecular Immunology*, 27:795-802, 1990.

Price et al., "Summary report on the ISOBM TD-4 workshop: analysis of 56 monoclonal antibodies against the MUC1 mucin," San Diego, California, Nov. 17-23, 1996, *Tumor Biol.*, 19:sup. 1:1-20, 1998.

Raina et al. "The MUC1 oncoprotein activates the anti-apoptotic phosphoinositide 3-kinase/Akt and Bcl-xL pathways in rat 3Y1 fibroblasts," *J. Biol. Chem,.* 279:20607-20612, 2004.

Reddish et al., "Pre-immunotherapy serum CA27.29 (MUC-1) mucin level and CD69+ lymphocytes correlate with effects of Theratope sialyl-Tn-KLH cancer vaccine in active specific immunotherapy," *Cancer Immunol. Immunother.*, 42:303-9, 1996.

Reich et al., "Small interfering RNA (siRNA) targeting VEGF effectively inhibits ocular neovascularization in a mouse model," *Molecular Vision*, 9:210-216, 2003.

Ren et al., "Human MUC1 carcinoma-associated protein confers resistance to genotoxic anticancer agents," *Cancer Cell*, 5:163-175, 2004.

Ren et al., "MUC1 oncoprotein is targeted to mitochondria by heregulin-induced activation of c-Src and the molecular chaperone HSP90," *Oncogene*, 25:20-31,2006.

Ren et al., "Protein kinase C δ regulates function of the DFC/MUC1 carcinoma antigen in β-catenin signaling," *J. Biol. Chem.*, 277:17616-17622, 2002.

Rewcastle et al., "Tyrosine kinase inhibitors. 14. Structure-activity relationships for methylamino-substituted derivatives of 4-[(3-Bromophenyl) amino]-6-(methylamino)-pyride [3,4-*d*] pyrimidine (PD 158780), a potent and specific inhibitor of the tyrosine kinase activity of receptors for the EGF family of growth factors," *J. Med. Chem.*, 41:742-751, 1998.

Reynolds et al., "Identification of a new catenin: the tyrosine kinase substrate p120cas associates with E-cadherin complexes," *Mol. Cell. Biol.*, 14:8333-42, 1994.

Reynolds et al., "Transformation-specific tyrosine phosphorylation of a novel cellular protein in chicken cells expressing oncogenic variants of the avian cellular src gene," *Mol. Cell. Biol.*, 9:629-38, 1989.

Rondinone, "Therapeutic potential of rnai in metabolic diseases," *BioTechniques*, 40:S31-S36, 2006.

Rousselle et al., "New advances in the transport of doxorubicin through the blood-brain barrier by a peptide vector-mediated strategy," *Mol. Pharmacol.*, 57 :679-86, 2000.

Ruben et al., "Structural and functional characterization of human immunodeficiency virus tat protein," *J. Virol.*, 63(1):1-8, 1989.

Sato et al., "FAP-1: A Protein Tyrosine Phosphatase That Associates with Fas," *Science*, 268:411-415, 1995.

Sattler et al., "Structure of Bcl-xL-Bak peptide complex: Recognition between regulators of apoptosis," *Science*, 275(5302):983-986, 1997.

Scaffidi et al., "Differential Modulation of Apoptosis Sensitivity in CD95 Type I and Type II Cells," *J. Biol. Chem.*, 274:22532-22538, 1999.

Schiffelers et al., "Cancer siRNA therapy by tumor selective delivery with ligand-targeted sterically stabilized nanoparticle," *Nucleic Acids Research*, 32:e149, 2004.

Schneider et al., "Mutagenesis and selection of PDZ domains that bind new protein targets," *Nat. Biotech.*, 17:170-5, 1998.

Schroeder et al., "Transgenic MUC1 interacts with epidermal growth factor receptor and correlates with mitogen-activated protein kinase activation in the mouse mammary gland," *J Biol Chem*, 276:13057-13064, 2001.

Schultz et al., "Specific interactions between the syntrophin PDZ domain and voltage-gated sodium channels," *Nat. Struct. Biol.*, 5:19-24, 1998.

Schumacher et al., "Immunoscintigraphy with positron emission tomography: Gallium-68 chelate imaging of breast cancer pretargeted with bispecific anti-MUC1/anti-Ga chelate antibodies," *Cancer Research*, 61:3712-3717, 2001.

Sekine et al., "Purification and characterization of a high molecular weight glycoprotein detectable in human milk and breast carcinomas," *J. Immunol.*, 135:3610-3615, 1985.

Shen et al., "Suppression of ocular neovascularization with siRNA targeting VEGF receptor 1," *Gene Therapy*, 13:225-234, 2006.

Sherman et al., "Ionizing radiation regulates expression of the c-jun protooncogene," *Proc. Natl. Acad. Sci. USA*, 87:5663-5666, 1990.

Shimazui et al., "Prognostic value of cadherin-associated molecules (alpha- , beta- , and gamma-catenins and p120cas) in bladder tumors," *Cancer Res.*, 56:4154-8, 1996.

Siddiqui et al., "Isolation and sequencing of a cDNA coding for the human DF3 breast carcinoma-associated antigen," *Proc. Natl. Acad. Sci. USA*, 85:2320-2323, 1988.

Sloan et al., Distribution of epithelial membrane antigen in normal and neoplastic tissues and its value in diagnostic tumor pathology, *Cancer*, 47:1786-1795, 1981.

Smith and Waterman, "Comparison of Biosequences," *Adv. Appl. Math.*, 2:482-9, 1981.

Smith, "Design, Synthesis, and Crystal Structure of a Pyrrolinon-Based Peptidomimetic Possessing the Conformation of a beta-Strand: Potential Application to the Design of Novel Inhibitors of Proteolytic Enzymes," *J. Amer. Chem. Soc.*, 114:10672-4, 1992.

Smolen and Maini, "Interleukin-6: a new therapeutic target," *Arthritis Res. & Ther.*, 8(Suppl. 2):S5, 2006.

Snyder et al., "Treatment of Terminal Peritoneal Carcinomatosis by a Transducible p53-Activating peptide," *PLoS Biology*, 2:186-93, 2004.

Songyang et al., "Recognition of unique carboxyl-terminal motifs by distinct PDZ domains," *Science*, 275:73-7, 1997.

Soomets et al., "Deletion analogues of transportan," *Biochim. Biophys. Acta*, 1467:165-176, 2000.

Soutschek et al., "Therapeutic silencing of an endogenous gene by systemic administration of modified siRNAs," *Nature*, 432:173-178, 2004.

Spatola, "A Peptide Backbone Modifications," In: Chemistry and Biochemistry of Amino Acids, Peptides and Proteins, 7:267-357, Marcell Dekker, NY, 1983.

Srinivasan et al., "Bcl-xL functions downstream of caspase-8 to inhibit Fas- and tumor necrosis factor receptor 1-induced apoptosis of MCF7 breast carcinoma cells," *J. Biol. Chem.*, 273:4523-4529, 1998.

Srinivasula et al., "Autoactivation of procaspase-9 by Apaf- 1 -mediated oligomerization," *Mol. Cell.*, 1:949-957, 1998.

Stennicke et al., "Pro-caspase-3 is a major physiologic target of caspase-8," *J. Biol. Chem.*, 273:27084-27090, 1998.

Strous and Decker, "Mucin-Type Glycoproteins," *Crit. Rev. Biochem., Mol. Biol.*, 27:57-92, 1992.

Struhl, "Deletion mapping a eukaryotic promoter," *Proc. Natl. Acad. Sci. USA*, 78:4461-4465, 1981.

Subbarao et al., "pH-dependent bilayer destabilization by an amphipathic peptide," *Biochemistry*, 26:2964-2972, 1987.

Suzuki et al., "Structure of Bax: coregulation of dimer formation and intracellular localization," *Cell*, 103:645-654, 2000.

Swallow et al., "The human tumour-associated epithelial mucins are coded by an expressed hypervariable gene locus PUM," *Nature*, 328:82-84, 1987.

Takei et al., "A small interfering RNA targeting vascular endothelial growth factor as cancer therapeutics," *Cancer Research*, 64:3365-3370, 2004.

Takeichi, "Cadherins: a molecular family important in selective cell-cell adhesion," *Annu. Rev. Biochem.*, 59:237-52, 1990.

Talpaz et al., "Dasatinib in imatinib-resistant Philadelphia chromosome-positive leukemias," *N. Engl. J. Med.*, 354:2531-41, 2006.

Taylor et al., "Antisense oligonucleotides: a systematic high-throughput approach to target validation and gene function determination," *Drug Discovery Today*, 4:562-567, 1999.

Thakker et al., "siRNA-mediated knockdown of the serotonin transporter in the adult mouse brain," *Molecular Psychiatry*, 10:782-789, 2005.

Timmer et al., "Fas receptor-mediated apoptosis: a clinical application?" *J. Pathol.*, 196:125-134, 2002.

Tondini et al., "Comparison of CA15-3 and carcinoembryonic antigen in monitoring the clinical course of patients with metastatic breast cancer," *Cancer Res.*, 48:4107-4112, 1988.

Tondini et al., "Evaluation of monoclonal antibody DF3 conjugated with ricin as a specific immunotoxin for in Vitro purging of human bone marrow," *Cancer Research*, 50:1170-1175, 1990.

Topp et al., "MUC-1 specific T-cells are present in multiple myeloma patients at high frequency after allogeneic transplantation buy may not mediated the graft versus myeloma effect," *Blood*, 100: page Abstract No. 5191, 2002.

Torchilin and Levchenko, "TAT-liposomes: a novel intracellular drug carrier," *Curr. Protein Pept. Sci.*, 4:133-40, 2003.

Tseng et al., "Translocation of liposomes into cancer cells by cell-penetrating peptides penetratin and tat: a kinetic and efficacy study," *Mol. Pharmacol.*, 62:864-72, 2002.

Urban-Klein et al., "RNAi-mediated gene-targeting through systemic application of polyethylenimine (PEI)-complexed siRNA in vivo," *Gene Therapy*, 12:461-466, 2005.

Van Hof et al., "Biodistribution of 111Indium-labeled engineered human antibody CTMO1 in ovarian cancer patients: influence of protein dose," *Cancer Research*, 56:5179-5185, 1996.

Van Zonneveld et al., "Type 1 plasminogen activator inhibitor gene: Functional analysis and glucocorticoid regulation of its promoter," *Proc. Natl. Acad. Sci. USA*, 85:5525-5529, 1988.

Verhagen et al., "Identifcation of DIABLO, a Mammalian Protein that Promotes Apoptosis by Binding to and Antagonizing IAP Proteins," *Cell*, 102:43-53, 2000.

Vermeer et al., "Segregation of receptor and ligand regulates activation of epithelial growth factor receptor," *Nature*, 422:322-326, 2003.

Vives et al., "A truncated HIV-1 Tat protein basic domain rapidly translocates through the plasma membrane and accumulates in the cell nucleus," *J. Biol. Chem.*, 272 :16010-7, 1997.

Vleck et al., "Pseudorabies virus immediate-early gene overlaps with an oppositely oriented open reading frame: Characterization of their promoter and enhancer regions," *Virology*, 179:365,337, 1990.

Walczak et al., "TRAIL-R2: a novel apoptosis-mediating receptor for TRAIL," *EMBO J.*, 16:5386-5397, 1997.

Walczak et al., "Tumoricidal activity of tumor necrosis factor-related apoptosis-inducing ligand in vivo," *Nat. Med.*, 5:157-163, 1999.

Waldmann, "Monoclonal antibodies in diagnosis and therapy," *Science* 252:1657-1662, 1991.

Walsh et al., "Heterogeneity of MUC1 expression by human breast carcinoma cell lines in vivo and in vitro," *Breast Cancer Research and Treatment*, 58:255-266, 2000.

Wang and El-Deiry, "TRAIL and apoptosis induction by TNF-family death receptors," *Oncogene*, 24:8628-8633, 2003.

Wang et al., "Expression of a dominant negative heat shock factor-1 construct inhibits aneuploidy in prostate carcinoma cells," *J. Biol. Chem.*, 279:32651-32659, 2004.

Wang et al., "Phosphorylation of HSF1 by MAPK-activated protein kinase 2 on serine 121, inhibits transcriptional activity and promotes HSP90 binding," *J. Biol. Chem.*, 281:782-791, 2006.

Weber, "Physical principles of protein crystallization," *Advances in Protein Chemistry*, 41:1-36, 1991.

Wei et al., "Human MUC1 oncoprotein regulates p53-responsive gene transcription in the genotoxic stress response," *Cancer Cell*, 7:167-178, 2005.

Wei et al., "MUC1 oncoprotein stabilizes and activates estrogen receptor α," *Molecular Cell*, 21:295-305, 2006.

Wei et al., "Proapoptotic BAX and BAK: A requisite gateway to mitochondrial dysfunction and death," *Science*, 292:727-730, 2001.

Wender et al., "The design, synthesis, and evaluation of molecules that enable or enhance cellular uptake: peptoid molecular transporters," *Proc. Natl. Acad. Sci., U.S.A.*, 97:13003-8, 2000.

Wider, "Structure determination of biological macromolecules in solution using NMR spectroscopy," *BioTechniques*, 29:1278-1294, 2000.

Williams et al., "Selective inhibition of growth factor-stimulated mitogenesis by a cell-permeable Grb2-binding peptide," *J. Biol. Chem.*, 272:22349-54, 1997.

Wreschner et al., "Does a novel form of the breast cancer marker protein MUC1, act as receptor molecule that modulates signal transduction," In: *Antigen and Antibody Molecular Engineering in Breast Cancer Diagnosis and Treatment*, Ed. Ceriani Plenum Press, New York, pp. 17-26, 1994.

Xia et al., "siRNA-mediated gene silencing in vitro and invivo," *Nature Biotechnology*, 20:1006-1010, 2002.

Xing et al, "Synthetic peptides reactive with anti-human milk fat globule membrane monoclonal antibodies," *Cancer Research*, 50:89-96, 1990.

Xing et al., "Effect of variations in peptide sequence on anti-human milk fat globule membrane antibody reactions," *Immunology*, 72:304-311, 1991.

Xing et al., "Epitope mapping of anti-breast and anti-ovarian mucin monoclonal antibodies," *Molecular Immunology*, 29:641-650, 1992.

Xing et al., "Monoclonal antibodies reactive with mucin expressed in breast cancer," *Immunol. Cell. Biol.*, 67:183-195, 1989.

Xing et al., Second generation anti-MUC1 peptide monoclonal antibodies, *Cancer Research*, 52:2310-2317, 1992.

Yamamoto et al., "Interaction of the DF3/MUC1 breast carcinoma-associated antigen and beta-catenin in cell adhesion," *J. Biol. Chem.*, 272:12492-4, 1997.

Yang et al., "Prevention of Apoptosis by Bcl-2: Release of Cytochrome c from Mitochondria Blocked," *Science*, 275:1129-1132, 1997.

Yang et al., "Structure-based design and characterization of a Novel IL-6 antagonist peptide," *Mol. Immunol.*, 42:1015-1021, 2005.

Yeh et al., "Design of yeast-secreted albumin derivatives for human therapy: biological and antiviral properties of a serum albumin-CD4 genetic conjugate," *Proc. Natl. Acad. Sci. USA*, 89:1904-1908, 1992.

Yin et al., "Human MUC1 carcinoma antigen regulates intracellular oxidant levels and the apoptotic response to oxidative stress," *Biol. Chem.*, 278:35458-35464, 2003.

Yin et al., "MUC1 oncoprotein activates the FOXO3a transcription factor in a survival response to oxidative stress," *Biol. Chem.*, 279:45721-45727, 2004.

Zhang et al., "Nucleic acid aptamers in human viral disease," *Arch. Immunol. Ther. Exp.*, 52:307-315, 2004.

Zhao et al., "An RNA aptamer that interferes with the DNA binding of the HSF transcription activator," *Nucleic Acids Res.*, 34:3755-3761, 2006.

Zimmerman et al., "RNAi-mediated gene silencing in non-human primates," *Nature*, 441:111-114, 2006.

Zrihan-Licht et al., "Characterization and molecular cloning of a novel MUC1 protein, devoid of tandem repeats, expressed in human breast cancer tissue," *Eur. J. Biochem.*, 224:787-795, 1994.

Zrihan-Licht et al., "Tyrosine phosphorylation of the MUC1 breast cancer membrane proteins: cytokine receptor-like molecules," *FEBS Let.*, 356:130-136, 1994.

The International Search Report and Written Opinion, issued in International Application No. PCT/US08/52799, dated Sep. 16, 2008.

Ren et al., "MUC1 oncoprotein functions in activation of fibroblast growth factor receptor signaling," *Mol. Cancer Res.*, 4(11): 873-883, 2006.

MDCEVNNGSSLRDECITNLLVFGFLQSCSDNSFRRELDALGHELPVLAPQWEGYDELQT
DGNRSSHSRLGRIEADSESQEDIIRNIARHLAQVGDSMDRSIPPGLVNGLALQLRNTSRSE
EDRNRDLATALEQLLQAYPRDMEKEKTMLVLALLLAKKVASHTPSLLRDVFHTTVNFI
NQNLRTYVRSLARNGMD

FIG. 1C

MAKQPSDVSSECDREGRQLQPAERPPQLRPGAPTSLQTEPQGNPEGNHGGEGDSCPHGS
PQGPLAPPASPGPFATRSPLFIFMRRSSLLSRSSSGYFSFDTDRSPAPMSCDKSTQTPSPPC
QAFNHYLSAMASMRQAEPADMRPEIWIAQELRRIGDEFNAYYARRVFLNNYQAAEDHP
RMVILRLLRYIVRLVWRMH

FIG. 1D

MDGSGEQPRGGGPTSSEQIMKTGALLLQGFIQDRAGRMGGEAPELALDPVPQDASTKK
LSECLKRIGDELDSNMELQRMIAAVDTDSPREVFFRVAADMFSDGNFNWGRVVALFYF
ASKLVLKALCTKVPELIRTIMGWTLDFLRERLLGWIQDQGGWDGLLSYFGTPTWQTVTI
FVAGVLTASLTIWKKMG

FIG. 2C

MASGQGPGPPRQECGEPALPSASEEQVAQDTEEVFRSYVFYRHQQEQEAEGVAAPADP
EMVTLPLQPSSTMGQVGRQLAIIGDDINRRYDSEFQTMLQHLQPTAENAYEYFTKIATRP
AATPTACLRVASIGAVWWLFWASATVWPYTSTSMA

FIG. 2D

MTPGTQSPFFLLLLLTVLTVVTGSGHASSTPGGEKETSATQRSSVPSSTEKNAIPAPTTTK
SCRETFLKCFCRFINKGVFWASPILSSVSDVPFPFSAQSGAGVPGWGIALLVLVCVLVAL
AIVYLIALAVCQCRRKNYGQLDIFPARDTYHPMSEYPTYHTHGRYVPPSSTDRSPYEKVS
AGNGGSSLSYTNPAVAATSANL

SEQUENCE LISTING

<160> NUMBER OF SEQ ID NOS: 7

<210> SEQ ID NO 1
<211> LENGTH: 203
<212> TYPE: PRT
<213> ORGANISM: Homo sapiens

<400> SEQUENCE: 1

```
Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Ile Pro Ala Pro Thr Thr Thr Lys Ser Cys Arg
    50                  55                  60

Glu Thr Phe Leu Lys Cys Phe Cys Arg Phe Ile Asn Lys Gly Val Phe
65                  70                  75                  80

Trp Ala Ser Pro Ile Leu Ser Ser Val Ser Asp Val Pro Phe Pro Phe
                85                  90                  95

Ser Ala Gln Ser Gly Ala Gly Val Pro Gly Trp Gly Ile Ala Leu Leu
            100                 105                 110

Val Leu Val Cys Val Leu Val Ala Leu Ala Ile Val Tyr Leu Ile Ala
        115                 120                 125

Leu Ala Val Cys Gln Cys Arg Arg Lys Asn Tyr Gly Gln Leu Asp Ile
    130                 135                 140
```

```
Phe Pro Ala Arg Asp Thr Tyr His Pro Met Ser Glu Tyr Pro Thr Tyr
145                 150                 155                 160

His Thr His Gly Arg Tyr Val Pro Pro Ser Ser Thr Asp Arg Ser Pro
            165                 170                 175

Tyr Glu Lys Val Ser Ala Gly Asn Gly Gly Ser Ser Leu Ser Tyr Thr
        180                 185                 190

Asn Pro Ala Val Ala Ala Thr Ser Ala Asn Leu
        195                 200
```

```
<210> SEQ ID NO 2
<211> LENGTH: 72
<212> TYPE: PRT
<213> ORGANISM: Homo sapiens

<400> SEQUENCE: 2

Cys Gln Cys Arg Arg Lys Asn Tyr Gly Gln Leu Asp Ile Phe Pro Ala
1               5                   10                  15

Arg Asp Thr Tyr His Pro Met Ser Glu Tyr Pro Thr Tyr His Thr His
            20                  25                  30

Gly Arg Tyr Val Pro Pro Ser Ser Thr Asp Arg Ser Pro Tyr Glu Lys
        35                  40                  45

Val Ser Ala Gly Asn Gly Gly Ser Ser Leu Ser Tyr Thr Asn Pro Ala
    50                  55                  60

Val Ala Ala Ser Ala Asn Leu
65                  70
```

```
<210> SEQ ID NO 3
<211> LENGTH: 195
<212> TYPE: PRT
<213> ORGANISM: Homo sapiens

<400> SEQUENCE: 3

Met Asp Cys Glu Val Asn Asn Gly Ser Ser Leu Arg Asp Glu Cys Ile
1               5                   10                  15

Thr Asn Leu Leu Val Phe Gly Phe Leu Gln Ser Cys Ser Asp Asn Ser
            20                  25                  30

Phe Arg Arg Glu Leu Asp Ala Leu Gly His Glu Leu Pro Val Leu Ala
        35                  40                  45

Pro Gln Trp Glu Gly Tyr Asp Glu Leu Gln Thr Asp Gly Asn Arg Ser
    50                  55                  60

Ser His Ser Arg Leu Gly Arg Ile Glu Ala Asp Ser Glu Ser Gln Glu
65                  70                  75                  80

Asp Ile Ile Arg Asn Ile Ala Arg His Leu Ala Gln Val Gly Asp Ser
            85                  90                  95

Met Asp Arg Ser Ile Pro Pro Gly Leu Val Asn Gly Leu Ala Leu Gln
        100                 105                 110

Leu Arg Asn Thr Ser Arg Ser Glu Glu Asp Arg Asn Arg Asp Leu Ala
    115                 120                 125

Thr Ala Leu Glu Gln Leu Leu Gln Ala Tyr Pro Arg Asp Met Glu Lys
130                 135                 140

Glu Lys Thr Met Leu Val Leu Ala Leu Leu Ala Lys Lys Val Ala
145                 150                 155                 160

Ser His Thr Pro Ser Leu Leu Arg Asp Val Phe His Thr Thr Val Asn
            165                 170                 175

Phe Ile Asn Gln Asn Leu Arg Thr Tyr Val Arg Ser Leu Ala Arg Asn
        180                 185                 190
```

Gly Met Asp
        195

<210> SEQ ID NO 4
<211> LENGTH: 198
<212> TYPE: PRT
<213> ORGANISM: Homo sapiens

<400> SEQUENCE: 4

Met Ala Lys Gln Pro Ser Asp Val Ser Ser Glu Cys Asp Arg Glu Gly
1               5                   10                  15

Arg Gln Leu Gln Pro Ala Glu Arg Pro Pro Gln Leu Arg Pro Gly Ala
            20                  25                  30

Pro Thr Ser Leu Gln Thr Glu Pro Gln Gly Asn Pro Glu Gly Asn His
        35                  40                  45

Gly Gly Glu Gly Asp Ser Cys Pro His Gly Ser Pro Gln Gly Pro Leu
    50                  55                  60

Ala Pro Pro Ala Ser Pro Gly Pro Phe Ala Thr Arg Ser Pro Leu Phe
65                  70                  75                  80

Ile Phe Met Arg Arg Ser Ser Leu Leu Ser Arg Ser Ser Ser Gly Tyr
                85                  90                  95

Phe Ser Phe Asp Thr Asp Arg Ser Pro Ala Pro Met Ser Cys Asp Lys
            100                 105                 110

Ser Thr Gln Thr Pro Ser Pro Pro Cys Gln Ala Phe Asn His Tyr Leu
        115                 120                 125

Ser Ala Met Ala Ser Met Arg Gln Ala Glu Pro Ala Asp Met Arg Pro
    130                 135                 140

Glu Ile Trp Ile Ala Gln Glu Leu Arg Arg Ile Gly Asp Glu Phe Asn
145                 150                 155                 160

Ala Tyr Tyr Ala Arg Arg Val Phe Leu Asn Asn Tyr Gln Ala Ala Glu
                165                 170                 175

Asp His Pro Arg Met Val Ile Leu Arg Leu Leu Arg Tyr Ile Val Arg
            180                 185                 190

Leu Val Trp Arg Met His
        195

<210> SEQ ID NO 5
<211> LENGTH: 192
<212> TYPE: PRT
<213> ORGANISM: Homo sapiens

<400> SEQUENCE: 5

Met Asp Gly Ser Gly Glu Gln Pro Arg Gly Gly Gly Pro Thr Ser Ser
1               5                   10                  15

Glu Gln Ile Met Lys Thr Gly Ala Leu Leu Leu Gln Gly Phe Ile Gln
            20                  25                  30

Asp Arg Ala Gly Arg Met Gly Gly Glu Ala Pro Glu Leu Ala Leu Asp
        35                  40                  45

Pro Val Pro Gln Asp Ala Ser Thr Lys Lys Leu Ser Glu Cys Leu Lys
    50                  55                  60

Arg Ile Gly Asp Glu Leu Asp Ser Asn Met Glu Leu Gln Arg Met Ile
65                  70                  75                  80

Ala Ala Val Asp Thr Asp Ser Pro Arg Glu Val Phe Phe Arg Val Ala
                85                  90                  95

Ala Asp Met Phe Ser Asp Gly Asn Phe Asn Trp Gly Arg Val Val Ala
            100                 105                 110

```
Leu Phe Tyr Phe Ala Ser Lys Leu Val Leu Lys Ala Leu Cys Thr Lys
            115                 120                 125

Val Pro Glu Leu Ile Arg Thr Ile Met Gly Trp Thr Leu Asp Phe Leu
    130                 135                 140

Arg Glu Arg Leu Leu Gly Trp Ile Gln Asp Gln Gly Gly Trp Asp Gly
145                 150                 155                 160

Leu Leu Ser Tyr Phe Gly Thr Pro Thr Trp Gln Thr Val Thr Ile Phe
                165                 170                 175

Val Ala Gly Val Leu Thr Ala Ser Leu Thr Ile Trp Lys Lys Met Gly
            180                 185                 190

<210> SEQ ID NO 6
<211> LENGTH: 153
<212> TYPE: PRT
<213> ORGANISM: Homo sapiens

<400> SEQUENCE: 6

Met Ala Ser Gly Gln Gly Pro Gly Pro Pro Arg Gln Glu Cys Gly Glu
1               5                   10                  15

Pro Ala Leu Pro Ser Ala Ser Glu Glu Gln Val Ala Gln Asp Thr Glu
            20                  25                  30

Glu Val Phe Arg Ser Tyr Val Phe Tyr Arg His Gln Gln Glu Gln Glu
        35                  40                  45

Ala Glu Gly Val Ala Ala Pro Ala Asp Pro Glu Met Val Thr Leu Pro
    50                  55                  60

Leu Gln Pro Ser Ser Thr Met Gly Gln Val Gly Arg Gln Leu Ala Ile
65                  70                  75                  80

Ile Gly Asp Asp Ile Asn Arg Arg Tyr Asp Ser Glu Phe Gln Thr Met
                85                  90                  95

Leu Gln His Leu Gln Pro Thr Ala Glu Asn Ala Tyr Glu Tyr Phe Thr
            100                 105                 110

Lys Ile Ala Thr Arg Pro Ala Ala Thr Pro Thr Ala Cys Leu Arg Val
        115                 120                 125

Ala Ser Ile Gly Ala Val Trp Trp Leu Phe Trp Ala Ser Ala Thr Val
    130                 135                 140

Trp Pro Tyr Thr Ser Thr Ser Met Ala
145                 150

<210> SEQ ID NO 7
<211> LENGTH: 135
<212> TYPE: PRT
<213> ORGANISM: Homo sapiens

<400> SEQUENCE: 7

Gly Asn Arg Ser Ser His Ser Arg Leu Gly Arg Ile Glu Ala Asp Ser
1               5                   10                  15

Glu Ser Gln Glu Asp Ile Ile Arg Asn Ile Ala Arg His Leu Ala Gln
            20                  25                  30

Val Gly Asp Ser Met Asp Arg Ser Ile Pro Pro Gly Leu Val Asn Gly
        35                  40                  45

Leu Ala Leu Gln Leu Arg Asn Thr Ser Arg Ser Glu Glu Asp Arg Asn
    50                  55                  60

Arg Asp Leu Ala Thr Ala Leu Glu Gln Leu Leu Gln Ala Tyr Pro Arg
65                  70                  75                  80

Asp Met Glu Lys Glu Lys Thr Met Leu Val Leu Ala Leu Leu Leu Ala
                85                  90                  95
```

-continued

```
Lys Lys Val Ala Ser His Thr Pro Ser Leu Leu Arg Asp Val Phe His
            100                 105                 110

Thr Thr Val Asn Phe Ile Asn Gln Asn Leu Arg Thr Tyr Val Arg Ser
        115                 120                 125

Leu Ala Arg Asn Gly Met Asp
    130                 135
```

US 7,871,784 B2

METHODS AND COMPOSITIONS RELATING TO THE REGULATION OF APOPTOSIS BY MUC1 AND BH3-CONTAINING PROAPOPTOTIC PROTEINS

This application claims the benefit of the filing date of U.S. provisional patent application Ser. No. 60/888,000, filed Feb. 2, 2007, the entire content of which is hereby incorporated by reference.

The research described in this application was supported by grant no. CA97098 from the National Cancer Institute of the National Institutes of Health. Thus, the government has certain rights in the invention.

BACKGROUND OF THE INVENTION

I. Field of the Invention

This invention relates to regulation of cell signaling and cell growth, and more particularly to the regulation of cancer or immune cell growth.

II. Description of Related Art

The MUC1 heterodimeric mucin-type glycoprotein is expressed on the apical borders of secretory epithelial cells (Kufe et al. (1984) Hybridoma 3:223-232). With transformation and loss of polarity, MUC1 is expressed at high levels over the entire cell membrane and in the cytoplasm (Kufe et al. (1984) Hybridoma 3:223-232). The MUC1 N-terminal ectodomain, which consists of variable numbers of 20 amino acid tandem repeats that are extensively modified by O-linked glycans, is tethered to the cell surface through a complex with the MUC1 C-terminal transmembrane subunit (MUC1-C) (Siddiqui et al. (1988) Proc. Natl. Acad. Sci. USA 85:2320-2323; Gendler et al. (1988) J. Biol. Chem. 263:12820-12823; and Merlo et al. (1989) Cancer Res. 49:6966-6971). MUC1-C integrates receptor tyrosine kinase signaling with the Wnt pathway (Li et al. (1998) Mol. Cell. Biol. 18:7216-7224; Li et al. (2001) J. Biol. Chem. 276:35239-35242; and Li et al. (2001) J. Biol. Chem. 276:6061-6064). MUC1-C is also targeted to mitochondria and to the nucleus, where it contributes to the regulation of β-catenin/Tcf- and p53-mediated gene transcription (Ren et al. (2004) Cancer Cell 5:163-175; Huang et al. (2003) Cancer Biol. Ther. 2:702-706; and Wei et al. (2005) Cancer Cell 7:167-178). Overexpression of MUC1 is sufficient to induce transformation and to attenuate apoptosis in the response of cells to oxidative and genotoxic stress (Ren et al. (2004) Cancer Cell 5:163-175; Huang et al. (2003) Cancer Biol. Ther. 2:702-706; Li et al. (2003) Oncogene 22:6107-6110; Raina et al. (2004) J. Biol. Chem. 279:20607-20612; and Yin et al. (2004) J. Biol. Chem. 279:45721-45727).

Heregulin (HRG) induces MUC1 expression in MCF10A cells. HRG increases (i) c-Src-mediated phosphorylation of MUC1-C on Tyr-46, (ii) binding of MUC1-C and HSP90, and (iii) targeting of MUC1-C to the mitochondrial outer membrane (MOM) in breast cancer cells (Ren et al. (2006) Oncogene 25:20-31). Unlike breast cancer cells, little if any MUC1-C is detectable in mitochondria of MCF10A cells.

MUC1-C localizes to the MOM and blocks release of mitochondrial apoptogenic proteins (Ren et al. (2004) Cancer Cell 5:163-175; Ren et al. (2006) Oncogene 25:20-31; Yin et al. (2002) J. Biol. Chem. 277:17616-17622). How MUC1-C regulates mitochondrial outer membrane permeabilization (MOMP), which allows release of proteins in the intermembrane space to diffuse in to the cytosol (Green et al. (2005) Cell 121:671-674), is not known. However, information is available regarding the role of Bcl-2 family members in regulating MOMP. The proapoptotic BH3-only proteins (e.g., BID, BIM) interact with the multidomain proapoptotic BAX and BAK, which in turn oligomerize to form a pore in the MOM that is essential for permeabilization (Wei et al. (2001) Science 292:727-730; Kuwana et al. (2002) Cell 111:331-342). The BH3-only proteins can also neutralize the multidomain anti-apoptotic (e.g., Bcl-2, Bcl-$x_L$) proteins that block BAX and BAK oligomerization (Certo et al. (2006) Cancer Cell 9:351-365).

SUMMARY OF THE INVENTION

This invention is based, at least in part, on the discovery that MUC1 associates with BH3-containing proapoptotic proteins such as BID and BAX. Since both MUC1 and BH3-containing proapoptotic proteins are known to regulate apoptosis, it is expected that modulation of these interactions would influence apoptosis in cell (e.g., induce apoptosis in a cell such as a cancer cell an inflammatory cell). Furthermore, in that many cells including cancer cells and immune effector cells express MUC1 and BH3-containing proteins, inhibition of such interactions (e.g., using small molecule compounds) could be useful in the treatment of diseases such as cancer and inflammatory conditions.

Herein is provided a method of identifying a compound that inhibits the binding of MUC1 to a BH3-containing proapoptotic protein. The method includes the steps of: contacting a MUC1 reagent with a BH3-containing proapoptotic protein reagent in the presence of a candidate compound; and determining whether the candidate compound inhibits binding of the MUC1 reagent to the BH3-containing proapoptotic reagent. The method can optionally include the steps of providing a MUC1 reagent and/or providing a BH3-containing proapoptotic protein (e.g., BAK, BAX, BIM, or BID) reagent. The method can be performed (i.e., carried out) in a cell or in a cell-free system. In embodiments where the method is carried out in a cell, cells suitable for the method can be any prokaryotic cell (e.g., a bacterial cell) or eukaryotic cell (e.g., a yeast cell, a nematode cell, an insect cell, a bird cell, a mammalian cell (e.g., a mouse cell, a rat cell, a guinea pig cell, a horse cell, a cow cell, a pig cell, a goat cell, a donkey cell, a monkey cell, or a human cell)). In some embodiments, the BH3-containing proapoptotic protein reagent can be, or contain, BID, t-BID, BAX, BIM, BAK, BAD, or MUC1-binding fragments of any of the foregoing. In some embodiments, the MUC1 reagent comprises the cytoplasmic domain of MUC1 (MUC1-CD), e.g., the MUC1-CD as depicted in SEQ ID NO:2

Also provided is a process of manufacturing a compound, which includes the steps of, after determining that a compound inhibits the interaction between MUC1 and BH3-containing proapoptotic protein (through the method preceding method), manufacturing the compound.

Also provided is a method of generating a compound that inhibits the interaction between MUC1 and a BH3-containing proapoptotic protein, which method includes the steps of: providing a three-dimensional structure of a molecule or a molecular complex, the structure comprising: (a) the cytoplasmic domain of MUC1 or a BH3-containing proapoptotic protein-binding fragment thereof; (b) a molecule comprising a BH3-containing proapoptotic protein or a MUC1-binding fragment thereof; or (c) a molecular complex comprising (a) and (b); designing, based on the three-dimensional structure, a compound comprising a region that inhibits the interaction between MUC1 and the BH3-containing proapoptotic protein; and producing the compound. In some embodiments, the BH3-containing proapoptotic protein can be, or contain, BID or a MUC1-binding fragment thereof. In some embodiments, the BH3-containing proapoptotic protein can be, or contain, t-BID or a MUC1-binding fragment thereof. In some embodiments, the BH3-containing proapoptotic protein can be, or contain, BAX or a MUC1-binding fragment thereof. In some embodiments, the BH3-containing proapoptotic protein can be, or contain, BIM or a MUC1-binding fragment thereof. In some embodiments, the BH3-containing proapoptotic protein can be, or contain, BAK or a MUC1-binding fragment thereof. In some embodiments, the MUC1 can be, or can contain, the cytoplasmic domain of MUC1 (MUC1-CD), e.g., the MUC1-CD as depicted in SEQ ID NO:2.

Also provided is a compound identified or generated by any of the preceding methods and pharmaceutical compositions which contain the compound(s).

Herein is featured a process of manufacturing a compound. The process includes the steps of: contacting a MUC1 reagent with a BH3-containing proapoptotic protein reagent in the presence of a candidate compound; determining whether the candidate compound inhibits binding of the MUC1 reagent to the BH3-containing proapoptotic reagent; and after determining that a compound inhibits the interaction between MUC1 and a BH3-containing proapoptotic protein, manufacturing the compound.

Also featured is an in vitro method of inhibiting an interaction between MUC1 and a BH3-containing proapoptotic protein, which method includes the steps of contacting (i) a MUC1 reagent; (ii) a BH3-containing proapoptotic protein reagent; or (iii) a molecular complex comprising (i) or (ii) with a compound that inhibits the interaction between MUC1 and a BH3-containing proapoptotic protein. The method can also include the step of determining whether inhibition of the interaction between MUC1 and the BH3-containing proapoptotic protein has occurred. The contacting can occur in a cell. The cell can be a human cell. The cell can be a cancer cell such as a lung cancer cell, a breast cancer cell, a colon cancer cell, a pancreatic cancer cell, a renal cancer cell, a stomach cancer cell, a liver cancer cell, a bone cancer cell, a hematological cancer cell, a neural tissue cancer cell, a melanoma cell, a thyroid cancer cell, an ovarian cancer cell, a testicular cancer cell, a prostate cancer cell, a cervical cancer cell, a vaginal cancer cell, a B cell lymphoma cell, or a bladder cancer cell. The MUC1 reagent can include the MUC1-CD, e.g., the MUC1-CD as depicted in SEQ ID NO:2. The compound can contain or be the MUC1 cytoplasmic domain, for example, the MUC1-CD as depicted in SEQ ID NO:2. In some embodiments, the BH3-containing proapoptotic protein reagent can be, or contain, BID or a MUC1-binding fragment thereof. In some embodiments, the BH3-containing proapoptotic protein reagent can be, or contain, t-BID or a MUC1-binding fragment thereof. In some embodiments, the BH3-containing proapoptotic protein reagent can be, or contain, BAX or a MUC1-binding fragment thereof. In some embodiments, the BH3-containing proapoptotic protein reagent can be, or contain, BIM or a MUC1-binding fragment thereof. In some embodiments, the BH3-containing proapoptotic protein reagent can be, or contain, BAK or a MUC1-binding fragment thereof. In some embodiments, the BH3-containing proapoptotic protein reagent can be, or contain, BAD or a MUC1-binding fragment thereof.

Also featured is an in vitro method of promoting apoptosis in a cell. The method includes the steps of: identifying a cell as one expressing a BH2-containing antiapoptotic protein; and contacting (i) a MUC1 reagent; (ii) a BH3-containing proapoptotic protein reagent; or (iii) a molecular complex comprising (i) or (ii) with a compound that inhibits the interaction between MUC1 and a BH3-containing proapoptotic protein, wherein the BH3-containing proapoptotic protein is capable of binding to the BH2-containing antiapoptotic protein. The method can also include the step of determining whether inhibition of the interaction between MUC1 and the BH3-containing proapoptotic protein has occurred. The method can also include the step of determining whether apoptosis occurred. The contacting can occur in a cell. The cell can be a human cell. The cell can be a cancer cell such as a lung cancer cell, a breast cancer cell, a colon cancer cell, a pancreatic cancer cell, a renal cancer cell, a stomach cancer cell, a liver cancer cell, a bone cancer cell, a hematological cancer cell, a neural tissue cancer cell, a melanoma cell, a thyroid cancer cell, an ovarian cancer cell, a testicular cancer cell, a prostate cancer cell, a cervical cancer cell, a vaginal cancer cell, a B cell lymphoma cell, or a bladder cancer cell. The MUC1 reagent can include the MUC1-CD, e.g., the MUC1-CD as depicted in SEQ ID NO:2. The compound can contain or be the MUC1 cytoplasmic domain, for example, the MUC1-CD as depicted in SEQ ID NO:2. In some embodiments, the BH3-containing proapoptotic protein reagent can be, or contain, BID or a MUC1-binding fragment thereof. In some embodiments, the BH3-containing proapoptotic protein reagent can be, or contain, t-BID or a MUC1-binding fragment thereof. In some embodiments, the BH3-containing proapoptotic protein reagent can be, or contain, BAX or a MUC1-binding fragment thereof. In some embodiments, the BH3-containing proapoptotic protein reagent can be, or contain, BIM or a MUC1-binding fragment thereof. In some embodiments, the BH3-containing proapoptotic protein reagent can be, or contain, BAK or a MUC1-binding fragment thereof. In some embodiments, the BH3-containing proapoptotic protein reagent can be, or contain, BAD or a MUC1-binding fragment thereof.

Also featured is an in vitro method of promoting apoptosis in a cell, which method includes the steps of: optionally identifying a cell as one expressing a BH3-containing proapoptotic protein; and culturing the cell with a compound that inhibits MUC1. The method can also include the steps of determining if inhibition of MUC1 has occurred. The method can also include the step of determining whether apoptosis occurred. Inhibition of MUC1 includes inhibition of MUC1 mRNA or MUC1 protein expression. Inhibition of MUC1 expression also can be increased degradation of MUC1 mRNA or MUC1 protein. Inhibition of MUC1 can be inhibition of MUC1 activity such as inhibition of an antiapoptotic activity of MUC1 (e.g., an interaction between MUC1 and a BH3-containing proapoptotic protein). The compound can be a compound that inhibits transcription of the MUC1 gene or can be a compound that inhibits translation of the MUC1 mRNA. The cell can be any of those described herein.

Also provided is an in vitro method of promoting apoptosis in a cell, the method includes the steps of: optionally identifying a cell as one expressing MUC1; and culturing the cell with an inhibitor of a BH2-containing antiapoptotic protein. The method can also optionally include the step of determining whether inhibition of a BH2-containing antiapoptotic protein occurred. The method can also include the step of determining whether apoptosis occurred. Inhibition of the expression of a BH2-containing antiapoptotic protein includes inhibition of the expression of a BH2-containing antiapoptotic protein mRNA or protein. Inhibition of the expression of a BH2-containing antiapoptotic protein also includes increased degradation of a BH2-containing antiapoptotic protein mRNA or protein. Inhibition of a BH2-containing protein can also be inhibition of an activity of BH2-containing antiapoptotic protein such as an antiapoptotic activity. The compound can be a compound that inhibits transcription of a BH2-containing antiapoptotic protein-encoding gene or can be a compound that inhibits translation of a BH2-containing antiapoptotic protein mRNA. The cell can be any of those described herein. The BH2-containing antiapoptotic protein can be Bcl-2 or any of those described herein.

Herein is also featured an in vivo method of inhibiting an interaction between MUC1 and a BH3-containing proapoptotic protein. The method includes the steps of: optionally identifying a subject as one having, or suspected of having (or at risk of developing), a cancer containing one or more cells expressing MUC1 and delivering to a subject a compound that inhibits the interaction between MUC1 and a BH3-containing proapoptotic protein. The method can also include the step of determining whether the one or more cancer cells of the subject's cancer express MUC1. The method can also include the step of determining whether inhibition of the interaction between MUC1 and a BH3-containing proapoptotic protein has occurred. In some embodiments, the BH3-containing proapoptotic protein can be, or contain, BID or a MUC1-binding fragment thereof. In some embodiments, the BH3-containing proapoptotic protein can be, or contain, t-BID or a MUC1-binding fragment thereof. In some embodiments, the BH3-containing proapoptotic protein can be, or contain, BAX or a MUC1-binding fragment thereof. In some embodiments, the BH3-containing proapoptotic protein can be, or contain, BIM or a MUC1-binding fragment thereof. In some embodiments, the BH3-containing proapoptotic protein can be, or contain, BAK or a MUC1-binding fragment thereof. In some embodiments, the BH3-containing proapoptotic protein can be, or contain, BAD or a MUC1-binding fragment thereof. In some embodiments, the MUC1 can be, or can contain, the cytoplasmic domain of MUC1 (MUC1-CD), e.g., the MUC1-CD having the SEQ ID NO:2. The subject can be any mammal, e.g., a human (e.g., a human patient) or a non-human primate (e.g., chimpanzee, baboon, or monkey), a mouse, a rat, a rabbit, a guinea pig, a gerbil, a hamster, a horse, a type of livestock (e.g., cow, pig, sheep, or goat), a dog, a cat, or a whale. The cancer can be any of those described herein (see below).

As used herein, a subject "at risk of developing a cancer" is a subject that: (a) has a predisposition to develop a cancer, i.e., a genetic predisposition to develop cancer such as a mutation in a tumor suppressor gene (e.g., mutation in BRCA1, p53, RB, or APC); or (b) has been exposed to conditions that can result in cancer. Thus, a subject can be one "at risk of developing a cancer" when the subject has been exposed to mutagenic or carcinogenic levels of certain compounds (e.g., carcinogenic compounds in cigarette smoke such as Acrolein, 4-Aminobiphenyl, Aromatic Amines, Aromatic Nitrohydrocarbons, Arsenic, Benzene, Benz{a}anthracene, Benzo{a}pyrene, Benzo {b}fluoranthene, Benzo {c}phenanthrene, Benzo{e}pyrene, Benzo{j}fluoranthene, Cadmium, Chromium, Chrysene, Dibenz{a,j}acridine, Dibenz{a,c}anthracene, Dibenz{a,h}acridine, Dibenzo{a, h}pyrene, Dibenzo{a,i}pyrene, Dibenzo{c,g}carbazole, Dichlorostilbene, 4-Ethycatechol, Formaldehyde, Hydrazine, Indeno{1,2,3-cd}pyrene, Methylchrysene, Methylfluoranthene, Methylnaphtalenes, 1-Methylindoles, 3-Methylcatechol, 4-Methylcatechol, 4-Methylcatechol, 4(methylnitrosamino)-1-(3-pyridyl)-butanone, 2-Naphthylamine, Nickel, Nitropropane, Nitrosodimethylamine, Nitrosoethymethylamine, Nitrosodiethylamine, Nitrosodi-n-propylamine, Nitrosodi-n-butylamine, Nitrosopyrrolidine, Nitrosopiperidine, Nitrosomorpholine, N'-Nitrosonomicotine, N'-Nitrosoanabasine, N'-Nitrosoanatabine, Polonium-210 (Radon), Urethane, or Vinyl Chloride). Moreover, the subject can be "at risk of developing a cancer" when the subject has been exposed to, e.g., large doses of ultraviolet light or X-irradiation, or exposed (e.g., infected) to a tumor-causing/associated virus such as papillomavirus, Epstein-Barr virus, hepatitis B virus, or human T-cell leukemia-lymphoma virus. From the above it will be clear that subjects "at risk of developing a cancer" are not all the subjects within a species of interest.

A subject "suspected of having a cancer" is one having one or more symptoms of a cancer. Symptoms of cancer are well-known to those of skill in the art and include, without limitation, breast lumps, nipple changes, breast cysts, breast pain, death, weight loss, weakness, excessive fatigue, difficulty eating, loss of appetite, chronic cough, worsening breathlessness, coughing up blood, blood in the urine, blood in stool, nausea, vomiting, liver metastases, lung metastases, bone metastases, abdominal fullness, bloating, fluid in peritoneal cavity, vaginal bleeding, constipation, abdominal distension, perforation of colon, acute peritonitis (infection, fever, pain), pain, vomiting blood, heavy sweating, fever, high blood pressure, anemia, diarrhea, jaundice, dizziness, chills, muscle spasms, colon metastases, lung metastases, bladder metastases, liver metastases, bone metastases, kidney metastases, and pancreas metastases, difficulty swallowing, and the like. Types of cancers can include, e.g., lung cancer, breast cancer, colon cancer, pancreatic cancer, renal cancer, stomach cancer, liver cancer, bone cancer, hematological cancer, neural tissue cancer, melanoma, thyroid cancer, ovarian cancer, testicular cancer, prostate cancer, cervical cancer, vaginal cancer, and bladder cancer.

Herein is also featured an in vivo method of inhibiting an interaction between MUC1 and a BH3-containing proapoptotic protein. The method includes the steps of: optionally identifying a subject as one having, or suspected of having, or at risk of developing, an inflammatory condition mediated by one or more inflammatory cells expressing MUC1 and delivering to a subject a compound that inhibits the interaction between MUC1 and a BH3-containing proapoptotic protein. The method can also include the step of determining whether the one or more inflammatory cells express MUC1. The method can also include the step of determining whether inhibition of the interaction between MUC1 and a BH3-containing proapoptotic protein has occurred. In some embodiments, the BH3-containing proapoptotic protein can be, or contain, BID or a MUC1-binding fragment thereof. In some embodiments, the BH3-containing proapoptotic protein can be, or contain, t-BID or a MUC1-binding fragment thereof. In some embodiments, the BH3-containing proapoptotic protein can be, or contain, BAX or a MUC1-binding fragment thereof. In some embodiments, the BH3-containing proapoptotic protein can be, or contain, BIM or a MUC1-binding fragment thereof. In some embodiments, the BH3-containing proapoptotic protein can be, or contain, BAK or a MUC1-binding fragment thereof. In some embodiments, the BH3-containing proapoptotic protein can be, or contain, BAD or a MUC1-binding fragment thereof. In some embodiments, the MUC1 can be, or can contain, the cytoplasmic domain of MUC1 (MUC1-CD), e.g., the MUC1-CD having the SEQ ID NO:2. The subject can be any of those described herein. The inflammatory condition can be any of those described herein (see below).

A subject "at risk of developing an inflammatory condition" refers to a subject with a family history of one or more inflammatory conditions (e.g., a genetic predisposition to one or more inflammatory conditions) or one exposed to one or more inflammation-inducing conditions. For example, a subject can have been exposed to a viral or bacterial superantigen such as, but not limited to, staphylococcal enterotoxins (SEs), a *streptococcus* pyogenes exotoxin (SPE), a *staphylococcus aureus* toxic shock-syndrome toxin (TSST-1), a streptococcal mitogenic exotoxin (SME) and a streptococcal superantigen (SSA). From the above it will be clear that subjects "at risk of developing an inflammatory condition" are not all the subjects within a species of interest.

A subject "suspected of having an inflammatory condition" is one who presents with one or more symptoms of an inflammatory condition. Symptoms of inflammatory conditions are well known in the art and include, but are not limited to, redness, swelling (e.g., swollen joints), joints that are warm to the touch, joint pain, stiffness, loss of joint function, fever, chills, fatigue, loss of energy, headaches, loss of appetite, muscle stiffness, insomnia, itchiness, stuffy nose, sneezing, coughing, one or more neurologic symptoms such as dizziness, seizures, or pain. An "inflammatory condition," as used herein, refers to a process in which one or more substances (e.g., substances not naturally occurring in the subject), via the action of white blood cells (e.g., B cells, T cells, macrophages, monocytes, or dendritic cells) inappropriately trigger a pathological response, e.g., a pathological immune response. Accordingly, such cells involved in the inflammatory response are referred to as "inflammatory cells." The inappropriately triggered inflammatory response can be one where no foreign substance (e.g., an antigen, a virus, a bacterium, a fungus) is present in or on the subject. The inappropriately triggered response can be one where a self-component (e.g., a self-antigen) is targeted (e.g., an autoimmune disorder such as multiple sclerosis). The inappropriately triggered response can also be an response that is inappropriate in magnitude or duration, e.g., anaphylaxis. Thus, the inappropriately targeted response can be due to the presence of a microbial infection (e.g., viral, bacterial, or fungal). Types of inflammatory conditions (e.g., autoimmune disease) can include, but are not limited to, osteoarthritis, Rheumatoid arthritis (RA), spondyloarthropathies, POEMS syndrome, Crohn's disease, multicentric Castleman's disease, systemic lupus erythematosus (SLE), multiple sclerosis (MS), muscular dystrophy (MD), insulin-dependent diabetes mellitus (IDDM), dermatomyositis, polymyositis, inflammatory neuropathies such as Guillain Barre syndrome, vasculitis such as Wegener's granulomatous, polyarteritis nodosa, polymyalgia rheumatica, temporal arteritis, Sjogren's syndrome, Bechet's disease, Churg-Strauss syndrome, or Takayasu's arteritis. Also included in inflammatory conditions are certain types of allergies such as rhinitis, sinusitis, urticaria, hives, angioedema, atopic dermatitis, food allergies (e.g., a nut allergy), drug allergies (e.g., penicillin), insect allergies (e.g., allergy to a bee sting), or mastocytosis. Inflammatory conditions can also include asthma and ulcerative colitis.

Also featured is an in vivo method of promoting apoptosis in a cell, which method includes the steps of: optionally identifying a subject as one having, suspected of having (or at risk of developing), a cancer containing one or more cells expressing a BH3-containing proapoptotic protein; and delivering to the subject a compound that inhibits MUC1. The method can also include the step of determining whether the one or more cancer cells of the subject's cancer express MUC1. The method can also include the step of determining whether inhibition of MUC1 occurred. The method can also include the step of determining whether apoptosis occurred. Inhibition of MUC1 includes inhibition of MUC1 expression of activity as described above. The compound can be a compound that inhibits transcription of the MUC1 gene or can be a compound that inhibits translation of the MUC1 mRNA. The cancer can be any of the cancers described herein.

Also featured is an in vivo method of promoting apoptosis in a cell, which method includes the steps of: optionally identifying a subject as one having, suspected of having (or at risk of developing), an inflammatory condition mediated by one or more inflammatory cells expressing a BH3-containing proapoptotic protein; and delivering to the subject a compound that inhibits MUC1. The method can also include the step of determining whether the one or more inflammatory cells express MUC1. The method can also include the step of determining whether inhibition of MUC1 occurred. The method can also include the step of determining whether apoptosis occurred. Inhibition of MUC1 can be inhibition of MUC1 expression or activity as described above. The compound can be a compound that inhibits transcription of the MUC1 gene or can be a compound that inhibits translation of the MUC1 mRNA. The inflammatory condition can be any of those described herein.

Provided herein is an in vivo method of promoting apoptosis in a cell, which method includes the steps of: optionally identifying a subject as one having, suspected of having (or at risk of developing), a cancer comprising one or more cells expressing a BH2-containing antiapoptotic protein; and delivering to the subject a compound that inhibits the interaction between MUC1 and a BH3-containing proapoptotic protein, wherein the BH3-containing proapoptotic protein is capable of binding to the BH2-containing antiapoptotic protein. The method can also include the steps of determining whether the one or more cancer cells of the subject's cancer express MUC1. The method can also include the step of determining whether inhibition of the interaction between MUC1 and a BH3-containing proapoptotic protein occurred. The BH2-containing antiapoptotic proteins, BH3-containing proapoptotic proteins, and MUC1 proteins can be any of those described herein. The subject and cancers can be any of those described herein.

Provided herein is an in vivo method of promoting apoptosis in a cell, which method includes the steps of: optionally identifying a subject as one having, suspected of having, or at risk of developing, an inflammatory condition mediated by one or more inflammatory cells expressing a BH2-containing antiapoptotic protein; and delivering to the subject a compound that inhibits the interaction between MUC1 and a BH3-containing proapoptotic protein, wherein the BH3-containing proapoptotic protein is capable of binding to the BH2-containing antiapoptotic protein. The method can also include the steps of determining whether the one or more inflammatory cells express MUC1. The method can also include the step of determining whether inhibition of the interaction between MUC1 and a BH3-containing proapoptotic protein occurred. The method can also include the step of determining whether apoptosis occurred. The BH2-containing antiapoptotic proteins, BH3-containing proapoptotic proteins, and MUC1 proteins can be any of those described herein. The subject and inflammatory conditions can be any of those described herein.

Also featured is an in vivo method of promoting apoptosis in a cell, which method includes the steps of: optionally identifying a subject as having, suspected of having, or at risk of developing, a cancer containing one or more cells expressing MUC1; and delivering to the subject an inhibitor of a BH2-containing antiapoptotic protein. The method can also include the steps of determining whether the one or more cancer cells of the subject's cancer express MUC1. The method can also include the step of determining whether inhibition of the BH2-containing antiapoptotic protein occurred. The method can also include the step of determining whether apoptosis occurred. The BH2-containing antiapoptotic protein can be any of those described herein. Inhibition of a BH2-containing antiapoptotic protein can be inhibition of the activity (such as an antiapoptotic activity) or expression (mRNA or protein expression) of a BH2-containing antiapoptotic protein. The subject and cancers can be any of those described herein.

Also featured is an in vivo method of promoting apoptosis in a cell, which method can include the steps of: optionally identifying a subject as having, suspected of having (or a risk of developing) an inflammatory condition mediated by one or more inflammatory cells expressing MUC1; and delivering to the subject an inhibitor of a BH2-containing antiapoptotic protein. The method can also include the steps of determining whether the one or more inflammatory cells express MUC1. The method can also include the step of determining whether inhibition of the BH2-containing antiapoptotic protein occurred. The method can also include the step of determining whether apoptosis occurred. The BH2-containing antiapoptotic protein can be any of those described herein. Inhibition of a BH2-containing antiapoptotic protein can be inhibition of the activity or expression (mRNA or protein expression) of a BH2-containing antiapoptotic protein. The subject and inflammatory conditions can be any of those described herein.

In some embodiments of any of the in vivo methods described herein, the methods can also further include the step of: administering to the subject one or more additional therapeutic agents. The one or more additional therapeutic agents can be one or more chemotherapeutic agents, one or more forms of immunotherapy, one or more forms of ionizing radiation, one or more forms of a hormonal therapy, or a hyperthermotherapy. The one or more forms of ionizing radiation can be, for example, gamma-irradiation, X-irradiation, or beta-irradiation. The one or more chemotherapeutic agents can be, for example, cisplatin, carboplatin, procarbazine, mechlorethamine, cyclophosphamide, camptothecin, adriamycin, ifosfamide, melphalan, chlorambucil, bisulfan, nitrosurea, dactinomycin, daunorubicin, doxorubicin, bleomycin, plicomycin, mitomycin, etoposide, verampil, podophyllotoxin, tamoxifen, taxol, transplatinum, 5-fluorouracil, vincristin, vinblastin, methotrexate, or an analogue of any of the aforementioned. The one or more additional therapeutic agents can be inhibitors of human epidermal growth factor receptor 2 (HER2, ErbB2, or neu; hereinafter referred to as HER2) such as Herceptin, Iressa, Tarceva, Erbitux, Lapatinib, Sutent (sunitinib malate), or an analogue of any of the aforementioned. Where the condition to be treated is an inflammatory condition, the one or more therapeutic agents can be a non-steroidal anti-inflammatory drug (NSAID) such as a COX-2 inhibitor (e.g., aspirin, indomethacin, ibuprofen, naprozen, piroxican, nabumentone), a disease-modifying anti-rheumatic drug (DMARDS) (e.g., gold, hydroxychloroquine, penicillamine, sulfasalazine), a biological response modifier (e.g., an anti-TNF therapy such a soluble TNF receptor or an antibody that specifically binds to and inhibits TNF such as Humira (D2E7), Remicade (infliximab), or Enbrel (etanercept)), or a corticosteroid (e.g., Cortisone, Decadron, Delta-cortef, Deltasone, Dexamethasone, Hydrocortisone, Kenacort, Medrol, Methylprednisolone, Orasone, Prednisolone, Prednisone, Triamcinolone, Aristocort, Celestone, Cinalone, Depo-medrol, Hydeltrasol, Hydeltra TBA, Kenalog).

In any of the in vivo methods described herein, the compound can be any of the compounds described herein. The compound can be a small molecule, an antibody, an antibody fragment, a polypeptide, or a peptidomimetic.

In some embodiments of any of the in vivo methods, the delivery can involve administering to a subject one or more of any of the compounds described herein, e.g., a compound of the invention.

In some embodiments of any of the in vivo methods, where the compound is a polypeptide, the methods can involve administering to the subject a nucleic acid comprising a nucleotide sequence encoding the polypeptide, the nucleotide sequence being operably-linked to a transcriptional regulatory sequence. The nucleic acid can be in a recombinant cell transfected with the nucleic acid and secreting the polypeptide. The recombinant cell can be a transfected cell, or the progeny of a cell, made by transfecting a cell derived from the subject. The cell that is transfected can be obtained directly from the subject or can be the progeny of a cell obtained from the subject.

"Polypeptide" and "protein" are used interchangeably and mean any peptide-linked chain of amino acids, regardless of length or post-translational modification.

The MUC1, BH2-containing antiapoptotic proteins (e.g., Bcl-2, Bcl-xL, or Bcl-xES), or BH3-containing proapoptotic proteins (e.g., BID, BIM, BAX, BAD, BIK, NOXA, PUMA, BMF, BAK, or HRK) "reagents" used in any of the methods of the invention can contain, or be, wild-type, full-length, mature proteins or fragments (e.g., functional fragments) of such proteins. The reagents can also be variants of full-length, mature, wild-type proteins or fragments of the proteins having additions, deletions, or substitutions. Reagents with substitutions will generally have not more than 50 (e.g., not more than one, two, three, four, five, six, seven, eight, nine, ten, 12, 15, 20, 25, 30, 35, 40, or 50) conservative amino acid substitutions. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine.

Deletion variants can lack one, two, three, four, five, six, seven, eight, nine, ten, 11, 12, 13, 14, 15, 16, 17, 18, 19, or 20 amino acid segments (of two or more amino acids) or non-contiguous single amino acids.

Additions (addition variants) include full-length, wild-type, mature polypeptides or fragments with internal or terminal (C or N) irrelevant or heterologous amino acid sequences (i.e., sequences derived from other proteins or synthetic sequences not corresponding to any naturally occurring protein). The sequences can be, for example, an antigenic tag (e.g., FLAG, polyhistidine, hemaglutianin (HA), glutathione-S-transferase (GST), or maltose-binding protein (MBP)). Heterologous sequences can also be proteins useful as diagnostic or detectable markers, for example, luciferase, green fluorescent protein (GFP), or chloramphenicol acetyl transferase (CAT). Heterologous sequences can be of varying length and in some cases can be a larger sequences than the full-length, wild-type mature polypeptides of fragments (functional fragments) thereof.

A "fragment," as used herein, refers to a segment of the polypeptide that is shorter than a full-length, immature polypeptide. A "functional fragment" of a polypeptide has at least 25% (e.g., at least 25%, at least 30%, at least 35%, at least 40%, at least 50%, at least 55%, at least 60%, at least 70%, at least 80%, at least 90%, at least 95%, at least 98%, at least 99%, at least 99.5%, or 100% or more) of the activity of the mature, polypeptide (see above). Fragments of a polypeptide include terminal as well internal deletion variants of a polypeptide. The polypeptides, fragments, or their variants can be of any species expressing relevant forms of the wild-type, human proteins, such as e.g., nematode, insect, plant, bird, reptile, or mammal (e.g., a mouse, rat, dog, cat, goat, pig, cow, horse, whale, or monkey). All that is required is that such variants have at least 25% (e.g., at least: 30%; 40%; 50%; 60%; 70%; 75%; 80%; 85%; 90%; 95%; 97%; 98%; 99%; 99.5%, or 100% or even greater) of the activity of the wild-type, full-length, mature protein.

In the case of MUC1, the relevant activity is the ability to bind (interact) with a BH3-containing proapoptotic protein (e.g., BID, BIM, BAX, BAD, BIK, NOXA, PUMA, BMF, BAK, or HRK). This activity is also sometimes referred to as BH3-containing proapoptotic protein-binding activity.

In the case of a BH3-containing proapoptotic protein (e.g., BID, BIM, BAX, BAD, BIK, NOXA, PUMA, BMF, BAK, or HRK), the relevant activity is the ability to bind (interact) with MUC1 (or the MUC1-CD). This activity is thus sometimes referred to as MUC1-binding activity. In some embodiments, the relevant BH3-containing proapoptotic protein activity is the ability to bind to and/or inhibit a BH2-containing antiapoptotic protein (e.g., Bcl-2, Bcl-$x_L$, or Bcl-$x_S$. This BH3-containing proapoptotic protein activity is sometimes referred to as BH2-containing antiapoptotic-binding activity. It is understood that BH3-containing proapoptotic proteins include proteins containing only a BH3, herein referred to as "BH3-only proteins," such as BID, BIM, BAD, BIK, NOXA, PUMA, BMF, or HRK. BH3-containing proapoptotic proteins also include those proteins with additional Bcl-2 homology (BH) domains other than BH3's (e.g., BH1 or BH2), which proteins promote apoptosis when expressed in a cell. Examples of such multi-BH domain proapoptotic proteins include BAX and BAK.

Functional fragments of a BH3-containing proapoptotic protein can be, or include, a t-BID fragment of BID (e.g., the t-BID fragment having SEQ ID NO:7).

It is understood that the terms "BH3-containing proapoptotic proteins," "BID," "BIM," "BAX," "BAD," "NOXA," "BIK," "PUMA," "BMF," "BAK," or "HRK" refer to all forms (e.g., splice variants) of the proteins that bind to MUC1 (e.g., the MUC1-CD). Methods of testing for an interaction between MUC1 and a BH3-containing protein are known in the art and described in the Examples below.

As used herein, "operably linked" means incorporated into a genetic construct so that expression control sequences effectively control expression of a coding sequence of interest.

Unless otherwise defined, all technical and scientific terms used herein have the same meaning as commonly understood by one of ordinary skill in the art to which this invention pertains. Preferred methods and materials are describe below, although methods and materials similar or equivalent to those described herein can be used in the practice or testing of the present invention. All publications, patent applications, patents, and other references mentioned herein are incorporated by reference in their entirety. The materials, methods, and examples disclosed herein are illustrative only and not intended to be limiting.

Other features and advantages of the invention, e.g., methods of screening for inhibitors of an interaction between MUC1 and a BH3-containing proapoptotic protein, will be apparent from the following description, from the drawings and from the claims.

BRIEF DESCRIPTION OF THE DRAWINGS

FIG. 1C is a depiction of an exemplary amino acid sequence for human BID protein (SEQ ID NO:3). The underlined amino acid segment represents a "t-BID" fragment (SEQ ID NO:7) of BID.

FIG. 1D is a depiction of an exemplary amino acid sequence for human BIM protein (SEQ ID NO:4).

FIG. 2C is a depiction of an exemplary amino acid sequence for a human BAX protein (SEQ ID NO:5).

FIG. 2D is a depiction of an exemplary amino acid sequence for a human BAK protein (SEQ ID NO:6).

DESCRIPTION OF THE ILLUSTRATIVE EMBODIMENTS

Figure 1A:
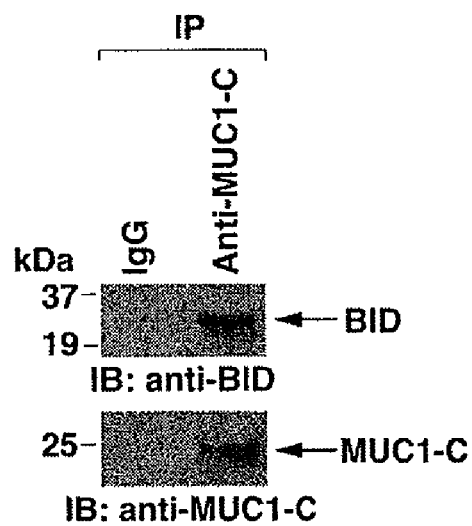
FIG. 1A is a pair of photographs of western blots depicting the association of MUC1 with BID. Whole-cell lysates were prepared from MCF7 cells and then subjected to immunoprecipitation (IP) using antibodies specific for MUC1 ("anti-MUC1-C") or an isotype non-specific control antibody ("IgG"). Immunoprecipitates were washed thoroughly, resuspended in Laemmli buffer and the immunoprecipitated proteins were resolved using sodium dodecyl sulfate polyacrylamide gel electrophoresis (SDS-PAGE). The various proteins were detected by western blot (immunoblot, "IB") using antibodies specific for MUC1-C and BID (top and bottom photographs respectively). The relative positions (e.g., the molecular weights) of the proteins are reported in kilodaltons (kDa) and indicated to the left of each of the immunoblots (e.g., 37 kDa or 19 kDa).

A. Methods of Screening for Inhibitory Compounds

MUC1-BH3-Containing Proapoptotic Protein Interactions. The present invention provides in vitro methods (e.g, "screening methods") for identifying compounds (e.g., small molecules or macromolecules) that inhibit binding of a BH3- containing proapoptotic protein (e.g., BAX, BAK, BIM, BID or a functional fragment of a BH3-containing proapoptotic protein) to MUC1, and in particular, the MUC1-CD.

These methods can be performed using: (a) isolated MUC1 reagents and one or more isolated BH3-containing proapoptotic protein reagents; or (b) cells expressing a MUC1 reagent and one or more BH3-containing proapoptotic protein reagents.

The term "isolated" as applied to any of the polypeptide reagents described herein refers to a polypeptide, or a peptide fragment thereof, which either has no naturally-occurring counterpart or has been separated or purified from components which naturally accompany it, e.g., in tissues such as pancreas, liver, spleen, ovary, testis, muscle, joint tissue, neural tissue, gastrointestinal tissue or tumor tissue (e.g., breast cancer or colon cancer tissue), or body fluids such as blood, serum, or urine. Typically, the polypeptide or peptide fragment is considered "isolated" when it is at least 70%, by dry weight, free from the proteins and other naturally-occurring organic molecules with which it is naturally associated. Preferably, a preparation of a reagent is at least 80%, more preferably at least 90%, and most preferably at least 99%, by dry weight, the reagent. Since a polypeptide that is chemically synthesized is, by its nature, separated from the components that naturally accompany it, a synthetic polypeptide reagent is "isolated."

An isolated polypeptide reagent can be obtained, for example, by extraction from a natural source (e.g., from tissues); by expression of a recombinant nucleic acid encoding the polypeptide; or by chemical synthesis. A polypeptide reagent that is produced in a cellular system different from the source from which it naturally originates is "isolated," because it will necessarily be free of components which naturally accompany it. The degree of isolation or purity can be measured by any appropriate method, e.g., column chromatography, polyacrylamide gel electrophoresis, or HPLC analysis.

Prior to testing, any of the reagents described herein can undergo modification, e.g., phosphorylation or glycosylation, by methods known in the art.

In methods of screening for compounds that inhibit binding of an isolated MUC1 reagent to an isolated BH3-containing proapoptotic protein reagent, a MUC1 reagent is contacted with a BH3-containing proapoptotic protein reagent in the presence of one or more concentrations of a test compound and binding between the two reagents in the presence and absence of the test compound is detected, tested for, and/or measured. In such assays neither of the reagents need be detectably labeled. For example, by exploiting the phenomenon of surface plasmon resonance, the MUC1 reagent can be bound to a suitable solid substrate and a BH3-containing proapoptotic protein reagent exposed to the substrate-bound MUC1 reagent in the presence and absence of the compound of interest. Binding of the BH3-containing proapoptotic protein reagent to the MUC1 reagent on the solid substrate results in a change in the intensity of surface plasmon resonance that can be detected qualitatively or quantitatively by an appropriate instrument, e.g., a Biacore apparatus (Biacore International AB, Rapsgatan, Sweden). It will be appreciated that the experiment can be performed in reverse, i.e., with the BH3-containing proapoptotic protein reagent bound to the solid substrate and the MUC1 reagent added to it in the presence of the test compound.

Moreover, assays to test for inhibition (or in some cases enhancement) of binding to MUC1 can involve the use, for example, of: (a) a single MUC1-specific "detection" antibody that is detectably labeled; (b) an unlabeled MUC1-specific antibody and a detectably labeled secondary antibody; or (c) a biotinylated MUC1-specific antibody and detectably labeled avidin. In addition, combinations of these approaches (including "multi-layer" assays) familiar to those in the art can be used to enhance the sensitivity of assays. In these assays, the BH3-containing proapoptotic protein (e.g., BID, BIM, BAK, or BAX) reagent can be immobilized on a solid substrate such as a nylon or nitrocellulose membrane by, for example, "spotting" an aliquot of a sample containing the reagent onto a membrane or by blotting onto a membrane an electrophoretic gel on which the sample or an aliquot of the sample has been subjected to electrophoretic separation. Alternatively, the BH3-containing proapoptotic protein reagent can be bound to a plastic substrate (e.g., the plastic bottom of an ELISA (enzyme-linked immunosorbent assay) plate well) using methods known in the art. The substrate-bound reagent is then exposed to the MUC1 reagent in the presence and absence of the test compound. After incubating the resulting mixture for a period of time and at temperature optimized for the system of interest, the presence and/or amount of MUC1 reagent bound to the BH3-containing proapoptotic protein test on the solid substrate is then assayed using a detection antibody that binds to the MUC1 reagent and, where required, appropriate detectably labeled secondary antibodies or avidin. It will be appreciated that instead of binding the BH3-containing proapoptotic protein reagent to the solid substrate, the MUC1 reagent can be bound to it. In this case binding of the BH3-containing proapoptotic protein reagent to the substrate-bound MUC1 is tested by obvious adaptations of the method described above for substrate-bound BH3-containing proapoptotic protein reagent.

The invention also features "sandwich" assays. In these sandwich assays, instead of immobilizing reagents on solid substrates by the methods described above, an appropriate reagent can be immobilized on the solid substrate by, prior to exposing the solid substrate to the reagent, conjugating a "capture" reagent-specific antibody (polyclonal or mAb) to the solid substrate by any of a variety of methods known in the art. The reagent is then bound to the solid substrate by virtue of its binding to the capture antibody conjugated to the solid substrate. The procedure is carried out in essentially the same manner described above for methods in which the appropriate reagent is bound to the solid substrate by techniques not involving the use of a capture antibody. It is understood that in these sandwich assays, the capture antibody should not bind to the same epitope (or range of epitopes in the case of a polyclonal antibody) as the detection antibody. Thus, if a mAb is used as a capture antibody, the detection antibody can be either: (a) another mAb that binds to an epitope that is either completely physically separated from or only partially overlaps with the epitope to which the capture mAb binds; or (b) a polyclonal antibody that binds to epitopes other than or in addition to that to which the capture mAb binds. On the other hand, if a polyclonal antibody is used as a capture antibody, the detection antibody can be either: (a) a mAb that binds to an epitope that is either completely physically separated from or partially overlaps with any of the epitopes to which the capture polyclonal antibody binds; or (b) a polyclonal antibody that binds to epitopes other than or in addition to that to which the capture polyclonal antibody binds. Assays which involve the use of a capture and a detection antibody include sandwich ELISA assays, sandwich Western blotting assays, and sandwich immunomagnetic detection assays.

Suitable solid substrates to which the capture antibody can be bound include, without limitation, the plastic bottoms and/or sides of wells of microtiter plates, membranes such as nylon or nitrocellulose membranes, polymeric (e.g., without limitation, agarose, cellulose, or polyacrylamide) beads or particles.

Methods of detecting and/or for quantifying a detectable label depend on the nature of the label and are known in the art. Appropriate labels include, without limitation, radionuclides (e.g., $^{125}$I, $^{131}$I, $^{35}$S, $^{3}$H, $^{32}$P, or $^{14}$C), fluorescent moieties (e.g., fluorescein, rhodamine, or phycoerythrin), luminescent moieties (e.g., Qdot™ nanoparticles supplied by the Quantum Dot Corporation, Palo Alto, Calif.), compounds that absorb light of a defined wavelength, or enzymes (e.g., alkaline phosphatase or horseradish peroxidase). The products of reactions catalyzed by appropriate enzymes can be, without limitation, fluorescent, luminescent, or radioactive or they may absorb visible or ultraviolet light. Examples of detectors include, without limitation, x-ray film, radioactivity counters, scintillation counters, spectrophotometers, colorimeters, fluorometers, luminometers, and densitometers.

Candidate compounds can also be tested for their ability to inhibit binding of MUC1 to a BH3-containing proapoptotic protein in cells. The cells can either naturally express an appropriate MUC1 reagent and/or a BH3-containing proapoptotic protein reagent of interest (i.e., the cells encode an endogenous MUC1 and/or a BH3-containing proapoptotic protein gene which can be expressed to yield a MUC1 and/or BH3-containing proapoptotic protein polypeptides or their functional fragments) or they can recombinantly express either or both reagents. The cells can be normal or malignant and of any histological type, e.g., without limitation, epithelial cells, fibroblasts, lymphoid cells, macrophages/monocytes, granulocytes, keratinocytes, neuronal cells, or muscle cells. Suitable cell lines include those recited in the examples, e.g., breast cancer or colon cancer cell lines. The test compound can be added to the solution (e.g., culture medium) containing the cells or, where the compound is a protein, the cells can recombinantly express it. The cells can optionally also be exposed to a stimulus of interest (e.g., exposure to an apoptosis inducing agent such as staurosporin or taxol) prior to or after exposure of the cells to the compound. Following incubation of cells expressing the reagents of interest in the absence or presence (optionally at various concentrations), physical association between the reagents can be determined microscopically using appropriately labeled antibodies specific for both reagents, e.g., by confocal microscopy. Alternatively, the cells can be lysed under non-dissociating conditions and the lysates tested for the presence of physically associated reagents. Such methods include adaptions of those described using isolated reagents. For example, an antibody specific for one of the two reagents (reagent 1) can be bound to a solid substrate (e.g., the bottom and sides of the well of a microtiter plate or a nylon membrane). After washing away unbound antibody, the solid substrate with bound antibody is contacted with the cell lysate. Any reagent 1 in the lysate, bound or not bound to the second reagent (reagent 2), will bind to the antibody specific for reagent 1 on the solid substrate. After washing away unbound lysate components, the presence of reagent 2 (bound via reagent 1 and the antibody specific for reagent 1 to the solid substrate) is tested for using a detectably labeled antibody (see above) specific for reagent 2. Alternatively, reagent 1 can be immunoprecipitated with an antibody specific for reagent 1 and the immunoprecipitated material can be subjected to electrophoretic separation (e.g., by polyacrylamide gel electrophoresis performed under non-dissociating conditions). The electrophoretic gel can then be blotted onto a membrane (e.g., a nylon or a nitrocellulose membrane) and any reagent 2 on the membrane detected and/or measured with a detectably labeled antibody (see above) specific for reagent 2 by any of the above-described methods. It is understood that in the above-described assays, reagent 1 can be either the MUC1 reagent or the BH3-containing proapoptotic protein reagent or vice versa. The test compounds can bind to one or both of the MUC1 and BH3-containing proapoptotic protein reagents.

Figures 3A, 3B:
FIG. 3A is a diagram depicting the domain structure of the human MUC1 cytoplasmic domain (MUC1-CD) (SEQ ID NO:2). The numbers above the diagram indicate amino acid position (1-72). Two fragments of MUC1-CD are indicated below the MUC1-CD amino acid sequence. These fragments are amino acids 1-40 and 46-72 of the MUC1-CD (as depicted in SEQ ID NO:2).
FIG. 3B depicts an exemplary amino acid sequence for a full-length, human MUC1 protein (SEQ ID NO:1).

Exemplary MUC1 reagents for use in the methods described above include MUC1 reagents that contain a MUC1-cytoplasmic domain (CD), e.g., the human MUC1-CD depicted by SEQ ID NO:2 (or a functional fragment of the MUC1-CD, see FIG. 3A).

B. Methods of Designing and Producing Inhibitory Compounds

Compounds that Inhibit MUC1-BH3-Containing Proapoptotic Protein Interactions. The invention also relates to using MUC1 reagents and/or BH3-containing proapoptotic protein (e.g., BID, BAK, BAX, or BIM) reagents to predict or design compounds that can interact with MUC1 and/or a BH3-containing proapoptotic protein and potentially thereby inhibit the interaction between these two polypeptides. Such compounds would be useful to inhibit the ability of MUC1 to promote cell survival (e.g., through inhibition of MUC1 binding to and inhibition of a BH3-containing proapoptotic protein). One of skill in the art would know how to use standard molecular modeling or other techniques to identify small molecules that would bind to "appropriate sites" on MUC1 and/or a BH3-containing proapoptotic protein. Examples are provided in, e.g., Enyedy et al. (2001) J. Med. Chem. 44(25): 4313-4324; Degterev et al. (2001) Nat. Cell Biol. 3(2):173-182; and Broughton (1997) Curr. Opin. Chem. Biol. 1, 392-398. Examples of suitable starting structures for BH3-containing proapoptotic proteins include those described in, e.g., Liu et al. (2003) Immunity 19(3):341-352; Chou et al. (1999) Cell 96(5):615-625; and Sattler et al. (1997) Science 275(5302):983-986. Generally, an "appropriate site" on a MUC1 or a BH3-containing proapoptotic protein is a site directly involved in the physical interaction between the two molecule types. However, an "appropriate site" can also be an allosteric site, i.e., a region of the molecule not directly involved in a physical interaction with another molecule (and possibly even remote from such a "physical interaction" site) but to which binding of a compound results (e.g., by the induction of a conformational change in the molecule) in inhibition of the binding of the molecule to another molecule.

By "molecular modeling" is meant quantitative and/or qualitative analysis of the structure and function of protein-protein physical interaction based on three-dimensional structural information and protein-protein interaction models. This includes conventional numeric-based molecular dynamic and energy minimization models, interactive computer graphic models, modified molecular mechanics models, distance geometry and other structure-based constraint models. Molecular modeling typically is performed using a computer and may be further optimized using known methods.

Methods of designing compounds that bind specifically (e.g., with high affinity) to the region of MUC1 that interacts with a BH3-containing proapoptotic protein (i.e., the cytoplasmic domain of MUC1) or the region of a BH3-containing proapoptotic protein that binds to MUC1 typically are also computer-based, and involve the use of a computer having a program capable of generating an atomic model. Computer programs that use X-ray crystallography data are particularly useful for designing such compounds. Programs such as RasMol, for example, can be used to generate a three dimensional model of, e.g., the region of MUC1 that interacts with an BH3-containing proapoptotic protein (e.g., BID, BIM, BAK, or BAX) or the region of a BH3-containing proapoptotic protein that binds to MUC1 and/or determine the structures involved in MUC1-BH3-containing proapoptotic protein binding. Computer programs such as INSIGHT (Accelrys, Burlington, Mass.), GRASP (Anthony Nicholls, Columbia University), Dock (Molecular Design Institute, University of California at San Francisco), and Auto-Dock (Accelrys) allow for further manipulation and the ability to introduce new structures. Compounds can be designed using, for example, computer hardware or software, or a combination of both. However, designing is preferably implemented in one or more computer programs executing on one or more programmable computers, each containing a processor and at least one input device. The computer(s) preferably also contain(s) a data storage system (including volatile and non-volatile memory and/or storage elements) and at least one output device. Program code is applied to input data to perform the functions described above and generate output information. The output information is applied to one or more output devices in a known fashion. The computer can be, for example, a personal computer, microcomputer, or work station of conventional design.

Each program is preferably implemented in a high level procedural or object oriented programming language to communicate with a computer system. However, the programs can be implemented in assembly or machine language, if desired. In any case, the language can be a compiled or interpreted language.

Each computer program is preferably stored on a storage media or device (e.g., ROM or magnetic diskette) readable by a general or special purpose programmable computer. The computer program serves to configure and operate the computer to perform the procedures described herein when the program is read by the computer. The method of the invention can also be implemented by means of a computer-readable storage medium, configured with a computer program, where the storage medium so configured causes a computer to operate in a specific and predefined manner to perform the functions described herein.

For example, the computer-requiring steps in a method of designing a compound can involve:

(a) inputting into an input device, e.g., through a keyboard, a diskette, or a tape, data (e.g. atomic coordinates) that define the three-dimensional (3-D) structure of a first molecule (e.g., MUC1 or a part of MUC1 such as the MUC1-CD) that is known to, or is predicted to, bind to a second molecule (e.g., a BH3-containing proapoptotic protein (e.g., BAX, BAK, BID, or BIM) or a part thereof) or a molecular complex (e.g., MUC1, or a part thereof, bound to a BH3-containing proapoptotic protein), or a part thereof, or MUC1 bound to, or predicted to bind to, a macromolecular BH3-containing proapoptotic protein complex), e.g., a region of MUC1 that interacts with a BH3-containing proapoptotic protein (i.e., the cytoplasmic domain of MUC1), the region of a BH3-containing proapoptotic protein that binds to MUC1, or all or a part (e.g., the cytoplasmic domain) of MUC1 that is, or is predicted to be, bound to all or a part of a BH3-containing proapoptotic protein (e.g., BAX, BAK, BID, or BIM); and (b) determining, using a processor, the 3-D structure (e.g., an atomic model) of: (i) the site on the first molecule involved in, or predicted to be involved in, binding to the second molecule; or (ii) one or more sites on the molecular components of molecular complex of interaction between molecular components of the molecular complex.

From the information obtained in this way, one skilled in the art will be able to design and make inhibitory compounds (e.g., peptides, non-peptide small molecules, aptamers (e.g., nucleic acid aptamers) with the appropriate 3-D structure (see "Methods of Making Inhibitory Compounds and Proteins Useful for the Invention" below).

Moreover, if computer-usable 3-D data (e.g., x-ray crystallographic or nuclear magnetic resonance (NMR) data) for a candidate compound are available, the following computer-based steps can be performed in conjunction with computer-based steps (a) and (b) described above: (c) inputting into an input device, e.g., through a keyboard, a diskette, or a tape, data (e.g. atomic coordinates) that define the three-dimensional (3-D) structure of a candidate compound; (d) determining, using a processor, the 3-D structure (e.g., an atomic model) of the candidate compound; (e) determining, using the processor, whether the candidate compound binds to the site on the first molecule or the one or more sites on the molecular components of the molecular complex; and (f) identifying the candidate compound as a compound that inhibits the interaction between the first and second molecule or the between the molecular components of the molecular complex.

The method can involve the additional step of outputting to an output device a model of the 3-D structure of the compound. In addition, the 3-D data of candidate compounds can be compared to a computer database of, for example, 3-D structures (e.g., of MUC1, the cytoplasmic domain of MUC1, a BH3-containing proapoptotic protein, or a MUC1-binding fragment of a BH3-containing proapoptotic protein) stored in a data storage system.

Compounds useful for the invention also may be interactively designed from structural information of the compounds described herein using other structure-based design/modeling techniques (see, e.g., Jackson (1997) Seminars in Oncology 24:L164-172; and Jones et al. (1996) J. Med. Chem. 39:904-917). Compounds and polypeptides of the invention also can be identified by, for example, identifying candidate compounds by computer modeling as fitting spatially and preferentially (i.e., with high affinity) into the appropriate acceptor sites on MUC1 or a BH3-containing proapoptotic protein (e.g., BIM, BAK, BID, or BAX).

Candidate compounds identified as described above can then be tested in standard cellular or cell-free binding or binding inhibition assays familiar to those skilled in the art. Exemplary assays are described herein.

A candidate compound whose presence requires at least 2-fold (e.g., 4-fold, 6-fold, 10-fold, 100-fold, 1000-fold, 10,000 fold, or 100,000-fold) more of a given MUC1 reagent to achieve a defined arbitrary level of binding to a fixed amount of a BH3-containing proapoptotic protein reagent than is achieved in the absence of the compound can be useful for inhibiting the interaction between MUC1 and the relevant BH3-containing proapoptotic protein, and thus can be useful as a cancer therapeutic or prophylactic agent. Alternatively, a candidate compound whose presence requires at least 2-fold (e.g., 2-fold, 4-fold, 6-fold, 10-fold, 100-fold, 1000-fold, 10,000 fold, or 100,000-fold) more of a given BH3-containing proapoptotic protein reagent to achieve a defined arbitrary level of binding to a fixed amount of a MUC1 reagent than is achieved in the absence of the compound can be useful for inhibiting the interaction between MUC1 and the relevant BH3-containing proapoptotic protein, and thus can be useful as a cancer therapeutic or prophylactic agent.

The 3-D structure of biological macromolecules (e.g., proteins, nucleic acids, carbohydrates, and lipids) can be determined from data obtained by a variety of methodologies. These methodologies, which have been applied most effectively to the assessment of the 3-D structure of proteins, include: (a) x-ray crystallography; (b) nuclear magnetic resonance (NMR) spectroscopy; (c) analysis of physical distance constraints formed between defined sites on a macromolecule, e.g., intramolecular chemical crosslinks between residues on a protein (e.g., International Patent Application No. PCT/US00/14667, the disclosure of which is incorporated herein by reference in its entirety), and (d) molecular modeling methods based on a knowledge of the primary structure of a protein of interest, e.g., homology modeling techniques, threading algorithms, or ab initio structure modeling using computer programs such as MONSSTER (Modeling Of New Structures from Secondary and Tertiary Restraints) (see, e.g., International Application No. PCT/US99/11913, the disclosure of which is incorporated herein by reference in its entirety). Other molecular modeling techniques may also be employed in accordance with this invention [e.g., Cohen et al. (1990) J. Med. Chem. 33: 883-894; Navia et al (1992) Current Opinions in Structural Biology, 2, pp. 202-210, the disclosures of which are incorporated herein by reference in its entirety]. All these methods produce data that are amenable to computer analysis. Other spectroscopic methods that can also be useful in the method of the invention, but that do not currently provide atomic level structural detail about biomolecules, include circular dichroism and fluorescence and ultraviolet/visible light absorbance spectroscopy. A preferred method of analysis is x-ray crystallography. Descriptions of this procedure and of NMR spectroscopy are provided below.

X-Ray Crystallography

X-ray crystallography is based on the diffraction of x-radiation of a characteristic wavelength by electron clouds surrounding the atomic nuclei in a crystal of a molecule or molecular complex of interest. The technique uses crystals of purified biological macromolecules or molecular complexes (but these frequently include solvent components, co-factors, substrates, or other ligands) to determine near atomic resolution of the atoms making up the particular biological macromolecule. A prerequisite for solving 3-D structure by x-ray crystallography is a well-ordered crystal that will diffract x-rays strongly. The method directs a beam of x-rays onto a regular, repeating array of many identical molecules so that the x-rays are diffracted from the array in a pattern from which the structure of an individual molecule can be retrieved. Well-ordered crystals of, for example, globular protein molecules are large, spherical or ellipsoidal objects with irregular surfaces. The crystals contain large channels between the individual molecules. These channels, which normally occupy more than one half the volume of the crystal, are filled with disordered solvent molecules, and the protein molecules are in contact with each other at only a few small regions. This is one reason why structures of proteins in crystals are generally the same as those of proteins in solution.

Methods of obtaining the proteins of interest are described below. The formation of crystals is dependent on a number of different parameters, including pH, temperature, the concentration of the biological macromolecule, the nature of the solvent and precipitant, as well as the presence of added ions or ligands of the protein. Many routine crystallization experiments may be needed to screen all these parameters for the combinations that give a crystal suitable for x-ray diffraction analysis. Crystallization robots can automate and speed up work of reproducibly setting up a large number of crystallization experiments (see, e.g., U.S. Pat. No. 5,790,421, the disclosure of which is incorporated herein by reference in its entirety). Polypeptide crystallization occurs in solutions in which the polypeptide concentration exceeds it's solubility maximum (i.e., the polypeptide solution is supersaturated). Such solutions may be restored to equilibrium by reducing the polypeptide concentration, preferably through precipitation of the polypeptide crystals. Often polypeptides may be induced to crystallize from supersaturated solutions by adding agents that alter the polypeptide surface charges or perturb the interaction between the polypeptide and bulk water to promote associations that lead to crystallization.

Crystallizations are generally carried out between 4° C. and 20° C. Substances known as "precipitants" are often used to decrease the solubility of the polypeptide in a concentrated solution by forming an energetically unfavorable precipitating depleted layer around the polypeptide molecules [Weber (1991) Advances in Protein Chemistry, 41:1-36]. In addition to precipitants, other materials are sometimes added to the polypeptide crystallization solution. These include buffers to adjust the pH of the solution and salts to reduce the solubility of the polypeptide. Various precipitants are known in the art and include the following: ethanol, 3-ethyl-2-4 pentanediol, and many of the polyglycols, such as polyethylene glycol (PEG). The precipitating solutions can include, for example, 13-24% PEG 4000, 5-41% ammonium sulfate, and 1.0-1.5 M sodium chloride, and a pH ranging from 5-7.5. Other additives can include 0.1 M HEPES, 2-4% butanol, 0.1 M or 20 mM sodium acetate, 50-70 mM citric acid, 120-130 mM sodium phosphate, 1 mM ethylene diamine tetraacetic acid (EDTA), and 1 mM dithiothreitol (DTT). These agents are prepared in buffers and are added dropwise in various combinations to the crystallization buffer.

Commonly used polypeptide crystallization methods include the following techniques: batch, hanging drop, seed initiation, and dialysis. In each of these methods, it is important to promote continued crystallization after nucleation by maintaining a supersaturated solution. In the batch method, polypeptide is mixed with precipitants to achieve supersaturation, and the vessel is sealed and set aside until crystals appear. In the dialysis method, polypeptide is retained in a sealed dialysis membrane that is placed into a solution containing precipitant. Equilibration across the membrane increases the polypeptide and precipitant concentrations, thereby causing the polypeptide to reach supersaturation levels.

In the preferred hanging drop technique [McPherson (1976) J. Biol. Chem., 251:6300-6306], an initial polypeptide mixture is created by adding a precipitant to a concentrated polypeptide solution. The concentrations of the polypeptide and precipitants are such that, in this initial form, the polypeptide does not crystallize. A small drop of this mixture is placed on a glass slide that is inverted and suspended over a reservoir of a second solution. The system is then sealed. Typically, the second solution contains a higher concentration of precipitant or other dehydrating agent. The difference in the precipitant concentrations causes the protein solution to have a higher vapor pressure than the second solution. Since the system containing the two solutions is sealed, an equilibrium is established, and water from the polypeptide mixture transfers to the second solution. This equilibrium increases the polypeptide and precipitant concentration in the polypeptide solution. At the critical concentration of polypeptide and precipitant, a crystal of the polypeptide may form.

Another method of crystallization introduces a nucleation site into a concentrated polypeptide solution. Generally, a concentrated polypeptide solution is prepared and a seed crystal of the polypeptide is introduced into this solution. If the concentrations of the polypeptide and any precipitants are correct, the seed crystal will provide a nucleation site around which a larger crystal forms.

Yet another method of crystallization is an electrocrystallization method in which use is made of the dipole moments of protein macromolecules that self-align in the Helmholtz layer adjacent to an electrode (see, e.g., U.S. Pat. No. 5,597,457, the disclosure of which is incorporated herein by reference in its entirety).

Some proteins may be recalcitrant to crystallization. However, several techniques are available to the skilled artisan to induce crystallization. For example, the removal of flexible polypeptide segments at the amino or carboxyl terminal end of the protein may facilitate production of crystalline protein samples. Removal of such segments can be done using molecular biology techniques or treatment of the protein with proteases such as trypsin, chymotrypsin, or subtilisin.

In diffraction experiments, a narrow and parallel beam of x-rays is taken from the x-ray source and directed onto the crystal to produce diffracted beams. The incident primary beams cause damage to both the macromolecule and solvent molecules. The crystal is, therefore, cooled (e.g., to –220° C. to –50° C.) to prolong its lifetime. The primary beam must strike the crystal from many directions to produce all possible diffraction spots, so the crystal is rotated in the beam during the experiment. The diffracted spots are recorded on a film or by an electronic detector. Exposed film has to be digitized and quantified in a scanning device, whereas the electronic detectors feed the signals they detect directly into a computer. Electronic area detectors significantly reduce the time required to collect and measure diffraction data. Each diffraction beam, which is recorded as a spot on film, is defined by three properties: the amplitude, which is measured from the intensity of the spot; the wavelength, which is set by the x-ray source; and the phase, which is lost in x-ray experiments. All three properties are needed for all of the diffracted beams in order to determine the positions of the atoms giving rise to the diffracted beams. One way of determining the phases is called Multiple Isomorphous Replacement (MIR), which requires the introduction of exogenous x-ray scatterers (e.g., heavy atoms such metal atoms) into the unit cell of the crystal. For a more detailed description of MIR, see U.S. Pat. No. 6,093,573 (column 15) the disclosure of which is incorporated herein by reference in its entirety.

Atomic coordinates refer to Cartesian coordinates (x, y, and z positions) derived from mathematical equations involving Fourier synthesis of data derived from patterns obtained via diffraction of a monochromatic beam of x-rays by the atoms (scattering centers) of biological macromolecule of interest in crystal form. Diffraction data are used to calculate electron density maps of repeating units in the crystal (unit cell). Electron density maps are used to establish the positions (atomic coordinates) of individual atoms within a crystal's unit cell. The absolute values of atomic coordinates convey spatial relationships between atoms because the absolute values ascribed to atomic coordinates can be changed by rotational and/or translational movement along x, y, and/or z axes, together or separately, while maintaining the same relative spatial relationships among atoms. Thus, a biological macromolecule (e.g., a protein) whose set of absolute atomic coordinate values can be rotationally or translationally adjusted to coincide with a set of prior determined values from an analysis of another sample is considered to have the same atomic coordinates as those obtained from the other sample.

Further details on x-ray crystallography can be obtained from co-pending U.S. application Ser. No. 10/486,278, U.S. Pat. No. 6,093,573 and International Application Nos. PCT/US99/18441, PCT/US99/11913, and PCT/US00/03745. The disclosures of all these patent documents are incorporated herein by reference in their entirety.

NMR Spectroscopy

While x-ray crystallography requires single crystals of a macromolecule of interest, NMR measurements are carried out in solution under near physiological conditions. However, NMR-derived structures are not as detailed as crystal-derived structures.

While the use of NMR spectroscopy was until relatively recently limited to the elucidation of the 3-D structure of relatively small molecules (e.g., proteins of 100-150 amino acid residues), recent advances including isotopic labeling of the molecule of interest and transverse relaxation-optimized spectroscopy (TROSY) have allowed the methodology to be extended to the analysis of much larger molecules, e.g., proteins with a molecular weight of 110 kDa [Wider (2000) BioTechniques, 29:1278-1294].

NMR uses radio-frequency radiation to examine the environment of magnetic atomic nuclei in a homogeneous magnetic field pulsed with a specific radio frequency. The pulses perturb the nuclear magnetization of those atoms with nuclei of nonzero spin. Transient time domain signals are detected as the system returns to equilibrium. Fourier transformation of the transient signal into a frequency domain yields a one-dimensional NMR spectrum. Peaks in these spectra represent chemical shifts of the various active nuclei. The chemical shift of an atom is determined by its local electronic environment. Two-dimensional NMR experiments can provide information about the proximity of various atoms in the structure and in three dimensional space. Protein structures can be determined by performing a number of two- (and sometimes 3- or 4-) dimensional NMR experiments and using the resulting information as constraints in a series of protein folding simulations.

More information on NMR spectroscopy including detailed descriptions of how raw data obtained from an NMR experiment can be used to determine the 3-D structure of a macromolecule can be found in: Protein NMR Spectroscopy, Principles and Practice, J. Cavanagh et al., Academic Press, San Diego, 1996; Gronenborn et al. (1990) Anal. Chem. 62(1):2-15; and Wider (2000), supra., the disclosures of all of which are incorporated herein by reference in their entirety Any available method can be used to construct a 3-D model of a region of MUC1 and/or a BH3-containing proapoptotic protein (e.g., BAX, BAK, BIM, or BID) of interest from the x-ray crystallographic and/or NMR data using a computer as described above. Such a model can be constructed from analytical data points inputted into the computer by an input device and by means of a processor using known software packages, e.g., HKL, MOSFILM, XDS, CCP4, SHARP, PHASES, HEAVY, XPLOR, TNT, NMRCOMPASS, NMRPIPE, DIANA, NMRDRAW, FELIX, VNMR, MADIGRAS, QUANTA, BUSTER, SOLVE, O, FRODO, or CHAIN. The model constructed from these data can be visualized via an output device of a computer, using available systems, e.g., Silicon Graphics, Evans and Sutherland, SUN, Hewlett Packard, Apple Macintosh, DEC, IBM, or Compaq.

C. Compounds

Compounds identified in any of the methods described herein, or any compound with appropriate activity useful in any of the methods described herein, include various chemical classes. Compounds can be biomolecules including, but not limited to, peptides, polypeptides, peptidomimetics (e.g., peptoids), amino acids, amino acid analogs, saccharides, fatty acids, steroids, purines, pyrimidines, derivatives or structural analogues thereof, polynucleotides, and polynucleotide analogs. Compounds can be both small or large molecule compounds.

Typically small molecule compounds are relatively small organic molecules having a molecular weight in the range of about 50 to 2,500 daltons. These compounds can comprise functional groups necessary for structural interaction with proteins (e.g., hydrogen bonding), and can include at least an amine, carbonyl, hydroxyl, or carboxyl group, and preferably at least two of the functional chemical groups. These compounds can often comprise cyclical carbon or heterocyclic structures and/or aromatic or polyaromatic structures (e.g., purine core) substituted with one or more of the above functional groups.

Also of interest as small molecule compounds in some of the methods described herein are nucleic acid aptamers, which are relatively short nucleic acid (DNA, RNA or a combination of both) sequences that bind with high avidity to a variety of proteins and inhibit the binding to such proteins of ligands, receptors, and other molecules. Aptamers are generally about 25-40 nucleotides in length and have molecular weights in the range of about 18-25 kDa. Aptamers with high specificity and affinity for targets can be obtained by an in vitro evolutionary process termed SELEX (systemic evolution of ligands by exponential enrichment) [see, for example, Zhang et al. (2004) Arch. Immunol. Ther. Exp. 52:307-315, the disclosure of which is incorporated herein by reference in its entirety]. For methods of enhancing the stability (by using nucleotide analogs, for example) and enhancing in vivo bioavailability (e.g., in vivo persistence in a subject's circulatory system) of nucleic acid aptamers see Zhang et al. (2004) and Brody et al. [(2000) Reviews in Molecular Biotechnology 74:5-13, the disclosure of which is incorporated herein by reference in its entirety].

Large molecule compounds can include large proteins such as antibodies (see below) or macromolecular complexes comprising two or more proteins.

Compounds can be identified from a number of potential sources, including: chemical libraries, natural product libraries, and combinatorial libraries comprised of random peptides, oligonucleotides, or organic molecules. Chemical libraries consist of random chemical structures, some of which are analogs of known compounds or analogs or compounds that have been identified as "hits" or "leads" in other drug discovery screens, while others are derived from natural products, and still others arise from non-directed synthetic organic chemistry. Natural product libraries are collections of microorganisms, animals, plants, or marine organisms which are used to create mixtures for screening by: (1) fermentation and extraction of broths from soil, plant or marine microorganisms, or (2) extraction of plants or marine organisms. Natural product libraries include polypeptides, non-ribosomal peptides, and variants (non-naturally occurring) thereof. For a review, see Science 282:63-68 (1998). Combinatorial libraries are composed of large numbers of peptides, oligonucleotides, or organic compounds as a mixture. These libraries are relatively easy to prepare by traditional automated synthesis methods, PCR, cloning, or proprietary synthetic methods. Of particular interest are non-peptide combinatorial libraries.

Still other libraries of interest include peptide, protein, peptidomimetic, multiparallel synthetic collection, recombinatorial, and polypeptide libraries. For a review of combinatorial chemistry and libraries created therefrom, see Myers, Curr. Opin. Bioechnol. 8:701-707 (1997).

Identification of test compounds through the use of the various libraries herein permits subsequent modification of the test compound "hit" or "lead" to optimize the capacity of the "hit" or "lead" to inhibit the interaction between, e.g., a BH3-containing proapoptotic protein and MUC1.

Inhibitory compounds can be large molecules such as antibodies, or antigen-binding antibody fragments, specific for, e.g., MUC1 or a BH3-containing proapoptotic protein. Such antibodies and fragments will generally bind to, or close to: (a) the region of MUC1 to which a BH3-containing proapoptotic protein (e.g., BAK, BAX, BIM, or BID) binds (e.g., MUC1-CD); or (b) the region on a BH3-containing proapoptotic protein to which MUC1 binds. However, as indicated above, the compounds can also act allosterically and so they can also bind to the proteins at positions other than, and even remote from, the binding sites for MUC1 (on a BH3-containing proapoptotic protein such as BAK, BAX, BIM or BID) and on a BH3-containing proapoptotic protein for MUC1 or a MUC1-CD. In embodiments of methods of inhibition of MUC1 and/or BH2-containing antiapoptotic expression, inhibitory antibodies can also bind to and/or antagonize, e.g., a cellular receptor that activates the expression of MUC1 and/or a BH2-containing apoptotic protein (e.g., HER2). As used throughout the present application, the term "antibody" refers to a whole antibody (e.g., IgM, IgG, IgA, IgD, or IgE) molecule that is generated by any one of a variety of methods that are known in the art. The antibody can be made in, or derived from, any of a variety of species, e.g., humans, non-human primates (e.g., monkeys, baboons, or chimpanzees), horses, cattle, pigs, sheep, goats, dogs, cats, rabbits, guinea pigs, gerbils, hamsters, rats, and mice.

The antibody can be a purified or a recombinant antibody. Also useful for the invention are antibody fragments and chimeric antibodies and humanized antibodies made from non-human (e.g., mouse, rat, gerbil, or hamster) antibodies. As used herein, the term "antibody fragment" refers to an antigen-binding fragment, e.g., Fab, F(ab')$_2$, Fv, and single chain Fv (scFv) fragments. An scFv fragment is a single polypeptide chain that includes both the heavy and light chain variable regions of the antibody from which the scFv is derived. In addition, diabodies [Poljak (1994) Structure 2(12):1121-1123; Hudson et al. (1999) J. Immunol. Methods 23(1-2):177-189, the disclosures of both of which are incorporated herein by reference in their entirety] and intrabodies [Huston et al. (2001) Hum. Antibodies 10(3-4):127-142; Wheeler et al. (2003) Mol. Ther. 8(3):355-366; Stocks (2004) Drug Discov. Today 9(22): 960-966, the disclosures of all of which are incorporated herein by reference in their entirety] can be used in the methods of the invention.

Antibody fragments that contain the binding domain of the molecule can be generated by known techniques. For example: F(ab')$_2$ fragments can be produced by pepsin digestion of antibody molecules; and Fab fragments can be generated by reducing the disulfide bridges of F(ab')$_2$ fragments or by treating antibody molecules with papain and a reducing agent. See, e.g., National Institutes of Health, *Current Protocols In Immunology*, Coligan et al., ed. 2.8, 2.10 (Wiley Interscience, 1991), the disclosure of which is incorporated herein by reference in their entirety. scFv fragments can be produced, for example, as described in U.S. Pat. No. 4,642,334, the disclosure of which is incorporated herein by reference in its entirety.

Chimeric and humanized monoclonal antibodies can be produced by recombinant DNA techniques known in the art, for example, using methods described in Robinson et al., International Patent Publication PCT/US86/02269; Akira et al., European Patent Application 184,187; Taniguchi, European Patent Application 171,496; Morrison et al., European Patent Application 173,494; Neuberger et al., PCT Application WO 86/01533; Cabilly et al., U.S. Pat. No. 4,816,567; Cabilly et al., European Patent Application 125,023; Better et al. (1988) Science 240, 1041-43; Liu et al. (1987) J. Immunol. 139, 3521-26; Sun et al. (1987) PNAS 84, 214-18; Nishimura et al. (1987) Canc. Res. 47, 999-1005; Wood et al. (1985) Nature 314, 446-49; Shaw et al. (1988) J. Natl. Cancer Inst. 80, 1553-59; Morrison, (1985) Science 229, 1202-07; Oi et al. (1986) BioTechniques 4, 214; Winter, U.S. Pat. No. 5,225,539; Jones et al. (1986) Nature 321, 552-25; Veroeyan et al. (1988) Science 239, 1534; and Beidler et al. (1988) J. Immunol. 141, 4053-60. The disclosures of all these articles and patent documents are incorporated herein by reference in their entirety.

The compounds identified above can be synthesized by any chemical or biological method. The compounds identified above can also be pure, or can be in a formulation (e.g., a pharmaceutical composition) with one or more additional non-active ingredients (e.g., additional compounds or constituents which do not bind to or inhibit the interaction between a BH3-containing proapoptotic protein (e.g., BAX, BAK, BIM, or BID) and MUC1 (e.g., MUC1-CD)), and can be prepared in an assay-, physiologic-, or pharmaceutically-acceptable diluent or carrier (see Pharmaceutical Compositions and Methods of Treatment below). A composition can also contain one or more additional therapeutic agents (see below).

D. Pharmaceutical Compositions and Methods of Treatment

The present invention also provides for pharmaceutical compositions comprising one or more therapeutically effective amounts of a compound, or a pharmaceutically acceptable salt thereof, together with a pharmaceutically acceptable carrier, diluent, or excipient therefor. Any molecule that has the ability to, for example, to (a) inhibit the interaction between MUC1 and a BH3-containing proapoptotic protein (e.g., BAX, BAK, BIM, or BID), (b) inhibit MUC1 expression, (c) inhibit the growth of a cell (e.g., a colon cancer cell, a breast cancer cell, a prostate cancer cell, a lung cancer cell, a lymphoma, or an immune cell such as a proliferating B- or T-cell), or (d) promote apoptosis in a cell can be considered a compound suitable for the methods described herein. Such compounds can be, but are not necessarily, those identified by any of the screening methods described herein Any of the compounds described herein can be incorporated into pharmaceutical compositions. Such compositions typically include the compound and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. A compound of the present invention can be formulated as a pharmaceutical composition in the form of a syrup, an elixir, a suspension, a powder, a granule, a tablet, a capsule, a lozenge, a troche, an aqueous solution, a cream, an ointment, a lotion, a gel, an emulsion, etc. Supplementary active compounds can also be incorporated into the compositions.

A pharmaceutical composition is formulated to be compatible with its intended route of administration. Examples of routes of administration include oral, rectal, and parenteral, e.g., intravenous, intramuscular, intradermal, subcutaneous, inhalation, transdermal, or transmucosal. Solutions or suspensions used for parenteral application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The compositions can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL3 (BASF, Parsippany, N.J.) or phosphate buffered saline (PBS). In all cases, the composition must be sterile and should be fluid to the extent that easy syringability exists. It should be stable under the conditions of manufacture and storage and must be preserved against contamination with microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of contamination with microorganisms can be achieved by various antibacterial and antifungal agents, for example, parabens, chlorobutanol, phenol, ascorbic acid, thimerosal, and the like. In many cases, it will be desirable to include isotonic agents, for example, sugars, polyalcohols such as manitol, sorbitol, sodium chloride in the composition. Prolonged absorption of the injectable compositions can be facilitated by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the methods of preparation can include vacuum drying or freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

The powders and tablets contain from 1% to 95% (w/w) of the active compound. In certain embodiments, the active compound ranges from 5% to 70% (w/w). Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposbmal suspensions (including liposomes targeted to infected cells with monoclonal antibodies to cancer antigens such as HER2 or therapeutic peptides) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. Dosage units can also be accompanied by instructions for use.

The dose administered to a subject, in the context of the present invention should be sufficient to affect a beneficial therapeutic response in the subject over time. The term "subject" refers to a member of the class Mammalia. Examples of mammals include, without limitation, humans or non-human primates (e.g., chimpanzees, baboons, or monkeys), mice, rats, rabbits, guinea pigs, gerbils, hamsters, horses, livestock (e.g., cows, pigs, sheep, or goats), dogs, cats, or whales.

The dose will be determined by the efficacy of the particular compound employed and the condition of the subject, as well as the body weight or surface area of the subject to be treated. The size of the dose also will be determined by the existence, nature, and extent of any adverse side effects that accompany the administration of a particular compound in a particular subject. In determining the effective amount of the compound to be administered in the treatment or prophylaxis of the disease being treated, the physician can evaluate factors such as the circulating plasma levels of the compound, compound toxicities, and/or the progression of the disease, etc. In general, the dose equivalent of a compound is from about 1 μg/kg to 100 mg/kg for a typical subject. Many different administration methods are known to those of skill in the art.

For administration, compounds of the present invention can be administered at a rate determined by factors that can include, but are not limited to, the pharmacokinetic profile of the compound, contraindicated drugs, and the side effects of the compound at various concentrations, as applied to the mass and overall health of the subject. Administration can be accomplished via single or divided doses.

Toxicity and therapeutic efficacy of such compounds can be determined by known pharmaceutical procedures, for example, in cell culture or experimental animals (animal models of cancer, e.g., colon, breast, prostate, or lung cancer models). These procedures can be used, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue in order to minimize potential damage to normal (e.g., non-cancer or non-inflammatory) cells and, thereby, reduce side effects.

The data obtained from the cell culture assays and animal studies can be used in formulating a range of dosage for use in humans. The dosage of such compounds lies generally within a range of circulating concentrations that include the ED50 with little or no toxicity. The dosage may vary within this range depending upon the dosage form employed and the route of administration utilized. For a compound used as described herein (e.g., for treating cancer or an inflammatory condition in a subject), the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Compounds that inhibit the growth of a cell, (i.e., a mammalian cell, a human cancer cell) can be any of the compounds described herein.

As defined herein, a therapeutically effective amount of a compound is an amount of the compound that is capable of producing a medically desirable result (e.g., decreased proliferation of cancer cells or decreased inflammation) in a treated animal. A therapeutically effective amount of a compound (i.e., an effective dosage) includes milligram or microgram amounts of the compound per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). It is furthermore understood that appropriate doses of a compound depend upon the potency of the compound with respect to the inhibition of the cell growth (i.e., inhibition of the growth of a cancer cell). When one or more of these compounds is to be administered to an animal (e.g., a human) to treat an infection or a cancer, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated. One in the art will also appreciate that certain additional factors may influence the dosage and timing required to effectively treat a subject, including but not limited to the severity of the disease or disorder, previous treatments, and other diseases present. Moreover, treatment of a subject with a therapeutically effective amount of a compound can include a single treatment or can include a series of treatments.

A compound or pharmaceutical composition thereof described herein can be administered to a subject as a combination therapy with another treatment, e.g., a treatment for a cancer or inflammation. For example, the combination therapy can include administering to the subject (e.g., a human patient) one or more additional agents that provide a therapeutic benefit to the subject who has, or is at risk of developing, (or suspected of having) a cancer. Thus, the compound or pharmaceutical composition and the one or more additional agents are administered at the same time. Alternatively, the compound can be administered first in time and the one or more additional agents administered second in time. The one or more additional agents can be administered first in time and the compound administered second in time. The compound can replace or augment a previously or currently administered therapy. For example, upon treating with a compound of the invention, administration of the one or more additional agents can cease or diminish, e.g., be administered at lower levels. Administration of the previous therapy can also be maintained. In some instances, a previous therapy can be maintained until the level of the compound (e.g., the dosage or schedule) reaches a level sufficient to provide a therapeutic effect. The two therapies can be administered in combination.

It will be appreciated that in instances where a previous therapy is particularly toxic (e.g., a treatment for cancer or inflammation with significant side-effect profiles), administration of the compound can be used to offset and/or lessen the amount of the previously therapy to a level sufficient to give the same or improved therapeutic benefit, but without the toxicity.

In some instances, when the subject is administered a compound or pharmaceutical composition of the invention the first therapy is halted. The subject can be monitored for a first pre-selected result, e.g., an improvement in one or more symptoms of a cancer or an inflammatory condition such as any of those described herein (e.g., see above). In some cases, where the first pre-selected result is observed, treatment with the compound is decreased or halted. The subject can then be monitored for a second pre-selected result after treatment with the compound is halted, e.g., a worsening of a symptom of a cancer. When the second pre-selected result is observed, administration of the compound to the subject can be reinstated or increased, or administration of the first therapy is reinstated, or the subject is administered both a compound and first therapy, or an increased amount of the compound and the first therapeutic regimen.

The compound can also be administered with a treatment for one or more symptoms of a disease (e.g., a cancer or inflammatory condition). For example, the compound can be co-administered (e.g., at the same time or by any combination regimen described above) with, e.g., a pain medication or a treatment for anemia (e.g., Erythropoietin (EPO)).

The pharmaceutical compositions can be included in a container, pack, or dispenser together with instructions for administration.

E. Methods of Inhibiting an Interaction Between MUC1 and BH3-Containing Proapoptotic Proteins Provided herein are in vitro, in vivo, and ex vivo methods of inhibiting an interaction between MUC1 and a BH3-containing proapoptotic protein (e.g., BAX, BAK, BIM, or BID). While the invention is not limited by any particular theory or mechanism of action, the binding of MUC1 to an BH3-containing proapoptotic protein (e.g., BAX, BAK, BIM, or BID) could prevent apoptosis induced by the BH3-containing proapoptotic protein and thus promote the development or viability of a dividing cell (e.g., a human cancer cell or a proliferating inflammatory cell (e.g., an immune cell such as proliferating B- or T-cell)). Therefore, inhibition of this interaction can have general applicability in inhibiting the growth or viability of a cancer or inflammatory cell, e.g., this can be a method of inducing apoptosis in a cell. Inhibition of cell growth can be a reversible inhibition of cell growth, or more preferably can be an irreversible inhibition of cell growth (i.e., causing the death of the cell such as apoptosis). Where the methods are in vivo or ex vivo, such methods can also be useful in the treatment of cancers or inflammatory conditions (including any of the inflammatory conditions described herein).

Inhibition of the interaction between MUC1 and a BH3-containing proapoptotic protein (e.g., BAX, BAK, BIM, or BID) can include inhibition of an interaction between MUC1 and any BH3-containing proapoptotic protein (e.g., BAX, BAK, BIM, or BID) described herein. Similarly, MUC1, as referred to in the method, can include a full-length, wild-type, mature MUC1 polypeptide (e.g., MUC1 having SEQ ID NO:1), the MUC1-cytoplasmic domain (MUC1-CD) (e.g., the MUC1-CD having SEQ ID NO:2), or a functional or BH3-containing proapoptotic protein-binding fragment of a MUC1 polypeptide. Cells can include both prokaryotic (e.g., bacterial cells) and eukaryotic cells. Eukaryotic cells can include, for example, yeast, insect, plant, fish, reptile, and mammalian cells (e.g., mouse, rat, rabbit, guinea pig, dog, cat, pig, horse, goat, cow, whale, monkey, or human). The cells can be normal, transformed, or malignant and of any histological type, e.g., without limitation, epithelial cells, fibroblasts, lymphoid cells, macrophages/monocytes, granulocytes, keratinocytes, or muscle cells. Cancer cells useful in the method can include cancer cells from cancers such as, but not limited to, lung cancer, breast cancer, colon cancer, pancreatic cancer, renal cancer, stomach cancer, liver cancer, bone cancer, hematological cancer, neural tissue cancer, melanoma, thyroid cancer, ovarian cancer, testicular cancer, prostate cancer, cervical cancer, vaginal cancer, and bladder cancer. Suitable cell lines include those recited in the examples, e.g., breast cancer or colon cancer cell lines.

Where the methods are in vitro cell-based methods or in vivo, the methods of inhibiting an interaction between MUC1 and a BH3-containing proapoptotic protein (e.g., BAX, BAK, BIM, or BID) can optionally include a step of identifying a cell as one expressing MUC1. Such identification can include, for example, identifying (or detecting) whether a cell expresses MUC1 mRNA or MUC1 protein. Suitable methods of identifying (or detecting) the expression of MUC1 protein or MUC1 mRNA are well known to those of skill in the art, and are described herein. These methods can include, for example, SDS-polyacrylamide gel electrophoresis/western blotting techniques using antibodies specific for MUC1 (for detection of protein), or RT-PCR or northern blotting techniques for detection of mRNA expression. The cell can be any cell that expresses MUC1, e.g., a cell that expresses an endogenous or a recombinant or exogenous MUC1 mRNA or polypeptide.

The cell can also, optionally, be identified as one expressing the appropriate BH3-containing proapoptotic protein (e.g., BAX, BAK, BIM, or BID). Suitable detection methods for mRNA and protein include those described above. The cell can be any cell expressing the appropriate BH3-containing proapoptotic protein (e.g., BAX, BAK, BIM, or BID), including cells that express endogenous, recombinant, or otherwise exogenous BH3-containing proapoptotic protein (e.g., BAX, BAK, BIM, or BID) mRNA or protein.

The cell can also, optionally, be identified as one expressing a BH2-containing anti-apoptotic protein such as Bcl-2 or Bcl-$x_L$, which BH2-containing protein is capable of binding to the BH3-containing proapoptotic protein (e.g., BAX, BAK, BIM, or BID). Suitable methods for mRNA and protein detection as above. The cell can be any cell expressing the BH2-containing protein (endogenously or exogenously) as above.

Compounds useful in the methods of inhibiting an interaction between MUC1 and a BH3-containing proapoptotic protein (e.g., BAX, BAK, BIM, or BID) can include any of the compounds described herein, or any other compounds with the appropriate inhibitory activity. Suitable compounds can include small molecules, antibodies, an antibody fragments, polypeptides, or a peptidomimetics. Compounds can also include nucleic acids, for example, nucleic acids that inhibit the mRNA or protein expression of MUC1 or a BH3-containing proapoptotic protein (e.g., BAX, BAK, BIM, or BID) (e.g., siRNA or anti-sense nucleic acids; see "Methods of Inhibiting MUC1 Expression"). Other exemplary compounds for use in the methods include MUC1 or BH3-containing proapoptotic protein (e.g., BAX, BAK, BIM, or BID) polypeptides or their functional fragments. Examples of potential functional fragments of MUC1 include, for example, the MUC1-CD (e.g., the MUC1-CD having SEQ ID NO:2), or fragments of the MUC1-CD containing amino acids 1-45, amino acids 2-71, amino acids 5-70, amino acids 10-70, amino acids 10-65, amino acids 15-70, amino acids 20-70, amino acids 25-70, amino acids 30-70, amino acids 35-70, amino acids 40-70, amino acids 45-70, amino acids 46-72, amino acids 50-70, amino acids 55-70, or amino acids 55-70.

While the invention is not limited by any particular mechanism of action, the binding of MUC1 to a BH3-containing proapoptotic protein (e.g., BAX, BAK, BIM, or BID) could inhibit BH3-containing proapoptotic protein-mediated apoptosis, e.g., following treatment with an apoptosis-inducing stimulus. Thus, co-culturing a cell in the presence of, or further administering to a subject (e.g., a human patient), an inhibitor of an interaction between MUC1 and a BH3-containing proapoptotic protein (e.g., BAX, BAK, BIM, or BID) and one or more additional therapeutic agents can increase the efficacy of the one or more therapeutic agents (e.g., one or more therapeutic agents for the treatment of cancer). In some embodiments of the methods of inhibiting the interaction between MUC1 and a BH3-containing proapoptotic protein (e.g., BAX, BAK, BIM, or BID), the cells or subjects can be further treated with one or more additional therapeutic agents. Such therapeutic agents can include, but are not limited to, one or more chemotherapeutic agents, one or more forms of ionizing radiation, or hormonal therapy, such as any of those described herein. Particularly, but not necessarily, where the cell (e.g., inflammatory cell (e.g., an immune cell) or cancer cell (e.g., of a tumor)) expresses a mutant form or an oncogenic amount of a BH2-containing antiapoptotic protein such as Bcl-2, the therapeutic agents include, e.g., an inhibitor of a BH2-containing antiapoptotic protein such as Bcl-2.

In Vitro Methods of Inhibiting an Interaction Between MUC1 and a BH3-Containing Proapoptotic Proteins Provided herein are in vitro methods of inhibiting an interaction between a MUC1 reagent and a BH3-containing proapoptotic protein (e.g., BAX, BAK, BIM, or BID) reagent. The method can be useful, for example, in scientific studies to investigate the role of MUC1 in a BH3-containing proapoptotic protein-mediated apoptosis, or any other scientific studies in which inhibiting the interaction between MUC1 and a BH3-containing proapoptotic protein (e.g., BAX, BAK, BIM, or BID) can be beneficial. Where the method is a cell-based method, it can also be useful as a further screening step (e.g., a cell-free method of identifying a compound that inhibits the binding of a BH3-containing proapoptotic protein to MUC1 described above) in, e.g., a drug screening cascade, following the biochemical identification of a compound that inhibits the binding of a BH3-containing proapoptotic protein (e.g., BAX, BAK, BIM, or BID) to MUC1. Moreover, it can also serve as a "positive control" in assays to identify compounds with the same activity.

The method can include the steps of: contacting (i) a MUC1 reagent; (ii) a BH3-containing proapoptotic protein (e.g., BAX, BAK, BIM, or BID) reagent; or (iii) a molecular complex comprising (i) and (ii) with a compound that inhibits the interaction between MUC1 and a BH3-containing proapoptotic protein reagent. The method can be cell-based, and utilize any of the cells described herein (e.g., see above). The cell-based method can involve the steps of identifying a cell as one expressing a BH2-containing antiapoptotic protein; and culturing the cell with a compound that inhibits the interaction between a MUC1 reagent and a BH3-containing proapoptotic protein reagent, wherein the BH3-containing proapoptotic protein reagent is capable of binding to the BH2-protein. The cell-based method can also include the step of determining whether the cell is one expressing MUC1.

Methods for identifying or detecting a cell as expressing MUC1 mRNA or protein, or a BH2-containing antiapoptotic protein mRNA or protein, are well known to those in the art and are described above. Suitable concentrations of the inhibitory compound can be elucidated through routine experimentation and appropriate methods to establish useful concentrations are well known to one of skill in the art. As described above, the cell may be co-cultured with one or more additional therapeutic agents.

It should be understood that where the cell is identified as one expressing a MUC1, the expressed MUC1 can be the MUC1 reagent of the method. For example, a cell identified as one expressing a full-length, wild-type, mature MUC1 protein would thus have a MUC1 reagent that is full-length, wild-type, mature MUC1 protein.

Methods of determining or detecting the inhibition of an interaction between MUC1 and a BH3-containing proapoptotic protein (e.g., BAX, BAK, BIM, or BID) are known in the art, and include, for example, in vitro and in situ methods. Such methods are described herein. One method of determining inhibition of the interaction between MUC1 and a BH3-containing proapoptotic protein (e.g., BAX, BAK, BIM, or BID) is an immunoprecipitation method and is set forth in the Examples below. Briefly, cells cultured in the presence of an inhibitory compound can be washed and harvested from the culture vessel. The cells can then be lysed using non-denaturing buffers that preserve protein-protein interactions, for example, buffers containing Nonidet-40 (NP-40) or Triton X-100 detergents. The lysates can then be clarified using, for example, centrifugation to remove insoluble debris. Clarified lysates can then be subjected to immunoprecipitation by adding to the lysate an antibody specific for either a BH3-containing proapoptotic protein (e.g., BAX, BAK, BIM, or BID) or MUC1 for a time sufficient to allow for the binding of the antibody to its cognate antigen. Antibody-protein complexes are isolated from the lysate solution by coupling the complexes to solid support matrices. Examples of such solid support matrices include insoluble beads conjugated to anti-IgG antibodies or other antibody-binding moieties, for example, bacterial Protein-A or Protein-G. Isolated immunocomplexes can then be solubilized in Laemmli buffer (optionally containing reducing agent) and subjected to SDS-polyacrylamide gel electrophoresis (SDS-PAGE). Immunoblotting of the samples using antibodies specific for one or both of MUC1 and a BH3-containing proapoptotic protein (e.g., BAX, BAK, BIM, or BID) can then be used to determine whether a compound has inhibited the interaction between MUC1 and a BH3-containing proapoptotic protein. A reduced amount of a BH3-containing proapoptotic protein (e.g., BAX, BAK, BIM, or BID) present in anti-MUC1 immunoprecipitates from cells treated with a compound as compared to the amount of the BH3-containing proapoptotic protein present in MUC1 immunoprecipitates from cells not treated with the compound indicates that the compound has inhibited the interaction of the two proteins. Similarly, a reduced amount of MUC1 protein present in a BH3-containing proapoptotic protein (e.g., an anti-BAX antibody) immunoprecipitate (made, for example, with anti-BAX antibody) from cells treated with a compound, as compared to the amount of MUC1 protein associated in a corresponding immunoprecipitate from cells not treated with the compound would indicate that the compound has inhibited the interaction of the two proteins.

Another method of determining inhibition of an interaction between MUC1 and a BH3-containing proapoptotic protein (e.g., BAX, BAK, BIM, or BID) is an in situ staining method. Immunostaining methods are well known to those of skill in the art and include embodiments where the cells are still viable (e.g., confocal microscopy of live cells) or are fixed cells (e.g., immunohistochemistry). Antibodies specific for MUC1 and a BH3-containing proapoptotic protein (e.g., BAX, BAK, BIM, or BID) polypeptides are applied (e.g., administered, delivered, contacted) to cells. The antibodies are independently labeled with a different detectable label (e.g., a different colored fluorophore (e.g., rhodamine, texas red, FITC, Green fluorescent protein, Cy3, Cy5) such that they can be readily and easily distinguished from one another. Use of an appropriate microscope (e.g., a confocal microscope) with the appropriate optical filters can identify the position of the labeled antibodies in a given cell. When each of the positions of the two proteins are determined (i.e., the location of their respective detectable label within the cell as determined by antibody binding), if they are found to occupy the same space, the two proteins are said to co-localize. Thus, when two proteins co-localize in the absence of a compound but do not co-localize in the presence of a compound, this can indicate that the compound has inhibited the interaction between the two proteins. Optionally the cells can be fixed, for example, using paraformaldehyde or formaldehyde, and permeabilized using a detergent (e.g., Triton-X100).

It in understood that co-localization of two proteins (e.g., MUC1 and a BH3-containing proapoptotic protein such as BAX, BAK, BIM, or BID) can be a direct, physical interaction of two proteins or it can be due to the localization of two proteins to a given, defined site in a cell (e.g., the nucleus, the cell membrane, the endoplasmic reticulum, the mitochondria) that is not due to a direct physical interaction between the two proteins. For example, MUC1 and a BH3-containing proapoptotic protein (e.g., BAX, BAK, BIM, or BID) can co-localize in the cytoplasm of a cell, but in the absence of an interaction (e.g., in the presence of an inhibitor of their interaction) between them they can relocalize to distinct regions (e.g., the nucleus). In this regard, to define the particular localizations or organelles where localization occurs, it can be useful to use antibodies or other dyes that specifically detect the particular organelles or cellular regions of interest.

The skilled artisan would recognize that through routine adaptation of the above methods of detecting inhibition of an interaction, one could detect whether a BH3-containing proapoptotic protein (or reagent) interacts with a BH2-containing antiapoptotic protein. For example, immunoprecipitations can be performed as described using antibodies specific for a BH3-containing proapoptotic protein such as BAX, BID, BAK, or BIM. Immunoprecipitated material could be subjected to SDS-PAGE and the amount or presence of BH2-containing antiapoptotic protein confirmed by western blot analysis using antibodies specific for the associated BH2-containing antiapoptotic protein such as Bcl-2. Alternatively, immunoprecipitations can be performed using antibodies specifically recognizing a BH2-containing antiapoptotic protein, such as Bcl-2, and the amount or presence of an associated BH3-containing antiapoptotic protein could be detected.

Since it appears that the binding of MUC1 to a BH3-containing proapoptotic protein (e.g. BAX, BAK, BIM, or BID) may modulate the activity of a BH3-containing proapoptotic protein to induce apoptosis (e.g., by subsequent inhibition of a BH2-containing antiapoptotic protein), inhibiting the interaction between MUC1 and a BH3-containing proapoptotic protein (e.g., BAX, BAK, BIM, or BID) can also be determined by detecting increased cell death or apoptosis of a cell in the presence of compound. For example, cells are plated on a solid support matrix (e.g., a plastic tissue culture plate, or a multiwell (96 or 386-well) tissue culture plate) and grown in appropriate medium. Cells are then co-cultured in the absence or presence of an appropriate inhibitory compound and then exposed to elevated temperatures (e.g., heat shock) for a predetermined amount of time. Often, a control compound (e.g., a known inhibitor of known concentration) is also added to a sample of cells as an internal standard. In addition, a sample of cells is grown in the presence of a carrier, buffer, or solvent, in which the compound is delivered. Methods of detecting (e.g., determining or measuring) increased heat-shock-induced apoptosis in the presence of an inhibitor of MUC1-BH3-containing proapoptotic protein interaction are myriad and well known to those of ordinary skill in the art. These methods can include, for example, counting the number of viable cells remaining in the well after the period of treatment with the compound. In this method, cells can be trypsinized from the plate, washed, stained with a dye (e.g., typan blue), and counted using a microscope or mechanical cell counter (Beckman-Coulter Z1™ Series COULTER COUNTER® Cell and Particle Counter). Since dyes like trypan blue are only taken up by dead or dying cells, this method allows for discrimination (i.e., blue or white cell) between viable and non-viable cells in a population. Another method for determining increased apoptosis in the presence of an inhibitory compound (e.g., any one of the compositions described herein) is monitoring cell death. Such methods are well known to those of skill in the art, and include propidium iodide staining of genomic DNA, or commercially available kits, such as, In situ Cell Death Detection ELISA Kit (Roche, Indianapolis, Ind.); and APO-Direct, APO-BRDU, or Annexin-FITC Apoptosis Kit (BD-Pharmingen, San Diego, Calif.). Such methods and kits for determining programmed cell death can optionally be used in conjunction with fluorescence flow cytometry (FFC). Examples of the methods and machines (instruments) useful for such methods are further described in "Methods of Inducing Apoptosis."

In a preferred embodiment, any of the in vitro methods for detecting inhibition of the interaction between MUC1 and a BH3-containing proapoptotic protein (e.g., BAX, BAK, BIM, or BID) (in vivo or in vitro, or any screening methods described herein) can be performed in any format that allows for rapid preparation, processing, and analysis of multiple reactions. This can be, for example, in multi-well assay plates (e.g., 96 wells or 386 wells). Stock solutions for various agents can be made manually or robotically, and all subsequent pipetting, diluting, mixing, distribution, washing, incubating, sample readout, data collection and analysis can be done robotically using commercially available analysis software, robotics, and detection instrumentation capable of detecting the signal generated from the assay. Examples of such detectors include, but are not limited to, spectrophotometers, luminometers, fluorimeters, and devices that measure radioisotope decay.

In Vivo Methods of Inhibiting an Interaction Between MUC1 and a BH3-Containing Proapoptotic Protein The invention features a method of inhibiting an interaction between MUC1 and a BH3-containing proapoptotic protein (e.g., BAX, BAK, BIM, or BID), which includes the steps of: optionally identifying a subject as having, or at risk of developing, (or suspected to have) a cancer comprising one or more cancer cells expressing MUC1; and delivering to the subject a compound that inhibits the interaction between MUC1 and a BH3-containing proapoptotic protein (e.g., BAX, BAK, BIM, or BID). The method can lead to apoptosis in a cell, thus the method is a method of promoting apoptosis in a cell. The method can also include the optional step of identifying a subject as one having, suspected of having (or at risk of developing), a cancer comprising one or more cells expressing a BH2-containing antiapoptotic protein such as Bcl-2 or Bcl-$x_L$. The BH2-protein is one that binds to the BH3-containing proapoptotic protein. The method can also include the steps of determining whether (i) the one or more cancer cells of the subject cancer express MUC1 and/or a BH2-containing antiapoptotic protein and/or (ii) if inhibition of an interaction between MUC1 and a BH3-containing proapoptotic protein occurred.

In one in vivo approach, a compound that inhibits binding of MUC1 to a BH3-containing proapoptotic protein (e.g., BAX, BAK, BIM, or BID) is administered to a subject. The subject can be any mammal, e.g., a human (e.g., a human subject) or a non-human primate (e.g., chimpanzee, baboon, or monkey), mouse, rat, rabbit, guinea pig, gerbil, hamster, horse, a type of livestock (e.g., cow, pig, sheep, or goat), a dog, cat, or a whale. Generally, the compounds of the invention will be suspended in a pharmaceutically-acceptable carrier (e.g., physiological saline) and administered orally or injected intravenously, subcutaneously, intramuscularly, intrathecally, intraperitoneally, intrarectally, intravaginally, intranasally, intragastrically, intratracheally, or intrapulmonarily. They can also be delivered directly to tumor cells, e.g., to a tumor or a tumor bed following surgical excision of the tumor, in order to kill any remaining tumor cells. The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.0001 mg/kg-100 mg/kg. Wide variations in the needed dosage are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization as is well understood in the art. Administrations can be single or multiple (e.g., 2-, 3-, 4-, 6-, 8-, 10-, 20-, 50-, 100-, 150-, or more fold). Encapsulation of the polypeptide in a suitable delivery vehicle (e.g., polymeric microparticles or implantable devices) may increase the efficiency of delivery, particularly for oral delivery.

Alternatively, where an inhibitory compound is a polypeptide, a polynucleotide containing a nucleic acid sequence encoding the polypeptide can be delivered to appropriate cells in a mammal. Expression of the coding sequence can be directed to any cell in the body of the subject. However, expression will preferably be directed to cells in the vicinity of the tumor cells whose proliferation it is desired to inhibit. Expression of the coding sequence can be directed to the tumor cells themselves. This can be achieved by, for example, the use of polymeric, biodegradable microparticle or microcapsule delivery devices known in the art. Another way to achieve uptake of the nucleic acid is using liposomes, prepared by standard methods. The vectors can be incorporated alone into these delivery vehicles or co-incorporated with tissue-specific or tumor-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells [Cristiano et al. (1995), J. Mol. Med. 73:479, the disclosure of which is incorporated herein by reference in its entirety]. Alternatively, tissue specific targeting can be achieved by the use of tissue-specific transcriptional regulatory elements (TRE) which are known in the art. Delivery of "naked DNA" (i.e., without a delivery vehicle) to an intramuscular, intradermal, or subcutaneous site is another means to achieve in vivo expression.

In the relevant polynucleotides (e.g., expression vectors), the nucleic acid sequence encoding the polypeptide of interest with an initiator methionine and optionally a targeting sequence is operatively linked to a promoter or enhancer-promoter combination. Short amino acid sequences can act as signals to direct proteins to specific intracellular compartments. Such signal sequences are described in detail in U.S. Pat. No. 5,827,516, the disclosure of which is incorporated herein by reference in its entirety.

Enhancers provide expression specificity in terms of time, location, and level. Unlike a promoter, an enhancer can function when located at variable distances from the transcription initiation site, provided a promoter is present. An enhancer can also be located downstream of the transcription initiation site. To bring a coding sequence under the control of a promoter, it is necessary to position the translation initiation site of the translational reading frame of the peptide or polypeptide between one and about fifty nucleotides downstream (3') of the promoter. Promoters of interest include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3 phosphoglycerate kinase, the promoters of acid phosphatase, and the promoters of the yeast a mating factors, the adenoviral E1b minimal promoter, or the thymidine kinase minimal promoter. The DF3 enhancer can be particularly useful for expression of an inhibitory compound in cells that naturally express MUC1, for example, normal epithelial cells or malignant epithelial cells (carcinoma cells), e.g., breast cancer cells [see U.S. Pat. Nos. 5,565,334 and 5,874,415, the disclosures of which are incorporated herein by reference in their entirety]. The coding sequence of the expression vector is operatively linked to a transcription terminating region.

Suitable expression vectors include plasmids and viral vectors such as herpes viruses, retroviruses, vaccinia viruses, attenuated vaccinia viruses, canary pox viruses, adenoviruses and adeno-associated viruses, among others.

Polynucleotides can be administered in a pharmaceutically acceptable carrier. Pharmaceutically acceptable carriers are biologically compatible vehicles that are suitable for administration to a human, e.g., physiological saline or liposomes. A therapeutically effective amount is an amount of the polynucleotide that is capable of producing a medically desirable result (e.g., decreased proliferation of cancer cells) in a treated animal. As is well known in the medical arts, the dosage for any one patient depends upon many factors, including the patient's size, body surface area, age, the particular compound to be administered, sex, time and route of administration, general health, and other drugs being administered concurrently. Dosages will vary, but a preferred dosage for administration of polynucleotide is from approximately $10^6$ to approximately $10^{12}$ copies of the polynucleotide molecule. This dose can be repeatedly administered, as needed. Schedules and co-administration can be any of those described herein (see, for example, "Pharmaceutical Compositions and Methods of Treatment"). Routes of administration can be any of those listed above.

Ex Vivo Methods of Inhibiting an Interaction Between MUC1 and a BH3-Containing Proapoptotic Protein An ex vivo strategy can involve transfecting or transducing cells obtained from the subject (or another subject) with a polynucleotide encoding a polypeptide that inhibits an interaction between MUC1 and a BH3-containing proapoptotic protein (e.g., BAX, BAK, BIM, or BID). The transfected or transduced cells are then returned to the subject. The cells can be any of a wide range of types including, without limitation, hemopoietic cells (e.g., bone marrow cells, macrophages, monocytes, dendritic cells, T cells, or B cells), fibroblasts, epithelial cells, endothelial cells, keratinocytes, or muscle cells. Such cells act as a source of the inhibitory polypeptide for as long as they survive in the subject. Alternatively, tumor cells or immune cells, preferably obtained from the subject (autologous) but potentially from a subject of the same species other than the subject (allogeneic), can be transfected or transformed by a vector encoding the inhibitory polypeptide. The tumor cells, preferably treated with an agent (e.g., ionizing irradiation) that ablates their proliferative capacity, are then introduced into the subject, where they secrete the polypeptide.

The ex vivo methods include the steps of harvesting cells from a subject, culturing the cells, transducing them with an expression vector, and maintaining the cells under conditions suitable for expression of the polypeptide that inhibits binding of MUC1 to a BH3-containing proapoptotic protein (e.g., BAX, BAK, BIM, or BID). These methods are known in the art of molecular biology. The transduction step is accomplished by any standard means used for ex vivo gene therapy, including calcium phosphate, lipofection, electroporation, viral infection, and biolistic gene transfer. Alternatively, liposomes or polymeric microparticles can be used. Cells that have been successfully transduced can be selected, for example, for expression of the coding sequence or of a drug resistance gene. The cells may then be lethally irradiated (if desired) and injected or implanted into the subject.

F. Methods of Promoting Apoptosis

Provided herein are in vitro, in vivo, and ex vivo methods of promoting apoptosis (in a cell). While the invention is not limited by any particular theory or mechanism of action, MUC1 binding to BH3-containing pro-apoptotic proteins such as BAX and BID may prevent their pro-apoptotic activity in vivo, and thus promote the viability/survival of, e.g., cancer cells or immune cells involved in an inflammatory condition. Therefore, apoptosis can be promoted by inhibiting MUC1.

Alternatively, where a cell is one expressing a BH2-containing antiapoptotic protein (e.g., a cancer cell expressing an oncogenic form or elevated amount of an antiapoptotic protein such as Bcl-2), apoptosis can be induced in a cell by culturing a cell with an inhibitor of the antiapoptotic protein (e.g., Bcl-2).

Inhibition of MUC1 and/or a BH2-containing antiapoptotic protein includes inhibition of protein or mRNA expression. Inhibition can also be inhibition of the activity of MUC1 or a BH2-containing antiapoptotic protein. An activity of a BH2-containing protein can be antiapoptotic activity of the BH2-containing antiapoptotic protein. Activity of MUC1 can be, e.g., inhibition of the anti-apoptotic function of MUC1 such as inhibition of an interaction between MUC1 and a BH3-containing proapoptotic protein.

As above, where the methods are in vivo or ex vivo, any of the preceding methods can also be useful in the treatment of cancers (e.g., any of the cancer types described herein) or inflammatory diseases such as any of those described herein.

Where the methods include the step of identifying a cell (e.g., a cancer cell or an inflammatory cell) as one expressing a MUC1, such identification can include, for example, identifying (or detecting) whether a cell expresses MUC1 mRNA or protein. Suitable methods of identifying (or detecting) the expression of MUC1 protein or mRNA are well known in the skill and are described herein. It is understood that the same types of detection methods (e.g., for mRNA or protein) apply where the methods include the step of identifying a cell (e.g., a cancer cell) as one expressing a BH3-containing proapoptotic protein.

Compounds useful in the methods of inhibiting MUC1 expression or a BH2-containing antiapoptotic protein include any of the compounds described herein, or any other compounds with the appropriate inhibitory activity. Suitable compounds can include small molecules, antibodies, an antibody fragments, polypeptides, or a peptidomimetics.

Several exemplary compounds for inhibiting the BH2-containing antiapoptotic protein Bcl-2 are well known to those in the art and include, for example, clinical compounds such as GX15-070 (Gemin X), AT-101 (Ascenta Therapeutics), and ABT737 (Abbot Laboratories) (Saleh et al. AACR-NCI-EORTC International Conference on Molecular Targets and Cancer Therapeutics in Philadelphia, Pa. (November 2005) Phase I Trial of AT-101; Goldsmith et al. (2005) Cancer Lett. 228(1-2):133-141).

Compounds can also include nucleic acids, for example, nucleic acids that inhibit the mRNA or protein expression of MUC1 or a BH2-containing antiapoptotic protein (e.g., Bcl-2 or Bcl-$x_L$), for example, an antisense oligonucleotide that hybridizes to a MUC1 mRNA transcript, or a MUC1-specific small interference RNA (siRNA) (e.g., an MUC1-specific siRNA). Specific antisense oligonucleotides hybridize to, e.g., MUC1 or BH2-protein mRNA transcripts and have the effect in the cell of inhibiting expression of the corresponding protein (e.g., MUC1 or the BH2-protein respectfully).

Antisense compounds are generally used to interfere with protein expression either by, for example, interfering directly with translation of a target mRNA molecule, by RNAse-H-mediated degradation of the target mRNA, by interference with 5' capping of mRNA, by prevention of translation factor binding to the target mRNA by masking of the 5' cap, or by inhibiting of mRNA polyadenylation. The interference with protein expression arises from the hybridization of the antisense compound with its target mRNA. A specific targeting site on a target mRNA of interest for interaction with a antisense compound is chosen. Thus, for example, for modulation of polyadenylation a preferred target site on an mRNA target is a polyadenylation signal or a polyadenylation site. For diminishing mRNA stability or degradation, destabilizing sequences are preferred target sites. Once one or more target sites have been identified, oligonucleotides are chosen which are sufficiently complementary to the target site (i.e., hybridize sufficiently well under physiological conditions and with sufficient specificity) to give the desired effect.

With respect to this invention, the term "oligonucleotide" refers to an oligomer or polymer of RNA, DNA, a combination of the two, or a mimetic of either. The term includes oligonucleotides composed of naturally-occurring nucleobases, sugars, and covalent internucleoside (backbone) linkages. The normal linkage or backbone of RNA and DNA is a 3' to 5' phosphodiester bond. The term also refers however to oligonucleotides composed entirely of, or having portions containing, non-naturally occurring components which function in a similar manner to the oligonucleotides containing only naturally-occurring components. Such modified substituted oligonucleotides are often preferred over native forms because of desirable properties such as, for example, enhanced cellular uptake, enhanced affinity for target sequence, and increased stability in the presence of nucleases. In the mimetics, the core base (pyrimidine or purine) structure is generally preserved but (1) the sugars are either modified or replaced with other components and/or (2) the inter-nucleobase linkages are modified. One class of nucleic acid mimetic that has proven to be very useful is referred to as protein nucleic acid (PNA). In PNA molecules the sugar backbone is replaced with an amide-containing backbone, in particular an aminoethylglycine backbone. The bases are retained and are bound directly to the aza nitrogen atoms of the amide portion of the backbone. PNA and other mimetics useful in the instant invention are described in detail in U.S. Pat. No. 6,210,289, the disclosure of which is incorporated herein by reference in its entirety.

The antisense oligomers useful in the methods of the invention generally comprise about 8 to about 100 (e.g., about 14 to about 80 or about 14 to about 35) nucleobases (or nucleosides where the nucleobases are naturally occurring).

The antisense oligonucleotides can themselves be introduced into a cell or an expression vector containing a nucleic sequence (operably linked to a TRE) encoding the antisense oligonucleotide can be introduced into the cell. In the latter case, the oligonucleotide produced by the expression vector is an RNA oligonucleotide and the RNA oligonucleotide will be composed entirely of naturally occurring components.

Also useful in the method of inhibiting the expression of MUC1 or a BH2-containing antiapoptotic protein (e.g., Bcl-2 or Bcl-$x_L$) are double-stranded small interference RNA (siRNA) homologous to DNA sequence coding for the MUC1 or antiapoptotic protein, which can be used to reduce expression of the protein in a cell. See, e.g., Fire et al. (1998) Nature 391:806-811; Romano and Masino (1992) Mol. Microbiol. 6:3343-3353; Cogoni et al. (1996) EMBO J. 15:3153-3163; Cogoni and Masino (1999) Nature 399:166-169; Misquitta and Paterson (1999) Proc. Natl. Acad. Sci. USA 96:1451-1456; and Kennerdell and Carthew (1998) Cell 95:1017-1026. The disclosures of all these articles are incorporated herein by reference in their entirety.

The sense and anti-sense RNA strands of siRNA can be individually constructed using chemical synthesis and enzymatic ligation reactions using procedures known in the art. For example, each strand can be chemically synthesized using naturally occurring nucleotides or variously modified nucleotides designed to increase the biological stability of the molecule or to increase the physical stability of the duplex formed between the sense and anti-sense strands, e.g., phosphorothioate derivatives and acridine substituted nucleotides. Some of the nucleotides (e.g., the terminal (either terminus) one, two, three, or four nucleotides) can also be deoxyribonucleotides. The sense or anti-sense strand can also be produced biologically using an expression vector into which, e.g., a target MUC1 or BH2-containing antiapoptotic protein sequence (full-length or a fragment) has been subcloned in a sense or anti-sense orientation. The sense and anti-sense RNA strands can be annealed in vitro before delivery of the dsRNA to cells. Alternatively, annealing can occur in vivo after the sense and anti-sense strands are sequentially delivered to cells.

In Vitro Methods of Promoting Apoptosis

The invention provides in vitro methods of promoting apoptosis by (i) inhibiting MUC1 and/or (ii) inhibiting a BH2-containing antiapoptotic protein. The method can include the steps of: identifying a cell as expressing a BH3-containing proapoptotic protein, and culturing the cell with a compound that inhibits MUC1 expression. The methods can also include the step of determining whether apoptosis occurs.

Such methods can have general applicability in scientific studies on the role of MUC1 in apoptosis. These methods can also be useful in any studies where inhibition of the binding between MUC1 and a BH3-containing proapoptotic protein or inhibiting MUC1 expression is advantageous. Furthermore, as above, such in vitro methods can be used as secondary assays in screening cascades in the pursuit of compounds that promote apoptosis. The methods can also serve as a "positive control" in assays to identify compounds with the same activity.

Methods for identifying or detecting a cell as expressing MUC1 mRNA or protein are well known to those in the art and are described above. These same methods can also be used to detect inhibition of MUC1 mRNA or protein expression. The same methods generally apply to the detection of a cell expressing a BH2-containing antiapoptotic protein such a Bcl-2 or Bcl-$x_L$. Methods for culturing a cell with an inhibitor are widely known in the art and also described above. Suitable concentrations of the inhibitory compound can be elucidated through routine experimentation and such optimization is well known to one of skill in the art. As described above, the cell may be co-cultured with one or more additional therapeutic or chemotherapeutic agents (e.g., an anti-cancer therapy or anti-inflammatory).

Suitable methods of determining inhibition of MUC1 mRNA or protein expression are described above. For example, the level or amount of MUC1 protein expressed in a cell cultured in the presence and absence of a compound can be determined, e.g., using western or dot-blotting techniques. A lowered or reduced expression of MUC1 protein in the presence of a compound as compared to in the absence of a compound indicates that the compound inhibits MUC1 protein expression. Similarly, methods of determining inhibition of expression an antiapoptotic protein such as Bcl-2 or Bcl-$x_L$ are as above. For example, the level or amount of Bcl-2 mRNA expressed in a cell cultured in the presence and absence of a compound can be determined, e.g., using northern blotting or RT-PCR-based techniques. A lowered or reduced expression of Bcl-2 mRNA in the presence of a compound as compared to in the absence of a compound indicates that the compound inhibits Bcl-2 mRNA expression.

It is understood that inhibition of expression can be inhibition of MUC1 mRNA or MUC1 protein expression. It is also understood that inhibition of expression can also be an increased degradation of mRNA or protein.

Since both MUC1 and BH2-containing antiapoptotic proteins regulate cell proliferation and viability, inhibition of cell growth or apoptosis of a cell in the presence of compound can be an indication that MUC1 or the BH2-proteins are inhibited. Methods of determining inhibition of cell proliferation are known in the art and described above. Cells can be co-cultured in the absence or presence of an appropriate inhibitory compound. In some instances, the cells can be co-cultured in the presence of an apoptosis inducing compound such as staurosporin or taxol. Often, a control compound (e.g., a known inhibitor of known concentration) is also added to a sample of cells as an internal standard. In addition, a sample of cells are grown in the presence of a vehicle (e.g., carrier, buffer, or solvent) in which the compound is delivered (e.g., as a control for the effects of the vehicle). Methods of detecting (e.g., determining or measuring) cell growth inhibition by a compound are myriad and well known in the art. These methods can include, for example, counting the number of cells as described above. Another method for determining cell growth inhibition in the presence of an inhibitory compound (e.g., any one of the compositions described herein) following treatment is a metabolic assay, for example, an MTT-metabolic assay (Invitrogen, USA). MTT Diphenyltetrazolium Bromide, is a tetrazolium salt (yellowish) that is cleaved to formazan crystals by the succinate dehydrogenase system which belongs to the mitochondrial respiratory chain, and is only active in viable cells. The mitochondrial succinate dehydrogenase reduces the MTT crystals into purple formazan in the presence of an electron coupling reagent. Following the treatment of the cells with a compound, the cells are exposed to the MTT reagent and the more viable cells are present in a well, the more formazan dye is produced. Extent of formazan dye can be measured, for example, using a spectrophotometer. Other commonly used methods of detecting cell growth inhibition include the monitoring of DNA synthesis. Cells grown, for example, in the presence or absence of compound are also treated with a nucleotide analog that can incorporate into the DNA of the cell upon cell division. Examples of such nucleotide analogs include, for example, BrdU or $^3$H-thymidine. In each case, the amount of label incorporated into the cells (grown in the presence and absence of a given inhibitory agent) is quantified, and the amount of label incorporation is directly proportional to the amount of cell growth in the population of cells. In this context, cell proliferation (e.g., cancer cell proliferation) can be decreased by at least 10% (e.g., at least 15%, at least 20%, at least 25%, at least 30%, at least 35%, at least 40%, at least 50%, at least 55%, at least 60%, at least 65%, at least 70%, or at least 75% or more) relative to the cell proliferation in the absence of the inhibitor. It is understood that the methods described above can be used for detecting or measuring both cell proliferation and viability.

Comparisons of apoptosis can be accomplished by measuring a host of indicators, for example, DNA fragmentation, caspase activity, loss of mitochondrial membrane potential, increased production of reactive oxygen species (ROS), intracellular acidification, chromatin condensation, phosphatidyl serine levels at the cell surface, opening of the mitochondrial apoptosis-induced channel (MAC), or an increased cell permeability.

DNA fragmentation can be measured, e.g., by with the TUNEL assay (terminal deoxynucleotide transferase dUTP nick end labeling). Commercial versions of the assay are widely available, for example, APO-BrdU™ TUNEL Assay Kit (Invitrogen), APO-DIRECT™ Kit (BD-Biosciences-Pharmingen) and ApoAlert™ DNA fragmentation Assay Kit (Clontech).

Caspase activity can be measured via fluorogenic, chromogenic, and luminescent substrates specific for a given caspase (e.g., Caspase 3 or Caspase 9). Commercial kits are available for a variety of caspases such as caspase 3, caspase 7, caspase 8, and caspase 9 (see BD-Pharmingen or Invitrogen).

Loss of mitochondrial membrane potential can be measured with fluorescent dyes that selectively accumulate in various compartments of the mitochondria based on its integrity and functionality. One non-limiting example of such a dye is Mitotracker Red (Invitrogen).

Production of reactive oxygen species can be monitored with fluorescent dyes such as H2DCFDA.

Chromatin condensation can be measured with dyes such as Hoechst 33342 or propidium iodide.

Phosphotidyl serine (PS) levels can be measured at the cell surface. For example, Annexin V having a high affinity for PS, can be used to as a probe for PS on a cell surface. Numerous commercially available assay kits are suitable for such measurements (see BD-Biosciences Pharmingen).

Suitable methods for determining opening of the MAC, for example, in response to oligomerization of BH3-containing proapoptotic proteins, are described in Dejean et al. (2006) Biochem. Biophys. Acta. Mol. Basis. Dis. 1762(2):191-201; Dejean et al. (2006) Cell Death and Differentiation 13:1387-

1395; and Guihard et al. (2004) J. Biol. Chem. 45:46542-46550 and are further described in the Examples.

Yet another method of determining promotion of apoptosis by a compound is by studying the oligomerization of BAX and BAK. Exemplary methods are described in the following Examples (see Example 4). For example, the extent of BAX or BAK oligomerization in cells cultured in the presence or absence of a compound can be determined, wherein an increase amount of BAX or BAK oligomerization in a cell in the presence of the compound as compared to in the absence of the compound indicates that the compound promotes apoptosis.

In Vivo Methods of Promoting Apoptosis

The invention features in vivo methods of promoting apoptosis, which includes the steps of: identifying a subject as having, suspected of having (or at risk of developing), a cancer comprising one or more cancer cells expressing a BH3-containing proapoptotic protein; and delivering to the subject a compound that inhibits MUC1 (or a BH3-containing proapoptotic protein). The method can include the step of determining whether the one or more cancer cells of the subject's cancer express MUC1. The method can also include the step of determining whether inhibition of MUC1 occurred.

Alternatively, the method can include the steps of: identifying a subject as one having, suspected of having (or at risk of developing), a cancer comprising one or more cells expressing a BH2-containing antiapoptotic protein; and delivering to the subject a compound that inhibits the interaction between MUC1 and a BH3-containing proapoptotic protein, wherein the BH3-containing proapoptotic protein is capable of binding to the BH2-protein. The method can include the step of determining whether the one or more cancer cells of the subject's cancer express a BH2-containing antiapoptotic protein. The method can also include the step of determining whether inhibition of MUC1 and a BH3-containing antiapoptotic protein occurred.

Any of the preceeding methods of this section can involve identifying a subject as one having, suspected of having (or at risk of developing), an inflammatory condition wherein one or more inflammatory cells involved in the inflammatory condition express MUC1 and/or a BH2-containing antiapoptotic protein.

In one in vivo approach, a compound that inhibits MUC1 is administered to a subject (e.g., any of the subjects described herein).

In another in vivo approach, a compound that inhibits a BH2-containing antiapoptotic protein is administered to the subject.

The compounds of the invention will, generally, be suspended in a pharmaceutically-acceptable carrier (e.g., physiological saline) and administered by any of the methods described herein. Required dosage and administration schedules depends on a variety of factors set forth in the preceding sections. The compound can be administered alone (as a monotherapy) or can be administered in conjunction (as a multi-therapy regimen) with one or more additional therapeutic agents such as, but in no way limited to, those described herein.

Where an inhibitory compound is a polypeptide, a polynucleotide containing a nucleic acid sequence encoding the polypeptide can be delivered to appropriate cells in a mammal as described in detail above.

The subjects can be further treated with (e.g., be exposed to, have delivered, or have administered) one or more additional therapeutic (e.g., chemotherapeutic agents) as described above. Such therapeutic or chemotherapeutic agents can include any of the therapeutic or chemotherapeutic agents described herein.

Ex Vivo Methods of Promoting Apoptosis

An ex vivo strategy can involve transfecting or transducing cells obtained from the subject (or another subject) with a polynucleotide encoding a polypeptide that (i) inhibits MUC1 or (ii) inhibits a BH2-containing antiapoptotic protein. The transfected or transduced cells are then returned to the subject. The cells can be any of a wide range of types including, without limitation, any of the cells described above. Such cells act as a source of the inhibitory polypeptide for as long as they survive in the subject. Alternatively, tumor cells or inflammatory cells (e.g., immune cells), preferably obtained from the subject (autologous) but potentially from a subject of the same species other than the subject (allogeneic), can be transfected or transformed by a vector encoding the inhibitory polypeptide. The tumor cells, preferably treated with an agent (e.g., ionizing irradiation) that ablates their proliferative capacity, are then introduced into the subject, where they secrete the polypeptide.

The ex vivo methods include the steps of harvesting cells from a subject, culturing the cells, transducing them with an expression vector, and maintaining the cells under conditions suitable for expression of the polypeptide that inhibits MUC1 or a BH2-containing antiapoptotic protein. These methods are known in the art of molecular biology and suitable methods are described above.

G. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Targeting of MUC1-C to Mitochondria in the Response of MCF10A Cells to HRG

To assess the effects of heregulin (HRG) on MUC1-C binding to HSP90 and targeting to the mitochondrial outer membrane (MOM) in normal breast cells, MCF10A breast cells (which are immortalized but not transformed) are stimulated with 20 ng/mL of heregulin (HRG). Lysates are prepared from the treated cells and immunoblotted with an anti-phospho-MUC1-C-Tyr-46 antibody that specifically detects phosphorylation of the MUC1-C cytoplasmic domain on Tyr-46 and with anti-MUC1-C antibody. Binding of MUC1-C to HSP90 is then determined by immunoblot analysis of anti-MUC1-C precipitates with anti-HSP90 as described in Ren et al. (2006) Oncogene 25:20-31.

To determine if an increase in the presence or amount of MUC1-C associated with mitochondria occurs in MCF10A cells following HRG treatment, purified mitochondria are treated with 1% digitonin and/or 60 µg/ml trypsin, solubilized, and subjected to sodium dodecyl-polyacrylamide gel electrophoresis (SDS-PAGE). The presence and/or amount of MUC1-C localized at the mitochondria is detected by immunoblotting using anti-MUC1-C antibodies (Ren et al. (2006) Oncogene 25:20-31. An increase in both mitochondrial-associated MUC1-C and MUC1-C binding to HSP90 would indicate that HRG stimulates the localization of MUC1-C to the mitochondria and the binding of MUC1-C to HSP90 in normal breast cells.

Example 2

Role of MUC1 in Regulating Apoptosis and Luminal Filling of Mammary Acini

To define the role of MUC1 in the formation of mammary acini, normal breast MCF10A cells are first treated with siRNA specific for MUC1 to silence MUC1 expression. MCF10A cells (with and without MUC1 silencing) are then suspended in assay medium containing 4% Matrigel and 20 ng/ml HRG (Muthuswamy et al. (2001) Nat. Cell Biol. 3:785-792 and Debnath et al. (2003) Methods 30:256-268). The cell suspensions are added to individual chambers of a Matrigel-coated eight-chambered slide. The assay medium containing 20 ng/mL HRG is replaced every 4 days. Cell number is determined by disruption of the acinar structures with trypsin followed by cell counting. The acinar organization at different stages of morphogenesis are determined through confocal analysis of DAPI-labeled structures (Muthuswamy et al. (2001) Nat. Cell Biol. 3:785-792 and Debnath et al. (2003) Methods 30:256-268). Increased apoptosis in MUC1-silenced MCF10A cells grown in suspension would indicate that MUC1 plays a role in regulating apoptosis and luminal filling of normal mammary acini.

Example 3

Function of MUC1-C in Regulation of the Proapoptotic BH3-Only Bcl-2 Family Members To determine how MUC1 controls apoptosis following its translocation to the mitochondria (i.e., the mitochondrial outer membrane), the association of MUC1 with known MOM permeability regulators was assessed. Whole-cell lysates were prepared from MCF7 breast cancer cells and then subjected to immunoprecipitation using antibodies specific for MUC1 or an isotype non-specific antibody control. Immunoprecipitates were washed thoroughly, resuspended in Laemmli buffer and the immunoprecipitated proteins were resolved using SDS-PAGE. The various proteins in the immunoprecipates were detected by western blot using antibodies specific for MUC1-C and BID (FIG. 1A). MUC1 associates constitutively with BID in MCF-7 cells (FIG. 1A). By contrast, in similar immunoprecipitation experiments performed to study the interaction with other known antiapoptotic proteins (using antibodies specific for XIAP, cIAP1, cIAP, or MUC1-C), no detectable association between MUC1-C and XIAP, cIAP1 or cIAP2 was observed. These results indicate that the interaction between MUC1-C and BH3-only proteins are constitutive in breast cancer cells.

To determine if an increase in the interaction between MUC1 and BH3-only (or BH3-containing proapoptotic proteins) is induced in normal breast cancer cells in response to HRG, normal breast MCF10A cells are stimulated with HRG as described above. Whole cell lystates are prepared from treated cells (and non-treated cells as a control) and subjected to immunoprecipitation using anti-MUC1-C antibodies or control IgG serum. Increased MUC1-C/BH3-only protein association (e.g., BID) detected in immunoprecipitates of HRG-treated cells as compared to non-treated cells would indicate that while breast cancer cells display constitutive association between MUC1 and BH3-only proteins (e.g., BID), such association is induced in normal breast cells.

Interaction between MUC1-C and BH3-only proteins in the cytosol. MUC1-C accumulates in the cytosol of human breast cancer cells and cytosolic MUC1-C increases with HRG stimulation (Ren et al. (2006) Oncogene 25:20-31). The BH3-only proteins are also predominantly expressed in the cytosol (Danial et al. (2004) Cell 116:205-219). To address whether cytosolic MUC1-C associates with BID and BIM (and thus, e.g., blocks their interaction with BAX/BAK), cytosolic fractions are prepared from unstimulated and HRG-treated MCF10A and breast cancer cells (Ren et al. (2006) Oncogene 25:20-31). As a control for localization of MUC1-C-BID complexes in the cytosol, cell membrane fractions are also prepared (Ren et al. (2006) Oncogene 25:20-31). Soluble proteins from MCF10A cells are precipitated with an anti-MUC1-C antibody. The precipitates are then immunoblotted with anti-BID (Santa Cruz Biotechnology) and anti-MUC1-C antibodies. Based on the above results, it is expected that more MUC1-C/BID complex formation will be detected in HRG-treated MCF10A cells as compared to cells not treated with HRG. Such results would indicate that HRG induced complex formation between MUC1-C and BID, for example, in normal breast cells.

To determine whether MUC1-C associates with BIM, similar studies to those described above for BID are performed by immunoblotting anti-MUC1-C precipitates with anti-BIM (Santa Cruz Biotechnology) antibodies. In the reciprocal experiments, anti-BID and anti-BIM precipitates are immunoblotted with anti-MUC1-C antibodies. Based on the above results, it is expected that, much like that of BID, increased association of BIM and MUC1-C will result in MCF10A cells following HRG treatment.

Figure 1B:
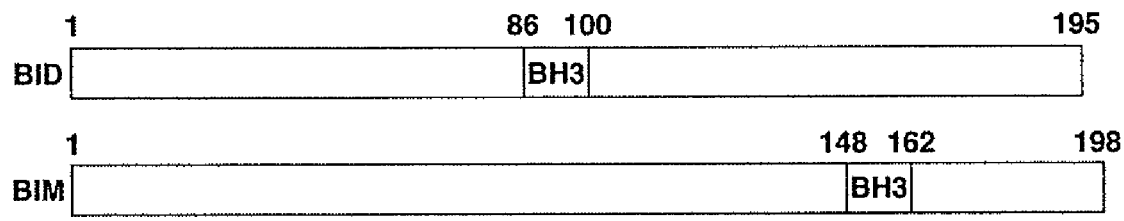
FIG. 1B is a diagram depicting the domain structure of human BID and BIM. "BH3" refers to the Bcl-2 homology domain 3. The numbers above the diagram indicate the amino acid position and denote the relative boundaries of the respective BH3 domain within the protein.

Direct binding of MUC1-CD to BH3-only proteins. With the exception of the BH3 domain, the BH3-only family is unrelated to Bcl-2. BID contains a unique N-terminal domain (amino acids 1 to 86), the conserved BH3 domain and a nonconserved C-terminal domain (amino acids 100 to 195) (FIG. 1B). BIM also has the conserved BH3 domain (amino acids 148 to 162).

To determine whether MUC1 binds directly to BID, GST and GST-BID are incubated with purified His-tagged MUC1-CD (Li et al. (1998) Mol. Cell. Biol. 18:7216-7224). The adsorbates to glutathione beads are immunoblotted with anti-MUC1-C. Similar binding studies are subsequently performed with GST-tagged fragments of BID, particularly the truncated p15 BID (tBID), to define the region responsible for the interaction. In addition, GST, GST-MUC1-CD(1-45) and GST-MUC1-CD(46-72) are incubated with purified BID (GST-BID subjected to thrombin cleavage to remove the GST reagent) to determine which region of MUC1-CD binds to BID (see FIG. 3A). Similar studies are performed with purified BIM.

Example 4

Effects of MUC1 on BAX/BAK Oligomerization and Cytochrome C Release

BID and BIM induce BAX/BAK oligomerization and cytochrome c release in a purified mitochondrial system (Letai et al. (2002) Cell 2:183-192). These BH3-only proteins have been designated "activators." By contrast, BAD and BIK are unable to induce cytochrome c release on their own, but function in freeing activators that are bound to Bcl-2/Bcl-$x_L$ (Letai et al. (2002) Cell 2:183-192). Experiments are carried out to determine if MUC1 blocks the ability of BID and BIM to induce BAX/BAK oligomerization and cytochrome c release.

To determine whether binding of MUC1 to BH3-only activators abrogates their function, GST-tBID and GST-BIM are purified and then cleaved with thrombin to remove the GST reagent. tBID or BIM at concentrations of 0.5 and 5 ng/μl are incubated at room temperature with mitochondria (0.5 μg/μl) purified from ZR-75-1/MUC1siRNA cells (ZR-75-1 cells stably expressing a MUC1-specific siRNA as described in Ren et al. (2004) Cancer Cell 5:163-175; and Ren et al. (2006) Oncogene 25:20-31). To assess the effects of MUC1-CD on BID and/or BIM-induced cytochrome c release by mitochondria, tBID or BIM are preincubated with a 10-fold excess of GST-MUC1-CD and then added to purified mitochondria. Incubations are performed as described in Letai et al. (2002) Cell 2:183-192. Release of cytochrome c will be determined by quantitating cytochrome c in the mitochondrial pellets and supernatants using a colorimetric ELISA (R&D Systems). Reduced amounts of BH3-protein-induced cytochrome c release from mitochondria in the presence of MUC1 as compared to the amount of cytochrome c released in the absence of MUC1 would indicate that MUC1 abrogates the ability of BH3-only proteins to induce cytochrome c release from mitochondria.

To detect the affect of MUC1 on the oligomerization of BAX and BAK, the MUC1-treated mitochondrial suspensions (see above) are incubated with 1 mM 1,6-bismaleimidohexane (BMH; Pierce) for 30 minutes at room temperature to cross-link proteins. The mitochondria are pelleted and then dissolved in NuPAGE buffer (Invitrogen). Proteins are then subjected to SDS-PAGE and immunoblotted with anti-BAX (N-20; Santa Cruz) and anti-BAK (Upstate Biotechnology) antibodies to detect oligomerization. A decrease in the amount of BAX-BAK oligomerization detected at mitochondria in the presence of MUC1 as compared to the amount of BAX-BAK oligomers in the absence of MUC1 would indicate that MUC1 prevents BAX-BAK oligomerization.

Example 5

Figure 2A:
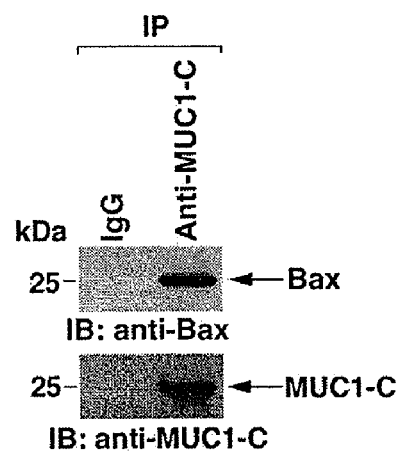
FIG. 2A is pair of photographs of western blots depicting the association of MUC1 with BAX. Whole-cell lysates were prepared from MCF7 cells and then subjected to immunoprecipitation (IP) using antibodies specific for MUC1 ("anti-MUC1-C") or an isotype non-specific control antibody ("IgG"). Immunoprecipitates were washed thoroughly, resuspended in Laemmli buffer and the immunoprecipitated proteins were resolved using SDS-PAGE. The various proteins were detected by western blot (immunoblot, "IB") using antibodies specific for MUC1-C and BAX (top and bottom photographs respectively). The relative positions (e.g., the molecular weights) of the proteins are reported in kilodaltons (kDa) and indicated to the left of each of the immunoblots (e.g., 25 kDa).

Function of Mitochondrial MUC1-C in Regulation of the Proapoptotic BAX and BAK Proteins BAX and BAK exist as inactive monomers in viable cells. BAX localizes to the cytosol and at the surface of mitochondria (Suzuki et al. (2000) Cell 103:645-654). In response to the "activator" BH3-only proteins, BAX undergoes oligomerization and integration into the MOM. Inactive BAK also undergoes oligomerization in response to activation by BID and BIM [Danial et al. (2004) Cell 116:205-219; Certo et al. (2006) Cancer Cell 9:351-365). MUC1-C accumulates in the cytosol and, in addition, is targeted to the MOM (Ren et al. (2004) Cancer Cell 5:163-175; and Ren et al. (2006) Oncogene 25:20-31). To determine whether MUC1-C binds directly to BAX/BAK in the MOM, the association of MUC1 with BAX was determined by coimmunoprecipitation experiments. Whole-cell lysates were prepared from MCF7 cells and then subjected to immunoprecipitation using an antibody specific for MUC1 or an isotype non-specific antibody control. Immunoprecipitates were washed thoroughly, resuspended in Laemmli buffer and the immunoprecipitated proteins were resolved using SDS-PAGE. The various proteins were detected by western blot using antibodies specific for MUC1-C and BAX (FIG. 2A). This experiment demonstrated that MUC1-C associates with BAX (FIG. 2A). By contrast, there was no detectable binding of MUC1-C with the multidomain antiapoptotic Bcl-2 and Bcl-$x_L$ proteins.

Association of MUC1-C with BAX/BAK in mitochondria. MUC1-C is constitutively targeted to the MOM of human breast cancer cells (Ren et al. (2004) Cancer Cell 5:163-175; and Ren et al. (2006) Oncogene 25:20-31). By contrast, little if any MUC1-C is detectable in the MOM of MCF10A cells. Thus, to determine whether (i) MUC1-C constitutively interacts with BAX/BAK in breast cancer cells, and (ii) stimulation of MCF10A cells with HRG targets MUC1-C to the MOM and thereby the interaction with BAX/BAK, mitochondria are prepared from control and HRG-treated MCF10A and breast cancer cells (Ren et al. (2004) Cancer Cell 5:163-175; and Ren et al. (2006) Oncogene 25:20-31; as above). The prepared mitochondria are solubilized in 1 mM CHAPS and subjected to Superose 6 gel filtration as described in Danial et al. (2003) Nature 645-654. The fractions are then subjected to SDS-PAGE and immunoblotted with anti-MUC1-C, anti-BAX or anti-BAK antibodies. MUC1-C positive fractions are immunoprecipitated with anti-MUC1-C antibodies. The resulting precipitates are then immunoblotted with anti-BAX and anti-BAK antibodies. In the reciprocal experiments, anti-BAX and anti-BAK precipitates are immunoblotted with an anti-MUC1-C antibody. Increased association of MUC1-C and BAX and/or BAK following HRG-treatment of MCF10A would indicate that the MUC1-C/BAX and/or MUC1-C/BAK interaction is regulated by HRG in normal breast cells. Whereas no change in the MUC1-C/BAX and/or BAK association in MCF7 cancer cells following HRG treatment, would indicate that the MUC1-C/BAX and/or MUC1-C/BAK interaction is constitutive in breast cancer cells.

Figure 2B:
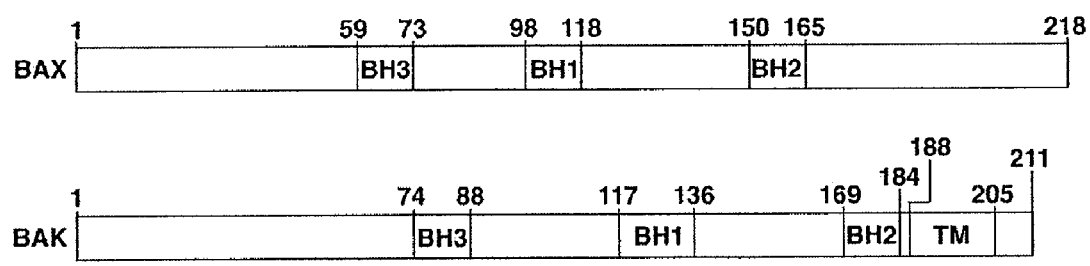
FIG. 2B is a diagram depicting the domain structure of human BAX and BAK. "BH3" refers to the Bcl-2 homology domain 3, "BH2" refers to the Bcl-2 homology domain 2, and "BH1" refers to the Bcl-2 homology domain 1. "TM" refers to the transmembrane domain in the BAK protein. The numbers above the diagram indicate amino acid position and denote the relative boundaries of the respective domains within the proteins.

Direct binding of MUC1-CD with BAX/BAK BAX and BAK contain BH3, BH1 and BH2 domains. BAK also includes a transmembrane domain (FIG. 2B). A hydrophobic cleft formed by the BH1-3 domains functions as a binding site for the amphipathic α helix of the BH3-only proteins (Kelekar et al. (1998) Trends Cell Biol. 8:324-330).

To determine whether MUC1 binds directly to BAX/BAK, GST, GST-BAX and GST-BAK are incubated with purified His-tagged MUC1-CD (Li et al. (1998) Mol. Cell. Biol. 18:7216-7224). The adsorbates to glutathione beads are subjected to SDS-PAGE and immunoblotted with anti-MUC1-C antibodies. As controls for specificity, similar experiments are performed with GST-Bcl-2 and GST-Bcl-$x_L$. His-MUC1 detected in GST-BAX and BAK adsorbates, but not in the GST-only control, would indicate that MUC1 directly binds to BAX and BAK.

Similar binding studies are also performed with GST-tagged fragments of BAX and BAK to define regions of these proteins responsible for the interaction. In addition, GST, GST-MUC1-CD(1-45) and GST-MUC1-CD(46-72) are incubated with purified BAX or BAK (GST-BAX and GST-BAK subjected to thrombin cleavage to remove the GST reagent) to determine which region of MUC1-CD binds to BAX and BAK (see FIG. 3A).

Example 6

Effects of Mitochondrial MUC1-C on BAX/BAK Oligomerization

To determine whether binding of MUC1 to BAX/BAK blocks their oligomerization, tBID or BIM at concentrations of 0.5 and 5 ng/μl are incubated at room temperature with mitochondria (0.5 µg/µl) purified from breast cancer cells that have been first treated with MUC1-specific siRNA to silence MUC1 expression (or control cells treated with a control siRNA; see above). Similar experiments as described above are also performed on mitochondria from control and HRG-stimulated MCF10A cells. Oligomerization of BAX/BAK and release of cytochrome c are determined as described above. It is expected that mitochondria isolated from MUC1-silenced cells are more susceptible to tBID or BIM-induced cytochrome c release than mitochondria isolated from control cells expressing MUC1. More tBID or BIM-induced BAX/BAK oligomerization observed on mitochondria isolated from MUC1-silenced cells as compared to mitochondria isolated from control, MUC1 expressing cells would indicate that MUC1 not only regulates cytochrome c release in normal breast cells, but also controls BAX/BAK oligomerization induced by tBID or BIM.

Example 7

MUC1 Interaction with "Sensitizer" BH3-Proteins

MUC1-C could also interact with "sensitizer" BH3-only proteins, such as BAD, BIK, NOXA, BNIP and PUMA. To test if MUC1-C interacts with "sensitizer" proteins, immunoprecipitation and direct binding experiments, such as those described above, are performed. Experiments that address whether MUC1-C blocks binding of the sensitizer BH3-only proteins to Bcl-2/Bcl-$x_L$ are also performed. For example, MCF7 cells overexpressing MUC1-C (or control cells not overexpressing MUC1-C) are treated with an apoptosis-inducing agent to induce the association of sensitizer BH3-proteins to Bcl-2 or Bcl-$x_L$. A reduction in the association of sensitizer BH3 proteins to Bcl-2 or Bcl-$x_L$ in the presence of elevated cellular MUC1 levels (MUC1 overexpression) would indicate that MUC1-C blocks the interaction between these two groups of apoptosis regulators.

Experiments are also performed to determine if MUC1-C prevents oligomeric BAX from opening the mitochondrial apoptosis-induced channel (MAC) that releases cytochrome c, e.g. as described in Dejean et al. (2005) Mol. Biol. Cell 16:2424-2432, the disclosure of which is incorporated herein by reference in its entirety. Increased BAX-induced MAC opening in MUC1-silenced cells and/or reduced BAX-induced MAC opening in MUC1 overexpressing cells would indicate that MUC1 can also prevent apoptosis in normal breast cells and breast cancer cells by inhibiting the opening of the MAC.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by this application.

What is claimed is:

1. A method of identifying a compound that inhibits the binding of MUC1 to a BH3-containing proapoptotic protein, the method comprising:
   (a) contacting a MUC1 reagent comprising the cytoplasmic domain of MUC1 with a MUC1-binding BH3-containing proapoptotic protein or a MUC1-binding fragment thereof in the presence of a candidate compound; and
   (b) determining whether the candidate compound inhibits binding of the MUC1 reagent to the BH3-containing proapoptotic protein or the fragment thereof.

2. The method of claim 1, wherein the BH3-containing proapoptotic protein comprises BID, t-BID, or BAX.

3. The method of claim 1, wherein the MUC1 reagent comprises MUC1.

4. The method of claim 1, wherein the cytoplasmic domain of MUC1 has the sequence SEQ ID NO: 2.

5. The method of claim 1, wherein the MUC1-biding fragment comprises a MUC1-binding fragment of BID, t-BID, or BAX.

* * * * *

UNITED STATES PATENT AND TRADEMARK OFFICE
CERTIFICATE OF CORRECTION

| | | |
|---|---|---|
| PATENT NO. | : 7,871,784 B2 | Page 1 of 1 |
| APPLICATION NO. | : 12/024715 | |
| DATED | : January 18, 2011 | |
| INVENTOR(S) | : Donald W. Kufe | |

It is certified that error appears in the above-identified patent and that said Letters Patent is hereby corrected as shown below:

In column 1, lines 10-13, delete
"The research described in this application was supported by grant no. CA97098 from the National Cancer Institute of the National Institutes of Health. Thus, the government has certain rights in the invention." and insert
--This invention was made with government support under grant number CA97098 from the National Cancer Institute of the National Institutes of Health. The government has certain rights in the invention--.

Signed and Sealed this

Twenty-sixth Day of April, 2011

David J. Kappos
*Director of the United States Patent and Trademark Office*